(12) United States Patent
Wei et al.

(10) Patent No.: US 8,076,345 B2
(45) Date of Patent: Dec. 13, 2011

(54) 2-CYANOPHENYL-7,8-DIHYDRO-5H-PYRIDO [4,3-D]PYRIMIDINE COMPOUNDS, COMPOSITIONS AND USES THEREOF

(75) Inventors: Zhi-Liang Wei, Foster City, CA (US); Donogh John Roger O'Mahony, San Mateo, CA (US); Matthew Duncton, San Francisco, CA (US); John Kincaid, San Francisco, CA (US); Michael G. Kelly, Thousand Oaks, CA (US); Zhan Wang, Palo Alto, CA (US)

(73) Assignee: Evotec AG, Hamburg (DE)

( * ) Notice: Subject to any disclaimer, the term of this patent is extended or adjusted under 35 U.S.C. 154(b) by 725 days.

(21) Appl. No.: 12/080,253

(22) Filed: Mar. 31, 2008

(65) Prior Publication Data

US 2008/0275037 A1    Nov. 6, 2008

Related U.S. Application Data

(60) Provisional application No. 60/925,109, filed on Apr. 17, 2007, provisional application No. 61/010,512, filed on Jan. 8, 2008.

(51) Int. Cl.
| | |
|---|---|
| A61K 31/519 | (2006.01) |
| C07D 471/04 | (2006.01) |
| A61P 19/02 | (2006.01) |
| A61P 25/16 | (2006.01) |
| A61P 25/28 | (2006.01) |
| A61P 11/06 | (2006.01) |
| A61P 25/18 | (2006.01) |
| A61P 25/22 | (2006.01) |
| A61P 29/00 | (2006.01) |

(52) U.S. Cl. .................. 514/264.11; 544/279
(58) Field of Classification Search .............. 544/279; 514/264.11
See application file for complete search history.

(56) References Cited

U.S. PATENT DOCUMENTS

| 3,424,760 A | 1/1969 | Helsey et al. |
|---|---|---|
| 3,424,761 A | 1/1969 | Helsey et al. |
| 2003/0092908 A1 | 5/2003 | Pitts et al. |
| 2006/0258689 A1 | 11/2006 | Kelly et al. |
| 2010/0137306 A1 * | 6/2010 | Tafesse ............... 514/234.5 |

FOREIGN PATENT DOCUMENTS

| DE | 2502588 | 7/1976 |
|---|---|---|
| WO | 0069849 | 11/2000 |
| WO | 0162737 | 8/2001 |
| WO | 0208221 | 1/2002 |
| WO | 02053558 | 7/2002 |
| WO | 02087513 | 11/2002 |
| WO | 03076427 | 9/2003 |
| WO | 03104230 | 12/2003 |
| WO | 2004041259 | 5/2004 |
| WO | 2004056774 | 7/2004 |

* cited by examiner

*Primary Examiner* — James O Wilson
*Assistant Examiner* — Cecilia M Jaisle
(74) *Attorney, Agent, or Firm* — Klauber & Jackson LLC

(57) ABSTRACT

Fused heterocyclic compounds are provided according to formula 1:

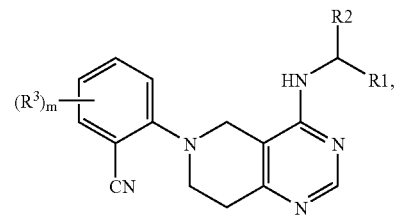

where $R^1$, $R^2$, $R^3$, and m are as defined herein. Provided compounds and pharmaceutical compositions thereof are useful for the prevention and treatment of a variety of conditions in mammals including humans, including by way of non-limiting example, pain, inflammation, cognitive disorders, anxiety, depression, and others.

24 Claims, No Drawings

2-CYANOPHENYL-7,8-DIHYDRO-5H-PYRIDO[4,3-D]PYRIMIDINE COMPOUNDS, COMPOSITIONS AND USES THEREOF

RELATED APPLICATIONS

The present application claims the priority of provisional applications U.S. Ser. No. 60/925,109, filed on Apr. 17, 2007 and U.S. Ser. No. 61/010,512, filed on Jan. 8, 2008. The disclosures of all of the aforementioned applications are incorporated by reference herein in their entireties. Applicants claim the benefits of these applications under 35 U.S.C. §119(e).

FIELD

Provided herein are fused heterocyclic compounds of the class tetrahydropyrido[4,3-d]pyrimidines and pharmaceutical compositions comprising such compounds. Also provided are methods for preventing and/or treating conditions in mammals, such as (but not limited to) arthritis, Parkinson's disease, Alzheimer's disease, asthma, myocardial infarction, pain syndromes (acute and chronic or neuropathic), neurodegenerative disorders, schizophrenia, cognitive disorders, anxiety, depression, inflammatory bowel disease and autoimmune disorders, and promoting neuroprotection, using the fused heterocyclic compounds and pharmaceutical compositions provided herein.

BACKGROUND

Therapeutic strategies for the effective management of pain and central nervous system disorders or diseases are sought.

International Patent Application, Publication Number WO 02/08221 discloses diaryl piperazine and related compounds which are said to be useful in the treatment of chronic and acute pain conditions, itch and urinary incontinence.

WO02/053558 describes certain quinazolone derivatives as alpha 1A/B adrenergic receptor antagonists, and WO03/076427 and WO04/041259 both describe compounds of the same class for use in the treatment of female sexual dysfunction. WO04/56774 describe certain substituted biphenyl-4-carboxylic acid arylamide analogues having possible application as receptor modulators. Also, WO03/104230 describes certain bicyclic pyrimidine derivatives, and US Published Application Serial No. 20030092908 and WO02/087513 describe fused heterocyclic PDE7 inhibitors.

U.S. Pat. Nos. 3,424,760 and 3,424,761 both describe a series of 3-ureidopyrrolidines that are said to exhibit analgesic, central nervous system, and psychopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fluorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino)ethyl]-1,2-dihydro-4-methyl-2-oxo-7-quinolinyl]-4-phenyl-1-piperazinecarboxamide.

SUMMARY

Fused heterocylic compounds, and pharmaceutical compositions thereof, having potency and selectivity in the prevention and treatment of conditions that have been associated with neurological and inflammatory disorders and dysfunctions are provided herein.

In particular, compounds, pharmaceutical compositions and methods provided are useful to treat, prevent or ameliorate a range of conditions in mammals such as, but not limited to, pain of various genesis or etiology, for example acute, chronic, inflammatory and neuropathic pain, dental pain and headache (such as migraine, cluster headache and tension headache). In some embodiments, compounds, pharmaceutical compositions and methods provided are useful for the treatment of inflammatory pain and associated hyperalgesia and allodynia. In some embodiments, compounds, pharmaceutical compositions and methods provided are useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). In some embodiments, compounds, pharmaceutical compositions and methods provided are useful as anti-inflammatory agents for the treatment of arthritis, and as agents to treat Parkinson's Disease, Alzheimer's Disease, asthma, myocardial infarction, neurodegenerative disorders, inflammatory bowel disease and autoimmune disorders, renal disorders, obesity, eating disorders, cancer, schizophrenia, epilepsy, sleeping disorders, cognitive disorders, depression, anxiety, blood pressure, and lipid disorders.

Accordingly, in one aspect, fused heterocyclic compounds are provided that have formula 1:

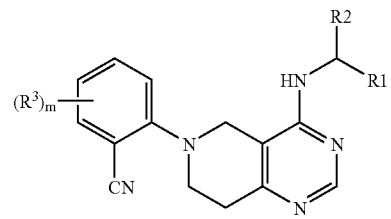

wherein $R^1$ is cycloalkyl, cycloheteroalkyl, aryl or heteroaryl unsubstituted or substituted with one or more $R^4$ groups;

$R^2$ is H, substituted or unsubstituted $C_1$-$C_6$ alkyl or cycloalkyl;

each $R^3$ and $R^4$ is independently selected from the group consisting of H, alkyl, acyl, acylamino, alkylamino, alkylthio, alkoxy, alkoxycarbonyl, alkylarylamino, arylalkyloxy, arylalkyloxy, amino, aryl, arylalkyl, sulfo, substituted sulfo, substituted sulfonyl, substituted sulfinyl, substituted sulfanyl, azido, carbamoyl, carboxyl, cyano, cycloalkyl, cycloheteroalkyl, dialkylamino, halo, heteroaryloxy, heteroaryl, heteroalkyl, hydroxy, nitro, and thiol; m is 1, 2 3 or 4;

or a pharmaceutically acceptable salt, solvate, prodrug, tautomer or isotopic variant thereof.

In another aspect, fused heterocyclic compounds are provided that have formula 2:

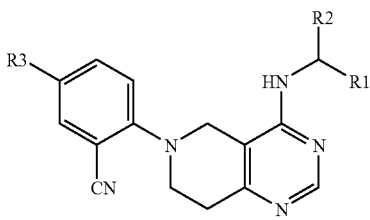

2 wherein $R^1$, $R^2$, $R^3$, and $R^4$ are as described for formula 1 or a pharmaceutically acceptable salt, solvate, prodrug, tautomer or isotopic variant thereof.

In certain embodiments, with respect to formula 2, $R^3$ is halo, substituted or unsubstituted $C_1$-$C_6$ alkyl or cycloalkyl. In further embodiments, $R^3$ is Cl, F, Me or $CF_3$.

In certain embodiments, the compounds according to formulae 1-2 are enantiomerically pure. In certain embodiments, provided are pharmaceutical compositions comprising enantiomerically pure compounds according to formulae 1-2. In certain embodiments, provided are methods of treatment that comprise administering an enantiomerically pure compound according to formulae 1-2 or a pharmaceutical composition comprising an enantiomerically pure compound according to formulae 1-2.

Accordingly, in one aspect, fused heterocyclic compounds are provided that have formula 3a or 3b:

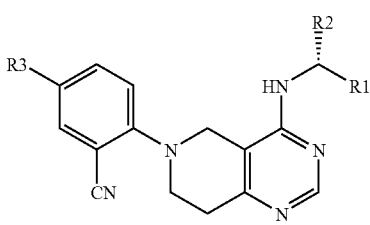

3a

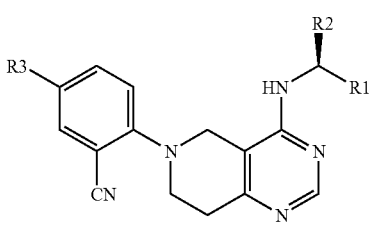

3b wherein $R^1$, $R^2$ and $R^4$ are as described for formula 1; and $R^3$ is halo, substituted or unsubstituted $C_1$-$C_6$ alkyl or cycloalkyl; or a pharmaceutically acceptable salt, solvate, prodrug, tautomer or isotopic variant thereof.

In certain embodiments, the compounds according to formula 3a or 3b are enantiomerically pure. In certain embodiments, pharmaceutical compositions are provided comprising enantiomerically pure compounds according to formula 3a or 3b. In certain embodiments, provided are methods of treatment that comprise administering an enantiomerically pure compound according to formula 3a or 3b or a pharmaceutical composition comprising an enantiomerically pure compound according to formula 3a or 3b.

In another aspect, pharmaceutical compositions are provided comprising a fused heterocyclic compound provided herein, and a pharmaceutical carrier, excipient or diluent. The pharmaceutical composition can comprise one or more of the fused heterocyclic compounds described herein.

It will be understood that fused heterocyclic compounds provided herein useful in the pharmaceutical compositions and treatment methods disclosed herein, can be pharmaceutically acceptable as prepared and used.

In another aspect, methods are provided for preventing, treating or ameliorating a condition from among those listed herein, and particularly, such condition as may be associated with, e.g., arthritis, asthma, myocardial infarction, lipid disorders, cognitive disorders, anxiety, schizophrenia, depression, memory dysfunctions such as Alzheimers disease, inflammatory bowel disease and autoimmune disorders, which method comprises administering to a mammal in need thereof an amount of one or more of the compounds as provided herein, or pharmaceutical composition thereof, effective to prevent, treat or ameliorate the condition.

In yet another aspect, methods are provided for preventing, treating or ameliorating a condition that gives rise to pain responses or that relates to imbalances in the maintenance of basal activity of sensory nerves in a mammal. The fused heterocyclic compounds provided herein have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In one aspect, methods are provided for preventing, treating or ameliorating a neurodegenerative disease or disorder in a mammal. A neurodegenerative disease or disorder can, for example, be Parkinson's disease, Alzheimer's disease and multiple sclerosis; diseases and disorders which are mediated by or result in neuroinflammation such as, for example, encephalitis; centrally-mediated neuropsychiatric diseases and disorders such as, for example, depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders; itch/pruritus such as, for example, psoriasis; obesity; lipid disorders; cancer; and renal disorders Typically, the methods comprise administering an effective condition-treating or condition-preventing amount of one or more of the compounds as provided herein, or pharmaceutical composition thereof, to the mammal in need thereof.

In addition to the methods of treatment set forth above, the present invention extends to the use of any of the compounds of the invention for the preparation of medicaments that may be administered for such treatments, as well as to such compounds for the treatments disclosed and specified.

In additional aspects, methods are provided for synthesizing the fused heterocyclic compounds described herein, with representative synthetic protocols and pathways described below. In certain embodiments, provided are methods of making enantiomerically pure compounds according to formula 1 by asymmetric synthesis. In certain embodiments, provided are methods of making enantiomerically pure compounds according to formula 1 by chiral resolution.

Other objects and advantages will become apparent to those skilled in the art from a consideration of the ensuing detailed description.

DETAILED DESCRIPTION OF THE PREFERRED EMBODIMENTS

The following terms are intended to have the meanings presented therewith below and are useful in understanding the description and intended scope of the present invention.

When describing the compounds, pharmaceutical compositions containing such compounds and methods of using such compounds and compositions, the following terms have the following meanings unless otherwise indicated. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

"Acyl" refers to a radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —$NR^{21}C(O)R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)$R^{23}$ where $R^{23}$ is hydrogen, alkyl, aryl or cycloalkyl.

"Substituted alkenyl" refers to those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —O$R^{24}$ where $R^{24}$ is alkyl Exemplary alkoxy includes methoxy, ethoxy, n-propoxy, i-propoxy, n-butoxy, and heptoxy. Particular alkoxy groups are lower alkoxy, i.e. with between 1 and 6 carbon atoms.

"Substituted alkoxy" refers to those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —$NR^{25}$C(O)O$R^{26}$, where $R^{25}$ is hydrogen, alkyl, aryl or cycloalkyl, and $R^{26}$ is alkyl or cycloalkyl.

"Alkyl" refers to monovalent saturated alkane radical groups particularly having up to about 11 carbon atoms, more particularly, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms.

"Substituted alkyl" refers to those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

"Substituted alkylene" refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Aryl groups may be monocyclic or a bicyclic fused-ring structure where at least one of the rings is an aromatic ring structure that particularly contains 6 carbons. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta 2,4 diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms. Particularly, the aryl group may contain 6 carbon atoms. Exemplary aryl groups include phenyl and indan-1-one.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-$NR^{28}R^{29}$, wherein each of $R^{28}$ and $R^{29}$ are independently selected from hydrogen and alkyl.

"Arylamino" refers to the group aryl-$NR^{30}R^{31}$, wherein each of $R^{30}$ and $R^{31}$ are independently selected from hydrogen, aryl and heteroaryl.

"Alkoxyamino" refers to a radical —N(H)O$R^{32}$ where $R^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —$NR^{33}R^{34}$ where $R^{33}$ represents an alkyl or cycloalkyl group and $R^{34}$ is an aryl as defined herein.

"Alkylsulfonyl" refers to a radical —S(O)$_2$$R^{35}$ where $R^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)$R^{31}$ where $R^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —S$R^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" refers to those groups recited in the definition of "substituted" herein, and particularly refers to the group —N($R^{36}$)$_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N($R^{36}$)$_2$ is an amino group.

"Aminocarbonyl" refers to the group —C(O)$NR^{37}R^{37}$ where each $R^{37}$ is independently hydrogen, alkyl, aryl and cycloalkyl, or where the $R^{37}$ groups are joined to form an alkylene group.

"Aminocarbonylamino" refers to the group —$NR^{38}$C(O)$NR^{38}R^{38}$ where each $R^{38}$ is independently hydrogen, alkyl, aryl or cycloalkyl, or where two R groups are joined to form an alkylene group.

"Aminocarbonyloxy" refers to the group —OC(O)$NR^{39}R^{39}$ where each $R^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NH$R^{40}$ where $R^{40}$ represents an aryl group as defined herein.

"Aryloxycarbonyl" refers to a radical —C(O)—O-aryl where aryl is as defined herein.

"Arylsulfonyl" refers to a radical —S(O)$_2$$R^{41}$ where $R^{41}$ is an aryl or heteroaryl group as defined herein.

"Azido" refers to the radical —$N_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —$C(O)N(R^{42})_2$ where each $R^{42}$ group is independently hydrogen, alkyl, cycloalkyl or aryl, as defined herein, which may be optionally substituted as defined herein. In a specific embodiment, the term "carbamoyl" refers to —$C(O)$—$NH_2$. In an alternative embodiment "carbamoyl lower alkyl" means the radical $NH_2CO$-lower alkyl. Particular carbamoyl lower alkyl groups include carbamoylethyl and carbamoylmethyl.

"Carboxy" refers to the radical —$C(O)OH$.

"Carboxyamino" refers to the radical —$N(H)C(O)OH$.

"Compounds of the present invention", and equivalent expressions, are meant to embrace the compounds as hereinbefore described, in particular compounds according to any of the formulae herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

"Cycloalkylalkyl" refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocycloalkylalkyl" refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Halo" or "halogen" means fluoro (F), chloro (Cl), bromo (Br), or iodo (I).

"Hydrogen" means in the context of a substituent that —H is present at the compound position and also includes its isotope, deuterium.

"Lower alkanoyl amino" means an amino group with an organic functional group R—CO—, where R represents a lower alkyl group.

"Lower alkoxy" means 1 to 6 carbon atoms in a linear alkyl chain that may be straight or branched, and that is bonded by an oxygen atom.

"Lower alkyl sulfonamide" refers to a lower alkyl amide of sulfonamide of the formula —$SO_2NR*R*$, where R* is hydrogen or lower alkyl, and at least one R* is lower alkyl.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like. Particular cycloalkyl groups have between 4 and 7 carbon ring members for example cyclopropyl, cyclobutyl, cyclopentyl, cyclohexyl and cycloheptyl.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —$OR^{43}$ where $R^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —$NR^{44}R^{45}$ where $R^{44}$ and $R^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —$NO_2$.

"Substituted" refers to a group in which one or more hydrogen atoms are each independently replaced with the same or different substituent(s). Typical substituents include, but are not limited to, —X, —$R^{46}$, —$O^-$, =O, —$OR^{46}$, —$SR^{46}$, —$S^{31}$, S, —$NR^{46}R^{47}$, =$NR^{46}$, —$CX_3$, —$CF_3$, —CN, —OCN, —SCN, —NO, —$NO_2$, =$N_2$, —$N_3$, —$S(O)_2O$—, —$S(O)_2OH$, —$S(O)_2R^{46}$, —$OS(O_2)O$—, —$OS(O)_2R^{46}$, —$P(O)(O^-)_2$, —$P(O)(OR^{46})(O^-)$, —$OP(O)(OR^{46})(OR^{47})$, —$C(O)R^{46}$, —$C(S)R^{46}$, —$C(O)OR^{46}$, —$C(O)NR^{46}R^{47}$, —C(O)O—, —$C(S)OR^{46}$, —$NR^{41}C(O)NR^{46}R^{47}$, —$NR^{48}C(S)NR^{46}R^{47}$, —$NR^{49}C(NR^{41})NR^{46}R^{47}$ and —$C(NR^{48})NR^{46}R^{47}$, where each X is independently a halogen; each $R^{46}$, $R^{47}$, $R^{48}$ and $R^{49}$ are independently hydrogen, alkyl, substituted alkyl, aryl, substituted aryl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{50}R^{51}$, —$C(O)R^{50}$ or —$S(O)_2R^5$, or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

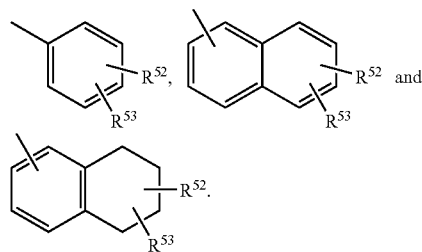

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, $NR^{54}COR^{55}$, $NR^{54}SOR^{55}$, $NR^{54}SO2R^{57}$, COO-alkyl, COO-aryl, $CONR^{54}R^{55}$, $CONR^{54}OR^{55}$, $NR^{54}R^{55}$, $SO_2NR^{54}R^{55}$, S-alkyl, S-alkyl, SO-alkyl, $SO_2$-alkyl, S-aryl, SO-aryl, $SO_2$-aryl; or $R^{52}$ and $R^{53}$ may be joined to form a cyclic ring (saturated or unsaturated) from 5 to 8 atoms, optionally containing one or more heteroatoms selected from the group N, O or S. $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, heterocycloalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. The heteroaryl group may be a monocyclic group (in which case it will typically be a 5 to 7, more typically a 5 or 6 membered ring), alternatively the heteroaryl group may be a bicycloheteroaryl group in particular a fused ring system comprising 2 fused 5-membered rings, a fused 5 and 6 membered ring or two fused 6 membered rings, where the heteroaryl group comprises fused rings at least one of said rings should contain a heteroatom and at least one said rings should be aromatic (both requirements may or may not be fulfilled in the same ring). The heteroaryl group can be, for example, a five membered or six membered monocyclic ring which may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Particularly, the heteroaryl group is between 5-15 membered heteroaryl, with 5-10 membered heteroaryl being particular groups. Particular heteroaryl groups are those derived from thiophene, pyrrole, benzothiophene, benzofuran, indole, pyridine, quinoline, imidazole, oxazole and pyrazine. Particularly, examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Particularly, examples of six membered heteroaryl groups include but are not limited to pyridine, pyrazine, pyridazine, pyrimidine and triazine.

Examples of representative heteroaryls include the following:

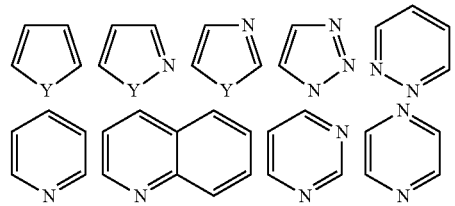

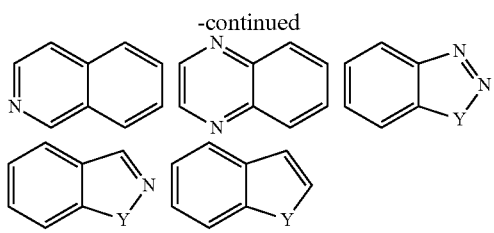

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

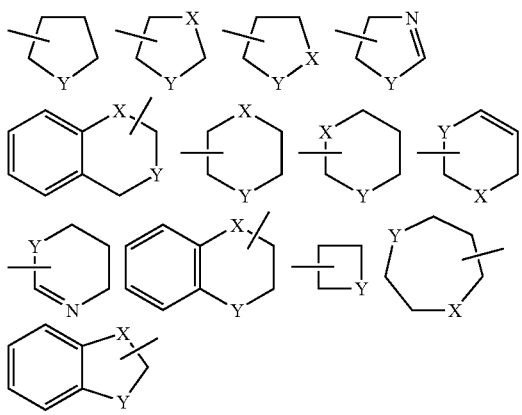

wherein each X is selected from CR$^{58}$, CR$^{58}_2$, NR$^{58}$, O and S; and each Y is selected from NR$^{58}$, O and S; and R$^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

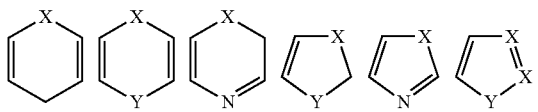

wherein each X is selected from CR$^{58}$, CR$^{58}_2$, NR$^{58}$, O and S; and each Y is selected from carbonyl, N, NR$^{58}$, 0 and S; and R$^{58}$ is independently hydrogen, alkyl, cycloalkyl, cycloheteroalkyl, aryl, heteroaryl, heteroalkyl or the like.

Examples of representative aryls having hetero atoms containing substitution include the following:

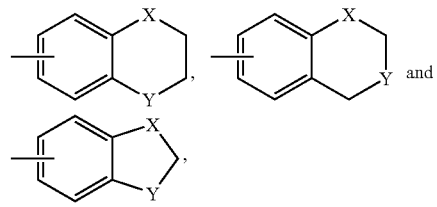

wherein each X is selected from CR$^{58}$, CR$^{58}_2$, NR$^{58}$, O and S; and each Y is selected from carbonyl, NR$^{58}$, 0 and S; and R$^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R$^4$ in a R$^4$C group present as substituents directly on a ring atom of the compounds provided herein or may be present as a substituent in the "substituted" aryl and aliphatic groups present in the compounds.

Examples of hetero substituents include:
-halo,
—NO$_2$, —NH$_2$, —NHR$^{59}$, —N(R$^{59}$)$_2$,
—NRCOR, —NR$^{59}$SOR$^{59}$, —NR$^{59}$SO$_2$R$^{59}$, OH, CN,
—CO$_2$H,
—R$^{59}$—OH, —O—R$^{59}$, —COOR$^{59}$,
—CON(R$^{59}$)$_2$, —CONROR$^{59}$,
—SO$_3$H, —R$^{59}$—S, —SO$_2$N(R$^{59}$)$_2$,
—S(O)R$^{59}$, —S(O)$_2$R$^{59}$ wherein each R$^{59}$ is independently an aryl or aliphatic, optionally with substitution. Among hetero substituents containing R$^{59}$ groups, preference is given to those materials having aryl and alkyl R$^{59}$ groups as defined herein. Preferred hetero substituents are those listed above.

"Hydrogen bond donor" group refers to a group containing O—H, or N—H functionality. Examples of "hydrogen bond donor" groups include —OH, —NH$_2$, and —NH—R$^{59a}$ and wherein R$^{59a}$ is alkyl, acyl, cycloalkyl, aryl, or heteroaryl.

"Dihydroxyphosphoryl" refers to the radical —PO(OH)$_2$.

"Substituted dihydroxyphosphoryl" refers to those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Nitrogen-Containing Heterocycloalkyl" group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioalkoxy" refers to the group —SR$^{60}$ where R$^{60}$ is alkyl.

"Substituted thioalkoxy" refers to those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein. In particular, R is substituted or unsubstituted alkyl substituted or unsubstituted aryl or substituted or unsubstituted heteroaryl.

"Sulfinyl" refers to the divalent radical —S(O)—. "Substituted sulfinyl" refers to a radical such as —SOR$^{61a}$, wherein R$^{61a}$ is any substituent described herein. In particular, R$^{61a}$ is substituted or unsubstituted alkyl, substituted or unsubstituted aryl or substituted or unsubstituted heteroaryl.

"Aminosulfonyl" or "Sulfonamide" refers to the radical H$_2$N(O$_2$)S—, and "substituted aminosulfonyl" "substituted sulfonamide" refers to a radical such as R$^{62}_2$N(O$_2$)S— wherein each R$^{62}$ is independently any substituent described herein.

"Sulfonyl" refers to the divalent radical —S(O$_2$)—. "Substituted sulfonyl" refers to a radical such as —S(O$_2$)R$^{61}$, wherein R$^{61}$ is any substituent described herein. In particular, R$^{61}$ is substituted or unsubstituted alkyl or substituted or unsubstituted aryl.

"Aminosulfonyl" or "Sulfonamide" refers to the radical H$_2$N(O$_2$)S—, and "substituted aminosulfonyl" "substituted sulfonamide" refers to a radical such as R$^{62}_2$N(O$_2$)S— wherein each R$^{62}$ is independently any substituent described herein.

"Sulfonamide" refers to a group of compounds containing the chemical group —SO$_2$NH$_2$.

"Sulfone" refers to the group —SO$_2$R$^{63}$. In particular embodiments, R$^{63}$ is selected from lower alkyl, alkyl, aryl and heteroaryl.

"Sulfo" or "sulfonic acid" refers to a radical such as —SO$_3$H.

"Substituted Sulfo" or "sulfonic acid ester" refers to a radical such as —SO$_3$R$^{61b}$ wherein R$^{61b}$ is substituted or unsubstituted alkyl or substituted or unsubstituted aryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

"Pharmaceutically acceptable salt" refers to the non-toxic, inorganic and organic acid addition salts, and base addition salts, of compounds of the present invention, in particular they are pharmaceutically acceptable and possess the desired pharmacological activity of the parent compound. These salts can be prepared in situ during the final isolation and purification of compounds useful in the present invention. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. "Solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. Conventional solvents include water, ethanol, acetic acid and the like, therefore, representative solvates include hydrates, ethanolates and methanolates.

"Subject" refers to humans and non-human mammals. In certain embodiments, a subject is a human.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

"Isotopic variant" refers to a compound that contains unnatural proportions of isotopes at one or more of the atoms that constitute such compound. For example, an "isotopic variant" of a compound can contain one or more non-radioactive isotopes, such as for example, deuterium (2H or D), carbon 13 ($^{13}C$), nitrogen-15 ($^{15}N$), or the like. It will be understood that, in a compound where such isotopic substitution is made, the following atoms, where present, may vary, so that for example, any hydrogen may be 2H/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)— or (S)— stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

"Subject" includes humans. The terms "human", "patient" and "subject" are used interchangeably herein.

"Prophylaxis" means a measure taken for the prevention of a disease.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means that amount of a drug or pharmaceutical agent that will elicit the biological or medical response of a subject that is being sought by a medical doctor or other clinician. The "therapeutically effective amount" can vary depending on the compound, the disease and its severity, and the age, weight, etc., of the subject to be treated.

Other derivatives of the compounds provided herein can have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

The Compounds

In certain aspects, provided herein are fused heterocyclic compounds useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In one aspect, provided herein are fused heterocyclic compounds according to formula 1, or 2:

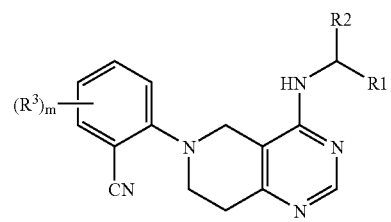

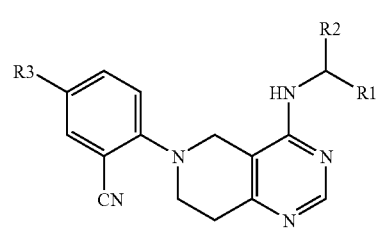

wherein $R^1$ is cycloalkyl, cycloheteroalkyl, aryl or heteroaryl unsubstituted or substituted with one or more $R^4$ groups;

$R^2$ is H, substituted or unsubstituted $C_1$-$C_6$ alkyl or cycloalkyl;

each $R^3$ and $R^4$ is independently selected from the group consisting of H, alkyl, acyl, acylamino, alkylamino, alkylhio, alkoxy, alkoxycarbonyl, alkylarylamino, arylalkyloxy, arylalkyloxy, amino, aryl, arylalkyl, sulfo, substituted sulfo, substituted sulfonyl, substituted sulfinyl, substituted sulfanyl, azido, carbamoyl, carboxyl, cyano, cycloalkyl, cycloheteroalkyl, dialkylamino, halo, heteroaryloxy, heteroaryl, heteroalkyl, hydroxy, nitro, and thiol; m is 1, 2 3 or 4; or a pharmaceutically acceptable salt, solvate, prodrug, stereoisomer, tautomer or isotopic variant thereof.

In certain embodiments, $R^3$ is halo, substituted or unsubstituted $C_1$-$C_6$ alkyl or cycloalkyl.

In another aspect, provided herein are fused heterocyclic compounds according to formula 3a or 3b:

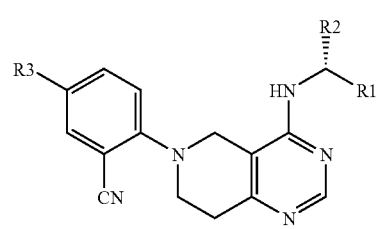

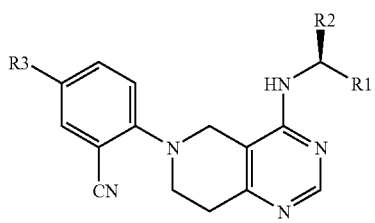

wherein
R¹ is cycloalkyl, cycloheteroalkyl, aryl or heteroaryl unsubstituted or substituted with one or more R⁴ groups;
R² is H, substituted or unsubstituted $C_1$-$C_6$ alkyl or cycloalkyl;
each R³ and R⁴ is independently selected from the group consisting of H, alkyl, acyl, acylamino, alkylamino, alkylthio, alkoxy, alkoxycarbonyl, alkylarylamino, arylalkyloxy, arylalkyloxy, amino, aryl, arylalkyl, sulfo, substituted sulfo, substituted sulfonyl, substituted sulfinyl, substituted sulfanyl, azido, carbamoyl, carboxyl, cyano, cycloalkyl, cycloheteroalkyl, dialkylamino, halo, heteroaryloxy, heteroaryl, heteroalkyl, hydroxy, nitro, and thiol; m is 1, 2 3 or 4; or
a pharmaceutically acceptable salt, solvate, prodrug, stereoisomer, tautomer or isotopic variant thereof.

In certain embodiments, the compound is according to formula 1, 2, 3a or 3b.

In one embodiment, with respect to formulae 1-3b, R² is H.

In another embodiment, with respect to formulae 1-3b, R² is other than H.

In certain embodiments, with respect to formulae 1-3b, R² is substituted or unsubstituted $C_1$-$C_6$ alkyl or cycloalkyl; and the compounds are enantiomerically pure. In certain embodiments, provided are pharmaceutical compositions comprising enantiomerically pure compounds according to formula 1, 2, 3a or 3b. In certain embodiments, provided are methods of treatment that comprise administering an enantiomerically pure compound according to formula 1, 2, 3a or 3b or a pharmaceutical composition comprising an enantiomerically pure compound according to formula 1, 2, 3a or 3b.

In some embodiments, with respect to formulae 1-3b, R¹ is an aryl or heteroaryl group.

In some embodiments, with respect to formulae 1-3b, R¹ is a cycloalkyl or cycloheteroalkyl group.

In some embodiments, with respect to formulae 1-3b, R¹ is selected from substituted or unsubstituted

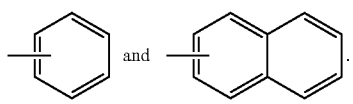

In some embodiments, with respect to formulae 1-3b, R¹ is selected from substituted or unsubstituted

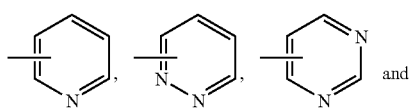

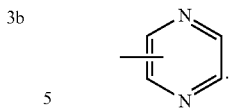

In certain embodiments, with respect to formulae 1-3b, R¹ is selected from substituted or unsubstituted

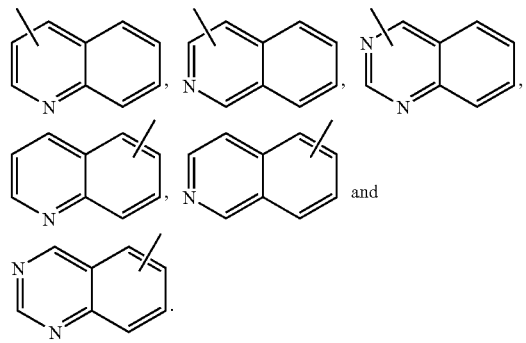

In some embodiments, with respect to formulae 1-3b, R¹ is selected from substituted or unsubstituted aryl, substituted or unsubstituted heteroaryl, substituted or unsubstituted cycloalkyl, substituted or unsubstituted cycloheteroalkyl, substituted or unsubstituted cycloalkenyl, substituted or unsubstituted cycloheteroalkenyl, substituted or unsubstituted bicycloalkyl, substituted or unsubstituted bicycloheteroalkyl, substituted or unsubstituted bicycloalkenyl, substituted or unsubstituted bicycloheteroalkenyl, substituted or unsubstituted bicycloaryl, and substituted or unsubstituted bicycloheteroaryl.

In some embodiments, with respect to formulae 1-3b, R¹ is selected from substituted or unsubstituted quinolinyl, isoquinolinyl, quinoxaline, methylenedioxyphenyl, imidazopyridyl, benzoxazolyl, and indolyl.

In some embodiments, with respect to formulae 1-3b, R¹ is selected from unsubstituted quinolinyl, isoquinolinyl, quinoxaline, methylenedioxyphenyl, imidazopyridyl, benzoxazolyl, and indolyl.

In some embodiments, with respect to formulae 1-3b, R¹ is selected from unsubstituted quinolinyl, isoquinolinyl, and quinoxaline.

In some embodiments, with respect to formulae 1-3b, R¹ is selected from quinolinyl, isoquinolinyl, quinoxaline, methylenedioxyphenyl, imidazopyridyl, benzoxazolyl, and indolyl, substituted with halo, haloalkyl, alkoxy, cyano, amino, sulfo, substituted sulfo, substituted sulfonyl, sulfonamide and cycloalkyl.

In some embodiments, with respect to formulae 1-3b, R¹ is selected from quinolinyl, isoquinolinyl, quinoxaline, methylenedioxyphenyl, imidazopyridyl, benzoxazolyl, and indolyl, substituted with Me, Et, Pr, iso-Pr, Ph, Cl, F, Br, CN, OH, OMe, OEt, OPh, COPh, $CO_2Me$, $CH_2$—N-morpholino, $CH_2$—N-(4-Me-piperidino), $NH_2$, $CONH_2$, $CF_3$, $CHF_2$, $OCF_3$, $OCHF_2$, t-Bu, SMe, CH═CH—$CO_2H$, SOMe, $SO_2Me$, $SO_2CF_3$, $SO_2NH_2$, $SO_3H$, $SO_3Me$, cyclopropyl.

In some embodiments, with respect to formulae 1-3b, R¹ is a phenyl. In certain embodiments, R¹ is a substituted phenyl.

In some embodiments, with respect to formulae 1-3b, R¹ is a mono-substituted phenyl.

In other embodiments, with respect to formulae 1-3b, R¹ is a di-substituted phenyl.

In certain embodiments, with respect to formulae 1-3b, $R^1$ is a substituted phenyl where the substituent on the phenyl is selected from halo, amido, alkyl, alkoxy, sulfonyl, sulfonamidyl, haloalkyl and trihaloalkyl. In preferred embodiments, the substitution on the $R^1$ phenyl is selected from Cl, F, $CF_3$, Me, OMe, $SO_2R^{2'}$, $NR^{2'}R^{2'}$, and $SO_2NR^{2'}R^{2'}$. In more preferred embodiments, the substitution on the $R^1$ phenyl is selected from H, Cl, Me and $SO_2$Me.

In certain embodiments, with respect to formulae 1-3b, $R^1$ is a disubstituted phenyl, and the two substitutions are selected from substituted sulfonyl, halo, and alkyl.

In certain embodiments, with respect to formulae 1-3b, $R^1$ is a disubstituted phenyl, and one substitution is $SO_2$Me and the other substitution is Cl, Me, or $CF_3$.

In embodiments where with respect to formulae 1-3b, $R^1$ is a substituted phenyl, one or more substitutents are on the phenyl at the 2 (ortho), 3 (meta) and/or 4 (para) position relative to the carbon attached to the nitrogen atom in the fused heterocyclic scaffold in formula 1, 1a or 1b.

In some embodiments, with respect to formulae 1-3b, $R^1$ is a heteroaryl.

In certain embodiments, with respect to formulae 1-3b, $R^1$ is a substituted pyridyl or pyrimidine group.

In some embodiments, with respect to formulae 1-3b, $R^1$ is a substituted pyridyl.

In some embodiments, with respect to formulae 1-3b, $R^1$ is a substituted pyrid-3-yl. In certain embodiments, the $R^1$ pyrid-2-yl is di-substituted. In preferred embodiments, the $R^1$ pyrid-3-yl is mono substituted.

In some embodiments, with respect to formulae 1-3b, $R^1$ is a substituted pyrid-3-yl and the substituent on the $R^1$ pyrid-3-yl is selected from halo, amido, alkyl, alkoxy, sulfonyl, sulfonamidyl, haloalkyl and trihaloalkyl.

In preferred embodiments, with respect to formulae 1-3b, the substitution on $R^1$ pyrid-3-yl is selected from Cl, F, $CF_3$, Me, OMe, $SO_2R^2$, $NR^{2'}R^{2'}$, and $SO_2NR^{2'}$, $R^{2'}$. In more preferred embodiments, the substitution on $R^1$ pyrid-3-yl is selected from Cl, Me and $SO_2$Me.

In some embodiments, $R^1$ is selected from

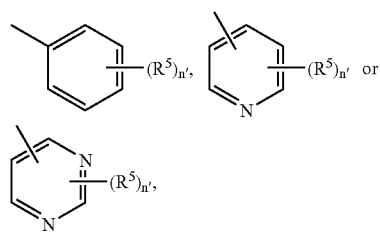

wherein subscript n' is selected from 1-5 and each of $R^5$ is independently selected from hydrogen, substituted or unsubstituted alkyl, substituted or unsubstituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, sulfo, substituted sulfo, substituted sulfonyl, substituted sulfinyl, substituted sulfanyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol.

In certain embodiments, the subscript n' is 1, 2 or 3.

In further embodiments, the subscript n' is 1 or 2.

In certain embodiments, each $R^5$ is H.

In certain embodiments, each $R^5$ is independently alkyl or substituted alkyl.

In certain embodiments, each $R^5$ is independently Cl or F.

In certain embodiments, each $R^5$ is independently alkoxy or substituted alkoxy.

In certain embodiments, each $R^5$ is independently amino or substituted amino.

In certain embodiments, each $R^5$ is independently carbamoyl.

In certain embodiments, each $R^5$ is independently sulfo or substituted sulfo.

In certain embodiments, each $R^5$ is independently sulfonyl or substituted sulfonyl.

In certain embodiments, each $R^5$ is independently aminosulfonyl or substituted aminosulfonyl.

In certain embodiments, each $R^5$ is independently $SO_2NH_2$.

In certain embodiments, each $R^5$ is independently selected from Me, Et, Pr, iso-Pr, Ph, Cl, F, Br, CN, OH, OMe, OEt, OPh, COPh, $CO_2$Me, $CH_2$—N-morpholino, $CH_2$—N-(4-Me-piperidino), $NH_2$, $CONH_2$, $CF_3$, $CHF_2$, $OCF_3$, $OCHF_2$, t-Bu, SMe, CH=CH—$CO_2$H, SOMe, $SO_2$Me, $SO_2CF_3$, $SO_2NH_2$, $SO_3$H, $SO_3$Me, cyclopropyl, triazolyl, morpholinyl, and pyridyl.

In certain embodiments, the subscript n' is 1 and $R^5$ is selected from Me, Cl, F, OMe, and $CF_3$.

In some embodiments, with respect to formulae 1-3b, $R^1$ is

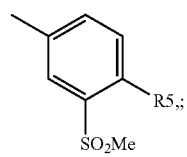

and $R^5$ is halo or alkyl. In one embodiment, $R^5$ is Cl or Me.

With regard to formula 1, in certain embodiments, a compound is according to formula 4a, 4b, or 4c:

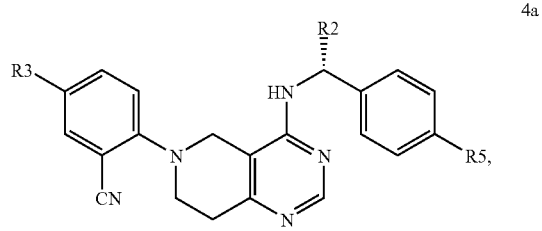

4a

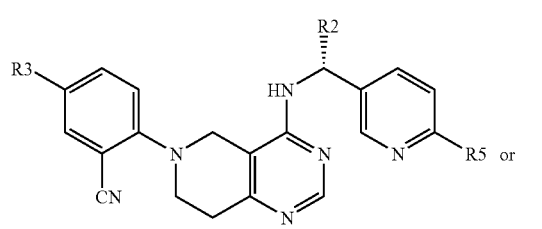

4b or

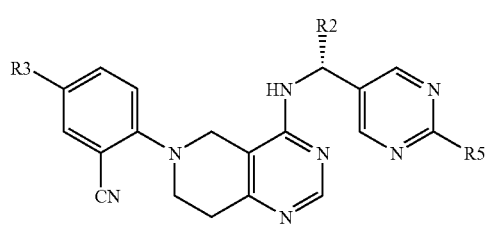

4c

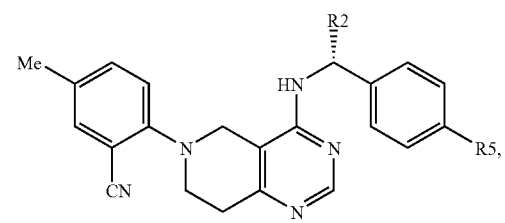

5a wherein $R^2$ is as described for formulae 3a-3b and $R^5$ is as described above. In certain embodiments, when $R^2$ is other than H, the compounds according to formula 4a, 4b, or 4c are enantiomerically pure. In certain embodiments, pharmaceutical compositions are provided comprising enantiomerically pure compounds according to formula 4a, 4b, or 4c. In certain embodiments, methods of treatment are provided that comprise administering an enantiomerically pure compound according to formula 4a, 4b, or 4c or a pharmaceutical composition comprising an enantiomerically pure compound according to formula 4a, 4b, or 4c.

In certain embodiments, with respect to formulae 4a-4-c, $R^5$ is H.

In certain embodiments, with respect to formulae 4a-4-c, $R^5$ is Me, Et, Pr, iso-Pr, Ph, Cl, F, CN, OH, OMe, OEt, OPh, $CF_3$, $CHF_2$, $OCF_3$, $OCHF_2$, t-Bu, $SO_2Me$, $SO_2CF_3$, and $SO_3Me$.

In certain embodiments, with respect to formulae 4a-4-c, $R^5$ is Cl, F, Me, $CF_3$, or OMe.

In certain embodiments, with respect to formulae 1-4-c, $R^2$ is selected from H, Me, Et, n-Pr, t-Bu, $CF_3$, $CH_2OH$, $CH_2CH_2OH$, $CH_2CH_2OAc$, $CH_2(CH_2)_2OH$, $CH_2CH_2NHMe$, $CH_2NMe_2$, $CH_2CH_2NMe_2$, $CH_2CONH_2$, $CH_2CONMe_2$, $CH_2COOH$, $CH_2CH_2COOH$, $CH_2(CH_2)_2COOH$, $CH_2OMe$, and $CH_2CH_2OMe$.

In further embodiments, with respect to formulae 1-4-c, $R^2$ is selected from $CH_2NR^{2'}R^{2''}$, $CH_2CH_2NR^{2'}R^2$, $CH_2CH_2CH_2NR^{2'}R^{2''}$ and wherein $R^2$ and $R^{2''}$ can join together to form a heterocyclic ring.

In certain embodiments, with respect to formulae 1-4-c, $R^2$ is selected from cyclopropyl, cyclobutyl or cyclohexyl.

In particular embodiments, with respect to formulae 1-4-c, $R^2$ is Me or Et.

In more particular embodiments, with respect to formulae 1-4-c, $R^2$ is $CH_2OH$, or $CH_2CH_2OH$.

In certain embodiments, with respect to formulae 1-4-c, $R^3$ is H.

In certain embodiments, with respect to formulae 1-4-c, $R^3$ is selected from cyclopropyl, cyclobutyl or cyclohexyl.

In particular embodiments, with respect to formulae 1-4-c, $R^3$ is Me, Cl, F, or $CF_3$.

In more particular embodiments, with respect to formulae 1-4-c, $R^3$ is Cl.

In more particular embodiments, with respect to formula 1, the compound is according to formula 5a, 5b, or 5c:

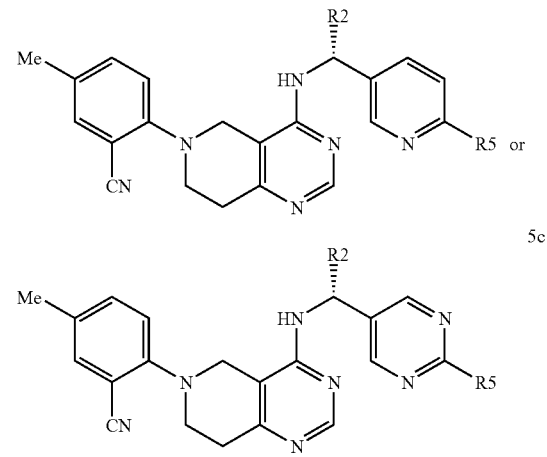

and wherein $R^2$ is as described for formula 1; and $R^5$ as described above.

In certain embodiments, with regard to formula 5a, 5b, or 5c, $R^2$ is H.

In certain embodiments, with regard to formula 5a, 5b, or 5c, $R^2$ is Me, Et or $CH_2OH$. In particular embodiments, $R^2$ is Me, $CH_2OH$, or $CH_2CH_2OH$.

In certain embodiments, with regard to formula 5a, 5b, or 5c, $R^5$ is H, Cl, F, Me, $CF_3$, or OMe. In particular embodiments, $R^5$ is Cl, F or $CF_3$, or OMe.

In certain embodiments, with respect to formulae 4a or 5a, the

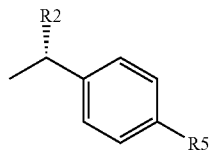

group is replaced with

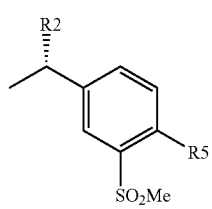

and wherein $R^5$ is H, Cl, Me or $CF_3$.

In certain embodiments, with respect to formulae 4a or 5a, the

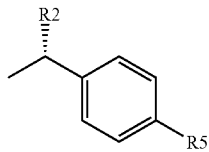

group is replaced with

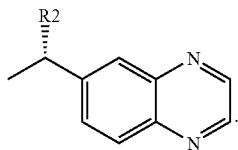

In certain embodiments, with respect to formulae 4a or 5a, the

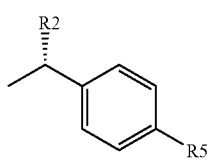

group is replaced with

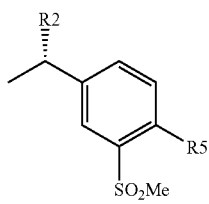

and wherein R⁵ is H, Cl, Me, OMe, or CF₃.

In certain embodiments, with respect to formulae 4a or 5a, the

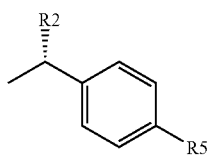

group is replaced with

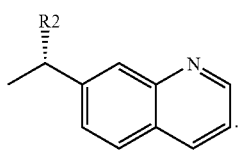

In certain embodiments, with respect to formulae 4a or 5a, the

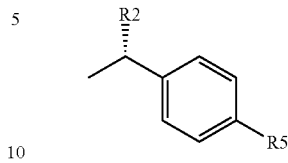

group is replaced with

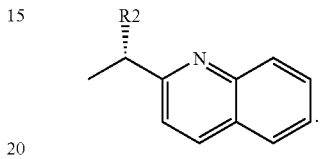

In certain embodiments, with respect to formulae 4a or 5a, the

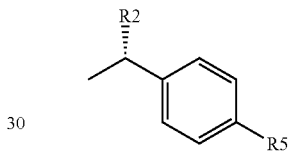

group is replaced with

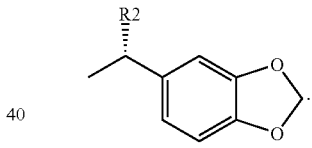

In certain embodiments, with respect to formulae 4a or 5a, the

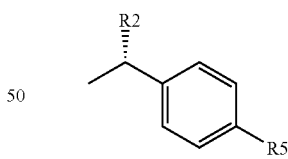

group is replaced with

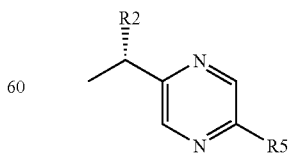

and wherein R⁵ is H, Cl, Me, OMe, or CF₃.

In certain embodiments, with respect to formulae 1-5c, R² is Me.

In certain embodiments, with respect to formulae 1-5c, $R^2$ is Et.

In certain embodiments, with respect to formulae 1-5c, $R^2$ is $CH_2OH$.

In certain embodiments, with respect to formulae 1-5c, $R^2$ is $CH_2CH_2OH$.

In certain embodiments, with respect to formulae 1-5c, $R^5$ is H.

In certain embodiments, with respect to formulae 1-5c, $R^5$ is Cl.

In certain embodiments, with respect to formulae 1-5c, $R^5$ is $CF_3$.

In certain embodiments, with respect to formulae 1-5c, $R^5$ is Me.

In certain embodiments, with respect to formulae 1-5c, $R^5$ is OMe.

In certain embodiments, when $R^3$, $R^4$ or $R^5$ is alkyl; the alkyl group is $C_1$-$C_8$alkyl. In another embodiment, the alkyl group is $C_1$-$C_6$alkyl. In a further embodiment, the alkyl group is $C_1$-$C_4$alkyl.

In one embodiment, the alkyl group is optionally substituted by one or more groups (such as 1 to 3 substituents, in particular one substituent group, which substituent group may be independently selected from halo, cyano, nitro, trifluoromethyl, trifluoromethoxy, azido, —$NR^{10}SO_2R^9$, —$SO_2NR^9R^{10}$, —C(O)$R^9$, —C(O)O$R^9$, —OC(O)$R^9$, —$NR^{10}C(O)R^9$, —C(O)$NR^9R^{10}$, —$NR^9R^{10}$, —$(CR^{10}R^{11})_m$O$R^{10}$ and wherein m is an integer from 1 to 5.

In one embodiment, each $R^9$ is independently selected from H, $C_1$-$C_8$alkyl, —$(CH_2)_t(C_6$-$C_{10}$ aryl), —$(CH_2)_t(C_5$-$C_{10}$ heteroaryl), —$(CH_2)_t(C_3$-$C_{10}$ cycloalkyl), and —$(CH_2)_t(C_5$-$C_{10}$ heterocycloalkyl), wherein t is an integer from 0 to 4.

In one embodiment, each $R^9$ is as described above, and any aryl, heteroaryl, cycloalkyl or heterocycloalkyl groups present, may themselves be substituted by $C_1$-$C_4$alkyl, halo, $C_1$-$C_4$alkoxy, $C_{1-4}$haloalkyl, $C_1$-$C_4$hydroxyalkyl, or $C_1$-$C_4$haloalkoxy or hydroxy.

In one embodiment, each $R^9$ is as described above, and each of $R^{10}$ and $R^{11}$ independently represents H or $C_1$-$C_6$alkyl.

In one embodiment, each $R^9$ is as described above and each of $R^{12}$ and $R^{13}$ independently represents H or $C_1$-$C_4$alkyl.

In one embodiment, each of $R^{10}$ and $R^{11}$ independently represents H or $C_1$-$C_6$alkyl.

In one embodiment, each $R^9$ is other than H.

In certain embodiments, when $R^3$, $R^4$ or $R^5$ is alkoxy; the alkoxy group is —O$R^9$; and $R^9$ is as described in the above embodiments; provided that $R^9$ is other than H.

In certain embodiments, when $R^3$, $R^4$ or $R^5$ is acyl; the acyl group is —C(O)$R^9$; and $R^9$ is as described in the above embodiments.

In certain embodiments, when $R^3$, $R^4$ or $R^5$ is alkoxycarbonyl; the alkoxycarbonyl group is —C(O)O$R^9$; and $R^9$ is as described in the above embodiments; provided that $R^9$ is other than H In certain embodiments, when $R^3$, $R^4$ or $R^5$ is acylamino; the acylamino group is —$NR^{10}C(O)R^9$; and $R^9$ and $R^{10}$ are as described in the above embodiments; provided that $R^9$ is other than H In certain embodiments, when $R^3$, $R^4$ or $R^5$ is acyloxy; the acyloxy group is —OC(O)$R^9$; and $R^9$ is as described in the above embodiments; provided that $R^9$ is other than H.

In certain embodiments, when $R^3$, $R^4$ or $R^5$ is sulfo; the sulfo group is —$SO_3R^9$; and $R^9$ is as described in the above embodiments.

In certain embodiments, when $R^3$, $R^4$ or $R^5$ is sulfonyl; the sulfonyl group is —$SO_2R^9$; and $R^9$ is as described in the above embodiments; provided that $R^9$ is other than H.

In certain embodiments, when $R^3$, $R^4$ or $R^5$ is sulfinyl; the sulfinyl group is —SO$R^9$; and $R^9$ is as described in the above embodiments; provided that $R^9$ is other than H In certain embodiments, when $R^3$, $R^4$ or $R^5$ is aminosulfonyl; the aminosulfonyl group is —$SO_2NR^9R^{10}$; and $R^9$ and $R^{10}$ are as described in the above embodiments In certain embodiments, when $R^3$, $R^4$ or $R^5$ is amino; the amino group is —$NR^9R^{10}$; and $R^9$ and $R^{10}$ are as described in the above embodiments In certain embodiments, when $R^3$, $R^4$ or $R^5$ is carbamoyl; the carbamoyl group is —$CO_2NR^9R^{10}$; and $R^9$ and $R^{10}$ are as described in the above embodiments In certain embodiments, when $R^3$, $R^4$ or $R^5$ is alkylthio; the alkylthio group is —S$R^9$; and $R^9$ is as described in the above embodiments; provided that $R^9$ is other than H.

With regard to formula 1, in certain embodiments, the compound is selected from the group consisting of 5-Methyl-2-{4-[(6-trifluoromethyl-pyridin-3-ylmethyl)-amino]-7,8-dihydro-5H-pyrido[4,3-d]pyrimidin-6-yl}-benzonitrile;

5-Bromo-2-{4-[(6-trifluoromethyl-pyridin-3-ylmethyl)-amino]-7,8-dihydro-5H-pyrido[4,3-d]pyrimidin-6-yl}-benzonitrile;

5-Cyclopropyl-2-{4-[(6-trifluoromethyl-pyridin-3-ylmethyl)-amino]-7,8-dihydro-5H-pyrido[4,3-d]pyrimidin-6-yl}-benzonitrile;

5-Chloro-2-{4-[(6-trifluoromethyl-pyridin-3-ylmethyl)-amino]-7,8-dihydro-5H-pyrido[4,3-d]pyrimidin-6-yl}-benzonitrile;

5-Trifluoromethyl-2-{4-[(6-trifluoromethyl-pyridin-3-ylmethyl)-amino]-7,8-dihydro-5H-pyrido[4,3-d]pyrimidin-6-yl}-benzonitrile;

5-Bromo-2-{4-[(R)-1-(6-trifluoromethyl-pyridin-3-yl)-ethylamino]-7,8-dihydro-5H-pyrido[4,3-d]pyrimidin-6-yl}-benzonitrile;

5-Methyl-2-{4-[(R)-1-(6-trifluoromethyl-pyridin-3-yl)-ethylamino]-7,8-dihydro-5H-pyrido[4,3-d]pyrimidin-6-yl}-benzonitrile;

5-Chloro-2-{4-[(R)-1-(6-trifluoromethyl-pyridin-3-yl)-ethylamino]-7,8-dihydro-5H-pyrido[4,3-d]pyrimidin-6-yl}-benzonitrile;

5-Fluoro-2-{4-[(6-trifluoromethyl-pyridin-3-ylmethyl)-amino]-7,8-dihydro-5H-pyrido[4,3-d]pyrimidin-6-yl}-benzonitrile;

2-{4-[(6-Trifluoromethyl-pyridin-3-ylmethyl)-amino]-7,8-dihydro-5H-pyrido[4,3-d]pyrimidin-6-yl}-benzonitrile;

5-Chloro-2-{4-[(2-methyl-6-trifluoromethyl-pyridin-3-ylmethyl)-amino]-7,8-dihydro-5H-pyrido[4,3-d]pyrimidin-6-yl}-benzonitrile;

5-Chloro-2-{4-[(6-dimethylamino-pyridin-3-ylmethyl)-amino]-7,8-dihydro-5H-pyrido[4,3-d]pyrimidin-6-yl}-benzonitrile;

5-Chloro-2-{4-[(6-methoxy-pyridin-3-ylmethyl)-amino]-7,8-dihydro-5H-pyrido[4,3-d]pyrimidin-6-yl}-benzonitrile;

5-Bromo-2-{4-[(6-methoxy-pyridin-3-ylmethyl)-amino]-7,8-dihydro-5H-pyrido[4,3-d]pyrimidin-6-yl}-benzonitrile;

2-{4-[(6-Methoxy-pyridin-3-ylmethyl)-amino]-7,8-dihydro-5H-pyrido[4,3-d]pyrimidin-6-yl}-5-methyl-benzonitrile;

5-Chloro-2-{4-[(3-chloro-5-trifluoromethyl-pyridin-2-ylmethyl)-amino]-7,8-dihydro-5H-pyrido[4,3-d]pyrimidin-6-yl}-benzonitrile;

5-Chloro-2-{4-[(5-trifluoromethyl-pyridin-2-ylmethyl)-amino]-7,8-dihydro-5H-pyrido[4,3-d]pyrimidin-6-yl}-benzonitrile;

(R)-3-[6-(4-Chloro-2-cyano-phenyl)-5,6,7,8-tetrahydro-pyrido[4,3-d]pyrimidin-4-ylamino]-3-(6-methoxy-pyridin-3-yl)-propionic acid tert-butyl ester;

(R)-3-[6-(4-Chloro-2-cyano-phenyl)-5,6,7,8-tetrahydro-pyrido[4,3-d]pyrimidin-4-ylamino]-3-(6-methoxy-pyridin-3-yl)-propionic acid;

5-Chloro-2-{4-[(R)-3-hydroxy-1-(6-trifluoromethyl-pyridin-3-yl)-propylamino]-7,8-dihydro-5H-pyrido[4,3-d]pyrimidin-6-yl}-benzonitrile;

2-{4-[(R)-3-Hydroxy-1-(6-methyl-pyridin-3-yl)-propylamino]-7,8-dihydro-5H-pyrido[4,3-d]pyrimidin-6-yl}-5-methyl-benzonitrile;

2-{4-[(R)-1-(6-Difluoromethyl-pyridin-3-yl)-3-hydroxy-propylamino]-7,8-dihydro-5H-pyrido[4,3-d]pyrimidin-6-yl}-5-methyl-benzonitrile;

2-{4-[(S)-2-Hydroxy-1-(6-methoxy-pyridin-3-yl)-ethylamino]-7,8-dihydro-5H-pyrido[4,3-d]pyrimidin-6-yl}-5-methyl-benzonitrile;

2-{4-[(R)-3-Hydroxy-1-(6-methoxy-pyridin-3-yl)-propylamino]-7,8-dihydro-5H-pyrido[4,3-d]pyrimidin-6-yl}-5-methyl-benzonitrile;

2-{4-[3-Hydroxy-1-(6-trifluoromethyl-pyridin-3-yl)-propylamino]-7,8-dihydro-5H-pyrido[4,3-d]pyrimidin-6-yl}-5-methyl-benzonitrile;

2-{4-[(S)-2-Methoxy-1-(6-methoxy-pyridin-3-yl)-ethylamino]-7,8-dihydro-5H-pyrido[4,3-d]pyrimidin-6-yl}-5-methyl-benzonitrile;

2-{4-[(6-Chloro-pyridin-3-ylmethyl)-amino]-7,8-dihydro-5H-pyrido[4,3-d]pyrimidin-6-yl}-5-methyl-benzonitrile;

2-{4-[(5-Chloro-pyridin-2-ylmethyl)-amino]-7,8-dihydro-5H-pyrido[4,3-d]pyrimidin-6-yl}-5-methyl-benzonitrile;

5-Methyl-2-{4-[(pyridin-2-ylmethyl)-amino]-7,8-dihydro-5H-pyrido[4,3-d]pyrimidin-6-yl}-benzonitrile;

2-{4-[(5-Cyclopropyl-pyridin-2-ylmethyl)-amino]-7,8-dihydro-5H-pyrido[4,3-d]pyrimidin-6-yl}-5-methyl-benzonitrile;

2-{4-[(4-Amino-2-methyl-pyrimidin-5-ylmethyl)-amino]-7,8-dihydro-5H-pyrido[4,3-d]pyrimidin-6-yl}-5-methyl-benzonitrile;

2-{4-[(3,5-Dichloro-pyridin-2-ylmethyl)-amino]-7,8-dihydro-5H-pyrido[4,3-d]pyrimidin-6-yl}-5-methyl-benzonitrile;

2-{4-[(6-Ethyl-pyridin-3-ylmethyl)-amino]-7,8-dihydro-5H-pyrido[4,3-d]pyrimidin-6-yl}-5-methyl-benzonitrile;

5-Chloro-2-{4-[(R)-3-hydroxy-1-(6-methoxy-pyridin-3-yl)-propylamino]-7,8-dihydro-5H-pyrido[4,3-d]pyrimidin-6-yl}-benzonitrile;

5-Chloro-2-{4-[(S)-2-hydroxy-1-(6-methoxy-pyridin-3-yl)-ethylamino]-7,8-dihydro-5H-pyrido[4,3-d]pyrimidin-6-yl}-benzonitrile;

2-[4-(3-Cyano-benzylamino)-7,8-dihydro-5H-pyrido[4,3-d]pyrimidin-6-yl]-5-methyl-benzonitrile;

2-{4-[(Imidazo[1,2-a]pyridin-7-ylmethyl)-amino]-7,8-dihydro-5H-pyrido[4,3-d]pyrimidin-6-yl}-5-methyl-benzonitrile;

2-{4-[(Benzooxazol-5-ylmethyl)-amino]-7,8-dihydro-5H-pyrido[4,3-d]pyrimidin-6-yl}-5-methyl-benzonitrile;

5-Methyl-2-{4-[(2-methyl-pyrimidin-5-ylmethyl)-amino]-7,8-dihydro-5H-pyrido[4,3-d]pyrimidin-6-yl}-benzonitrile;

5-Methyl-2-[4-(4-methyl-3-[1,2,4]triazol-1-yl-benzylamino)-7,8-dihydro-5H-pyrido[4,3-d]pyrimidin-6-yl]-benzonitrile;

(R)-3-[6-(2-Cyano-4-methyl-phenyl)-5,6,7,8-tetrahydro-pyrido[4,3-d]pyrimidin-4-ylamino]-3-(6-methoxy-pyridin-3-yl)-propionic acid;

(R)-3-[6-(2-Cyano-4-methyl-phenyl)-5,6,7,8-tetrahydro-pyrido[4,3-d]pyrimidin-4-ylamino]-3-(6-methoxy-pyridin-3-yl)-propionamide;

(R)-3-[6-(2-Cyano-4-methyl-phenyl)-5,6,7,8-tetrahydro-pyrido[4,3-d]pyrimidin-4-ylamino]-3-(6-methoxy-pyridin-3-yl)-N,N-dimethyl-propionamide;

5-Chloro-2-{4-[(imidazo[1,2-a]pyridin-7-ylmethyl)-amino]-7,8-dihydro-5H-pyrido[4,3-d]pyrimidin-6-yl}-benzonitrile;

5-Chloro-2-{4-[(2-methyl-pyrimidin-1-ylmethyl)-amino]-7,8-dihydro-5H-pyrido[4,3-d]pyrimidin-6-yl}-benzonitrile;

2-{4-[(S)-2-Hydroxy-1-(6-trifluoromethyl-pyridin-3-yl)-ethylamino]-7,8-dihydro-5H-pyrido[4,3-d]pyrimidin-6-yl}-5-methyl-benzonitrile;

5-Chloro-2-{4-[(S)-2-hydroxy-1-(6-trifluoromethyl-pyridin-3-yl)-ethylamino]-7,8-dihydro-5H-pyrido[4,3-d]pyrimidin-6-yl}-benzonitrile;

2-[4-(3-Fluoro-4-methyl-benzylamino)-7,8-dihydro-5H-pyrido[4,3-d]pyrimidin-6-yl]-5-methyl-benzonitrile;

5-Methyl-2-[4-(4-methyl-3-methylsulfanyl-benzylamino)-7,8-dihydro-5H-pyrido[4,3-d]pyrimidin-6-yl]-benzonitrile;

2-[4-(4-Chloro-3-[1,2,4]triazol-4-yl-benzylamino)-7,8-dihydro-5H-pyrido[4,3-d]pyrimidin-6-yl]-5-methyl-benzonitrile;

5-Chloro-2-[4-(3-[1,2,4]triazol-4-yl-benzylamino)-7,8-dihydro-1H-pyrido[4,3-d]pyrimidin-6-yl]-benzonitrile;

5-Chloro-2-[4-(4-chloro-3-[1,2,4]triazol-4-yl-benzylamino)-7,8-dihydro-5H-pyrido[4,3-d]pyrimidin-6-yl]-benzonitrile;

5-Methyl-2-[4-(3-[1,2,4]triazol-4-yl-benzylamino)-7,8-dihydro-5H-pyrido[4,3-d]pyrimidin-6-yl]-benzonitrile;

2-{4-[(4-Amino-2-methoxy-pyrimidin-5-ylmethyl)-amino]-7,8-dihydro-5H-pyrido[4,3-d]pyrimidin-6-yl}-5-methyl-benzonitrile;

2-[4-(3-Iodo-4-methyl-benzylamino)-7,8-dihydro-5H-pyrido[4,3-d]pyrimidin-6-yl]-5-methyl-benzonitrile;

5-Chloro-2-{4-[(R)-1-(2-methoxy-pyrimidin-5-yl)-ethylamino]-7,8-dihydro-5H-pyrido[4,3-d]pyrimidin-6-yl}-benzonitrile;

2-{4-[(R)-1-(2-Methoxy-pyrimidin-5-yl)-ethylamino]-7,8-dihydro-5H-pyrido[4,3-d]pyrimidin-6-yl}-5-methyl-benzonitrile;

2-[4-(3-Methanesulfonyl-4-methyl-benzylamino)-7,8-dihydro-5H-pyrido[4,3-d]pyrimidin-6-yl]-5-methyl-benzonitrile;

2-{4-[(S)-2-Hydroxy-1-(2-methoxy-pyrimidin-5-yl)-ethylamino]-7,8-dihydro-5H-pyrido[4,3-d]pyrimidin-6-yl}-5-methyl-benzonitrile;

2-{4-[(2-Isopropyl-pyridin-5-ylmethyl)-amino]-7,8-dihydro-5H-pyrido[4,3-d]pyrimidin-6-yl}-5-methyl-benzonitrile;

5-Chloro-2-{4-[(R)-1-(6-difluoromethyl-pyridin-3-yl)-3-hydroxy-propylamino]-7,8-dihydro-5H-pyrido[4,3-d]pyrimidin-6-yl}-benzonitrile;

5-Methyl-2-[4-(4-methyl-3-morpholin-4-yl-benzylamino)-7,8-dihydro-5H-pyrido[4,3-d]pyrimidin-6-yl]-benzonitrile;

2-{4-[(R)-3-Hydroxy-1-(6-trifluoromethyl-pyridin-3-yl)-propylamino]-7,8-dihydro-5H-pyrido[4,3-d]pyrimidin-6-yl}-5-methyl-benzonitrile;

2-{4-[(S)-3-Hydroxy-1-(6-trifluoromethyl-pyridin-3-yl)-propylamino]-7,8-dihydro-5H-pyrido[4,3-d]pyrimidin-6-yl}-5-methyl-benzonitrile;

5-Methyl-2-{4-[(R)-1-(2-methyl-pyrimidin-5-yl)-ethylamino]-7,8-dihydro-5H-pyrido[4,3-d]pyrimidin-6-yl}-benzonitrile;
5-Methyl-2-{4-[(S)-1-(2-methyl-pyrimidin-5-yl)-ethylamino]-7,8-dihydro-5H-pyrido[4,3-d]pyrimidin-6-yl}-benzonitrile;
2-{4-[(2-Methoxy-pyrimidin-5-ylmethyl)-amino]-7,8-dihydro-5H-pyrido[4,3-d]pyrimidin-6-yl}-5-methyl-benzonitrile;
5-Chloro-2-{4-[(2-methoxy-pyrimidin-5-ylmethyl)-amino]-7,8-dihydro-5H-pyrido[4,3-d]pyrimidin-6-yl}-benzonitrile;
2-{4-[(S)-1-(6-Difluoromethyl-pyridin-3-yl)-2-hydroxy-ethylamino]-7,8-dihydro-5H-pyrido[4,3-d]pyrimidin-6-yl}-5-methyl-benzonitrile;
2-[4-(4-Chloro-3-methanesulfonyl-benzylamino)-7,8-dihydro-5H-pyrido[4,3-d]pyrimidin-6-yl]-5-methyl-benzonitrile;
5-Chloro-2-{4-[(S)-1-(6-difluoromethyl-pyridin-3-yl)-2-hydroxy-ethylamino]-7,8-dihydro-5H-pyrido[4,3-d]pyrimidin-6-yl}-benzonitrile;
5-Chloro-2-{4-[(S)-2-hydroxy-1-(2-methyl-pyrimidin-5-yl)-ethylamino]-7,8-dihydro-5H-pyrido[4,3-d]pyrimidin-6-yl}-benzonitrile;
2-{4-[(S)-2-Hydroxy-1-(2-methyl-pyrimidin-5-yl)-ethylamino]-7,8-dihydro-5H-pyrido[4,3-d]pyrimidin-6-yl}-5-methyl-benzonitrile;
5-Chloro-2-{4-[(R)-1-(2-methyl-pyrimidin-5-yl)-ethylamino]-7,8-dihydro-5H-pyrido[4,3-d]pyrimidin-6-yl}-benzonitrile;
5-Chloro-2-[4-(3-methanesulfonyl-4-methyl-benzylamino)-7,8-dihydro-5H-pyrido[4,3-d]pyrimidin-6-yl]-benzonitrile;
Acetic acid (R)-3-[6-(2-cyano-4-methyl-phenyl)-5,6,7,8-tetrahydro-pyrido[4,3-d]pyrimidin-4-ylamino]-3-(6-trifluoromethyl-pyridin-3-yl)-propyl ester;
5-Chloro-2-{4-[(S)-2-hydroxy-1-(2-methoxy-pyrimidin-5-yl)-ethylamino]-7,8-dihydro-5H-pyrido[4,3-d]pyrimidin-6-yl}-benzonitrile;
5-Methyl-2-{4-[(quinoxalin-6-ylmethyl)-amino]-7,8-dihydro-5H-pyrido[4,3-d]pyrimidin-6-yl}-benzonitrile;
5-Methyl-2-{4-[(quinolin-2-ylmethyl)-amino]-7,8-dihydro-5H-pyrido[4,3-d]pyrimidin-6-yl}-benzonitrile;
2-{4-[(1H-Indol-6-ylmethyl)-amino]-7,8-dihydro-5H-pyrido[4,3-d]pyrimidin-6-yl}-5-methyl-benzonitrile;
2-{4-[(Benzo[1,3]dioxol-5-ylmethyl)-amino]-7,8-dihydro-5H-pyrido[4,3-d]pyrimidin-6-yl}-5-methyl-benzonitrile;
2-[4-(1-Benzo[1,3]dioxol-5-yl-ethylamino)-7,8-dihydro-5H-pyrido[4,3-d]pyrimidin-6-yl]-5-methyl-benzonitrile;
5-Chloro-2-{4-[(quinoxalin-6-ylmethyl)-amino]-7,8-dihydro-5H-pyrido[4,3-d]pyrimidin-6-yl}-benzonitrile;
5-Methyl-2-[4-(1-pyrazin-2-yl-ethylamino)-7,8-dihydro-5H-pyrido[4,3-d]pyrimidin-6-yl]-benzonitrile;
5-Methyl-2-[4-(1-quinoxalin-6-yl-ethylamino)-7,8-dihydro-5H-pyrido[4,3-d]pyrimidin-6-yl]-benzonitrile;
2-{4-[(S)-1-(2-Methoxy-pyrimidin-5-yl)-ethylamino]-7,8-dihydro-5H-pyrido[4,3-d]pyrimidin-6-yl}-5-methyl-benzonitrile;
2-{4-[1-(4-Chloro-3-methanesulfonyl-phenyl)-ethylamino]-7,8-dihydro-5H-pyrido[4,3-d]pyrimidin-6-yl}-5-methyl-benzonitrile;
2-[4-((R)-1-Benzo[1,3]dioxol-5-yl-ethylamino)-7,8-dihydro-5H-pyrido[4,3-d]pyrimidin-6-yl]-5-methyl-benzonitrile;
2-[4-((S)-1-Benzo[1,3]dioxol-5-yl-ethylamino)-7,8-dihydro-5H-pyrido[4,3-d]pyrimidin-6-yl]-5-methyl-benzonitrile;
2-{4-[1-(3-Methanesulfonyl-4-methyl-phenyl)-ethylamino]-7,8-dihydro-H-pyrido[4,3-d]pyrimidin-6-yl}-5-methyl-benzonitrile;
5-Methyl-2-{4-[(quinolin-7-ylmethyl)-amino]-7,8-dihydro-5H-pyrido[4,3-d]pyrimidin-6-yl}-benzonitrile;
2-{4-[(R)-1-(4-Chloro-3-methanesulfonyl-phenyl)-ethylamino]-7,8-dihydro-5H-pyrido[4,3-d]pyrimidin-6-yl}-5-methyl-benzonitrile;
2-{4-[(S)-1-(4-Chloro-3-methanesulfonyl-phenyl)-ethylamino]-7,8-dihydro-5H-pyrido[4,3-d]pyrimidin-6-yl}-5-methyl-benzonitrile;
5-Methyl-2-[4-((R)-1-quinoxalin-6-yl-ethylamino)-7,8-dihydro-5H-pyrido[4,3-d]pyrimidin-6-yl]-benzonitrile; and
5-Methyl-2-[4-((S)-1-quinoxalin-6-yl-ethylamino)-7,8-dihydro-5H-pyrido[4,3-d]pyrimidin-6-yl]-benzonitrile;

Additional embodiments within the scope provided herein are set forth in non-limiting fashion elsewhere herein and in the examples. It should be understood that these examples are for illustrative purposes only and are not to be construed as limiting in any manner.

In certain aspects, provided herein are prodrugs and derivatives of the compounds according to the formulae above. Prodrugs are derivatives of the compounds provided herein, which have metabolically cleavable groups and become by solvolysis or under physiological conditions the compounds provided herein, which are pharmaceutically active, in vivo. Such examples include, but are not limited to, choline ester derivatives and the like, N-alkylmorpholine esters and the like.

Certain compounds provided herein have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

Pharmaceutical Compositions

When employed as pharmaceuticals, the fused heterocyclic compounds provided herein are typically administered in the form of a pharmaceutical composition. Such compositions can be prepared in a manner well known in the pharmaceutical art and comprise at least one active compound.

Generally, the compounds provided herein are administered in a therapeutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The above-described components for orally administrable, injectable or topically administrable compositions are merely representative. Other materials as well as processing techniques and the like are set forth in Part 8 of Remington's The Science and Practice of Pharmacy, 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in Remington's Pharmaceutical Sciences.

The following formulation examples illustrate representative pharmaceutical compositions of this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active amide compound per capsule).

Formulation 3

Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4

Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5

Injection

A compound of the invention is dissolved or suspended in a buffered sterile saline injectable aqueous medium to a concentration of approximately 5 mg/ml.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present fused heterocyclic compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans. Thus, and as stated earlier, the present invention includes within its scope, and extends to, the recited methods of treatment, as well as to the compounds for such methods, and for the preparation of medicaments useful for such methods.

In a method of treatment aspect, provided herein is a method of treating a mammal susceptible to or afflicted with a condition associated with arthritis, asthma, myocardial infarction, inflammatory bowel disease and autoimmune disorders, which method comprises administering an effective amount of one or more of the pharmaceutical compositions just described.

In yet another method of treatment aspect, provided herein is a method of treating a mammal susceptible to or afflicted with a condition that gives rise to pain responses or that relates to imbalances in the maintenance of basal activity of sensory nerves. The present compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflux disease, irritable bowel syndrome, inflammatory bowel disease, pancreatitis, and various gynecological and urological disorders), dental pain and headache (such as migraine, cluster headache and tension headache).

In additional method of treatment aspects, provided herein are methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders; itch/pruritus such as, for example psoriasis; obesity; lipid disorders; cancer; and renal disorders method comprises administering an effective condition-treating or condition-preventing amount of one or more of the pharmaceutical compositions just described.

As a further aspect there is provided the present fused heterocyclic compounds for use as a pharmaceutical especially in the treatment or prevention of the aforementioned conditions and diseases. We also provide the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds provided herein will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds provided herein can be administered as the sole active agent or they can be administered in combination with other agents, including other active amines and derivatives. Administration in combination can proceed by any technique apparent to those of skill in the art including, for example, separate, sequential, concurrent and alternating administration.

General Synthetic Procedures

The fused heterocyclic compounds provided herein can be prepared from readily available starting materials using the following general methods and procedures. See, e.g., FIG. 1 and Synthetic Schemes 1 and 2, below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein, for example, may be prepared by the reaction of a chloro derivative with an appropriately substituted amine and the product isolated and purified by known standard procedures. Such procedures include (but are not limited to) recrystallization, column chromatography or HPLC. The following schemes are presented with details as to the preparation of representative fused heterocyclics that have been listed hereinabove. The compounds provided herein may be prepared from known or commercially available starting materials and reagents by one skilled in the art of organic synthesis.

The enantiomerically pure compounds provided herein may be prepared according to any techniques known to those of skill in the art. For instance, they may be prepared by chiral or asymmetric synthesis from a suitable optically pure precursor or obtained from a racemate by any conventional technique, for example, by chromatographic resolution using a chiral column, TLC or by the preparation of diastereoisomers, separation thereof and regeneration of the desired enantiomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, N.Y., 1962); and S. H. Wilen *Tables of Resolving Agents and Optical Resolutions* 268 (E. L. Eliel ed., Univ. of Notre Dame Press, Notre Dame, 1N, 1972, *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.).

In certain embodiments, an enantiomerically pure compound of formula 1 may be obtained by reaction of the racemate with a suitable optically active acid or base. Suitable acids or bases include those described in Bighley et al., 1995, *Salt Forms of Drugs and Adsorption*, in *Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties.

Enantiomerically pure compounds can also be recovered either from the crystallized diastereomer or from the mother liquor, depending on the solubility properties of the particular acid resolving agent employed and the particular acid enantiomer used. The identity and optical purity of the particular compound so recovered can be determined by polarimetry or other analytical methods known in the art. The diastereoisomers can then be separated, for example, by chromatography or fractional crystallization, and the desired enantiomer regenerated by treatment with an appropriate base or acid. The other enantiomer may be obtained from the racemate in a similar manner or worked up from the liquors of the first separation.

In certain embodiments, enantiomerically pure compound can be separated from racemic compound by chiral chromatography. Various chiral columns and eluents for use in the separation of the enantiomers are available and suitable conditions for the separation can be empirically determined by methods known to one of skill in the art. Exemplary chiral columns available for use in the separation of the enantiomers provided herein include, but are not limited to CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Synthetic Scheme 1: General Synthesis of N-Substituted 2-(4-(amino)-7,8-dihydropyrido[4,3-d] pyrimidin-6(5H)-yl)benzonitriles

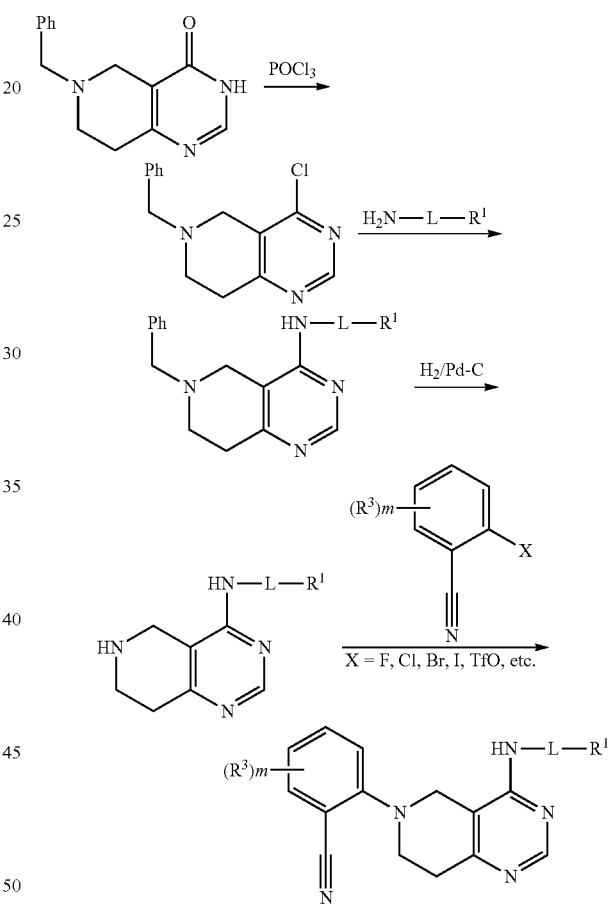

L = R² substituted methylene and R¹ = substituted or unsubstituted cycloalkyl, cycloheteroalkyl, aryl or heteroaryl group.

Substituted 2-(4-(alkylamino)-7,8-dihydropyrido[4,3-d]pyrimidin-6(5H)-yl)benzonitrile derivative is prepared by first reacting the 6-benzyl-5,6,7,8-tetrahydro-3H-pyrido[4,3-d]pyrimidin-4-one with POCl₃ and reacting the product with an appropriately substituted amine to give N-substituted 6-benzyl-5,6,7,8-tetrahydropyrido[4,3-d]pyrimidin-4-amine which is subjected to removal of the benzyl group followed by condensation with an appropriate 2-halo-benzonitrile using $S_NAR$ or Buchwald coupling reaction to yield the appropriate N-substituted 2-(4-amino-7,8-dihydro-5H-pyrido[4,3-d]pyrimidin-6-yl)-benzonitrile. The general synthesis method is depicted in Scheme 1.

Synthetic Scheme 2: Alternate Synthesis of N-Substituted 2-(4-amino-7,8-dihydropyrido[4,3-d] pyrimidin-6(5H)-yl)benzonitriles

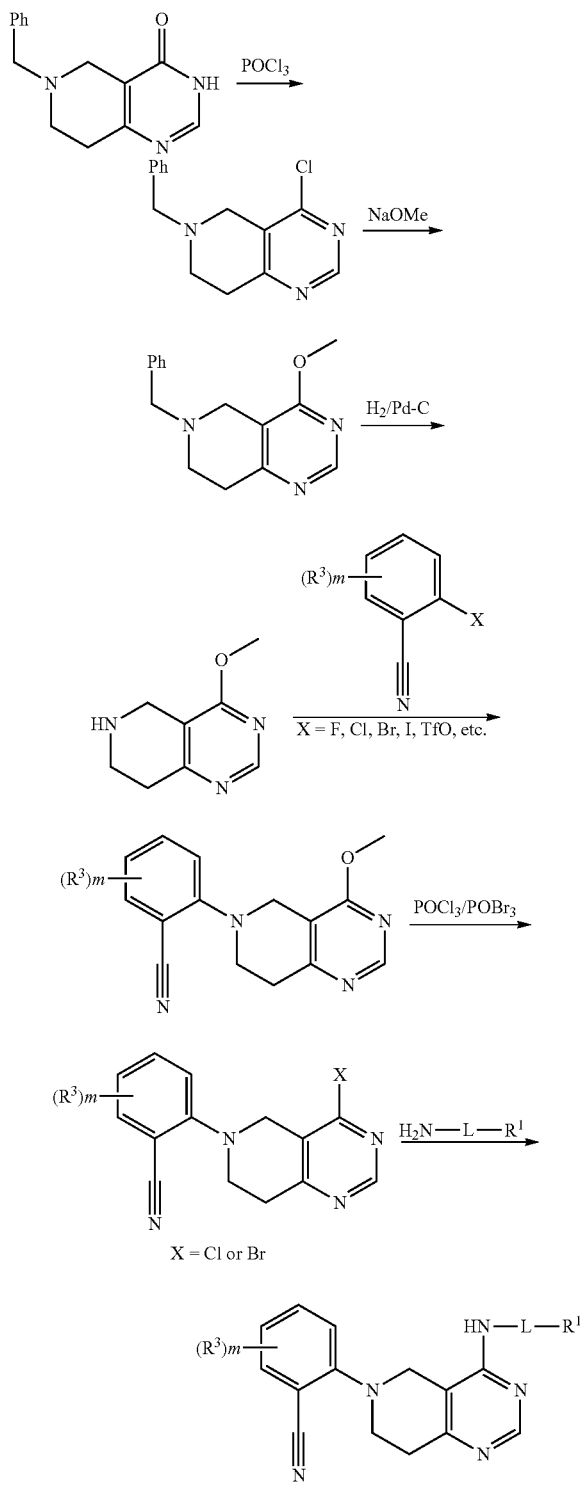

L = R² substituted methylene and R¹ = substituted or unsubstituted cycloalkyl, cycloheteroalkyl, aryl or heteroaryl group.

Various N-substituted 2-(4-amino-7,8-dihydropyrido[4,3-d]pyrimidin-6(5H)-yl)benzonitriles are prepared using a general procedure shown above (Scheme 2). 6-Benzyl-5,6,7,8-tetrahydropyrido[4,3-d]pyrimidin-4(3H)-one is treated with POCl₃ to give 6-benzyl-4-chloro-5,6,7,8-tetrahydropyrido[4, 3-d]pyrimidine which is treated with sodium methoxide to give 6-benzyl-4-methoxy-5,6,7,8-tetrahydropyrido[4,3-d] pyrimidine. Debenzylation and reacting the product with an appropriate 2-halo-benzonitrile under S$_N$AR or Buchwald coupling reaction conditions give the 2-(4-methoxy-7,8-dihydropyrido[4,3-d]pyrimidin-6(5H)-yl)benzonitrile which is reacted with POCl₃ or POBr₃. Displacement of the resultant 4-chloro or 4-bromo group using appropriately substituted amines via S$_N$AR displacement affords various N-substituted 2-(4-amino-7,8-dihydropyrido[4,3-d]pyrimidin-6(5H)-yl) benzonitriles.

The following synthetic and biological examples are offered to illustrate the compounds, pharmaceutical compositions and methods provided herein and are not to be construed in any way as limiting the scope provided herein. In the examples below, all temperatures are in degrees Celsius (unless otherwise indicated). The syntheses of these representative compounds are carried out in accordance with the methods set forth above and using the appropriate reagents, starting materials, and purification methods known to those skilled in the art.

Exemplary Compounds Provided Herein

The following compounds can be prepared according to the methods provided herein. Unless otherwise indicated, reactions in microwave were carried out in Biotage Initiator microwave synthesizer manufactured by Biotage AB, Inc. or Emrys Optimizer microwave model manufactured by Personal Chemistry, Inc.

Synthesis of Intermediates

Intermediate 1

6-Benzyl-5,6,7,8-tetrahydropyrido[4,3-d]pyrimidin-4 (3H)-one

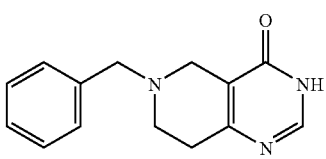

A mixture of ethyl 1-benzyl-4-oxopiperidine-3-carboxylate hydrochloride (50.0 g, 0.168 mol), formamidine acetate (16.2 g, 0.201 mol), 4.37 M of sodium methoxide in methanol (190 mL) and methanol (200 mL) was heated at 85° C. for 16 hour in a 350 mL sealed reaction vessel. The mixture was allowed to cool and concentrated in vacuo. The residue was dissolved in 1N NaOH (150 mL) and poured over ice. Glacial acetic acid was added to the mixture until the pH of the mixture was 7 and a tan solid precipitated out. The solid was filtered, washed with water and cold ether, and dried on high vacuum to yield the title compound as a tan solid (26.2 g, 61.4%).

LC-MS: 242.2 [M+1]⁺; ¹H NMR (400 MHz, DMSO-d6): δ 2.29 (t, 2H, J=5.8 Hz), 2.61 (t, 2H, J=5.8 Hz), 3.26 (s, 2H), 3.64 (s, 2H), 7.21-7.36 (m, 6H), 7.96 (s, 1H).

Intermediate 2

6-Benzyl-4-chloro-5,6,7,8-tetrahydropyrido[4,3-d]pyrimidine

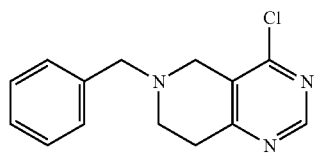

A mixture of 6-benzyl-5,6,7,8-tetrahydropyrido[4,3-d]pyrimidin-4(3H)-one (5.0 g, 0.02 mol), phosphoryl chloride (3.30 mL, 0.035 mol) and acetonitrile (80 mL) and DMF (catalytic amount) was heated at 70° C. for 1 hour. The mixture was concentrated in vacuo and the remaining black residue was taken up in dichloromethane (250 mL) and poured over ice. The mixture was carefully neutralized with the addition of solid sodium bicarbonate. The organic layer was separated and dried over sodium sulfate and concentrated in vacuo. The mixture was purified by silica gel column with EtOAc/hexane (0-100%) to yield the title compound as a yellow oil (3 g, 57.8%). LC-MS: 260 [M+1]⁺; ¹H NMR (400 MHz, DMSO-d6): δ 8.80 (s, 1H), 7.40-7.24 (m, 5H), 3.76 (s, 2H), 3.57 (s, 2H), 2.92 (t, 2H), 2.80 (t, 2H).

Intermediate 3

4-Methoxy-5,6,7,8-tetrahydropyrido[4,3-d]pyrimidine

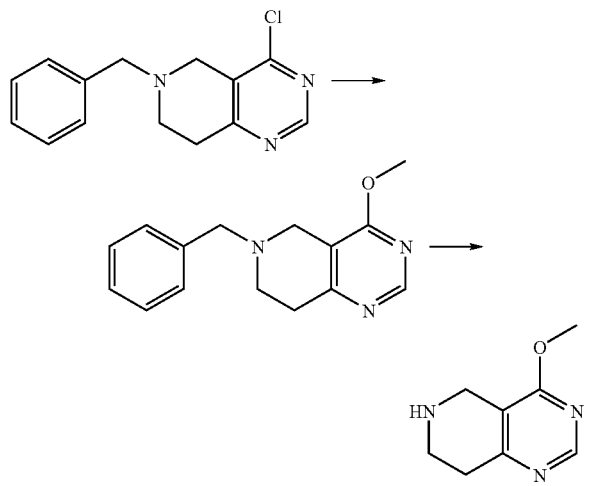

A) 6-Benzyl-4-methoxy-5,6,7,8-tetrahydropyrido[4,3-d]pyrimidine

A 1 L flask was charged with 6-benzyl-4-chloro-5,6,7,8-tetrahydropyrido[4,3-d]pyrimidine (39.6 g, 0.152 mol) and methanol (300 mL), and the mixture was heated to dissolve the chloropyrimidine. 4.37 M of sodium methoxide in methanol (105 mL) was added slowly to the warm mixture and the stirred mixture rapidly turned cloudy. The resultant suspension was heated under reflux for 2 h. After cooling, the mixture was concentrated in vacuo to ca 100 mL. The residue was poured into water (600 mL), and extracted with CH₂Cl₂ (200 mL×2). The combined organic layers were washed with brine (400 mL), dried (Na₂SO₄), filtered and concentrated in vacuo to yield a light brown oil (38.9 g, 100%).
LC-MS: 256.1 M+H]⁺

B) 4-Methoxy-5,6,7,8-tetrahydropyrido[4,3-d]pyrimidine 250 mL flask was charged with 6-benzyl-4-methoxy-5,6,7,8-tetrahydropyrido[4,3-d]pyrimidine (4.08 g, 16.0 mmol), 10% palladium on charcoal (400 mg) and methanol (100 mL). The reaction was evacuated and purged with hydrogen three times, and hydrogenated (1 atm) overnight. The mixture was filtered through a "Dry disk" membrane filter, and concentrated in vacuo to yield an orange oil (2.56 g).
¹H NMR (400 MHz, CDCl₃): δ 8.57 (s, 1H), 3.99 (s, 3H), 3.87 (s, 2H), 3.18 (t, 2H, J=6.9 Hz), 2.82 (t, 2H, J=6.9 Hz).

Intermediate 4

2-(4-Bromo-7,8-dihydropyrido[4,3-d]pyrimidin-6(5H)-yl)-5-chlorobenzonitrile

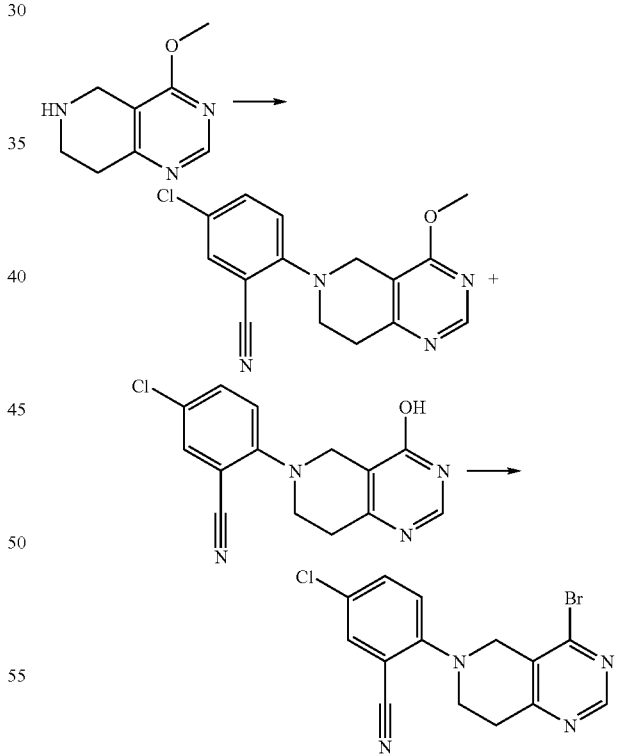

A) 5-Chloro-2-(4-methoxy-7,8-dihydropyrido[4,3-d]pyrimidin-6(5H)-yl)benzonitrile and 5-chloro-2-(4-hydroxy-7,8-dihydropyrido[4,3-d]pyrimidin-6(5H)-yl)benzonitrile A 20 mL microwave vial was charged with 4-methoxy-5,6,7,8-tetrahydropyrido[4,3-d]pyrimidine (1.88 g, 11.4 mmol), 5-chloro-2-fluorobenzonitrile (2.8 g, 18 mmol), N,N-diisopropylethylamine (3.01 mL), and acetonitrile (5 mL). The mixture was subjected to microwave irradiation at 200° C. for 3.5 h. The mixture was diluted with chloroform (50 mL), washed with 0.3 M aqueous NaH₂PO₄ (75 mL), then extracted with 2M KOH (20 mL×2). The organic layer containing the methoxy-pyrimidine was dried (Na₂SO₄), filtered and concentrated to a brown-red solid, which was purified by silica gel column (0-4% MeOH/CH₂Cl₂) to yield a brown oil (0.43 g). The combined aqueous KOH extracts were acidified with 1M aqueous H₂SO₄, and extracted with chloroform (30 μL×2), dried (Na₂SO₄), filtered and concentrated to afford the crude hydroxy-pyrimidine as a brown solid (0.84 g).

LC-MS: 287.3 [M+H]$^+$

B) 2-(4-Bromo-7,8-dihydropyrido[4,3-d]pyrimidin-6 (5H)-yl)-5-chlorobenzonitrile

POBr₃ (1.61 g, 5.6 mmol) was added portionwise over 2 min to a mixture of 5-chloro-2-(4-hydroxy-7,8-dihydropyrido[4,3-d]pyrimidin-6(5H)-yl)benzonitrile (0.82 g, 2.8 mmol), N,N-dimethylaniline (0.7 mL), and N,N-dimethylformamide (0.02 mL) in acetonitrile (10 mL) and anisole (10 mL). The mixture was heated under reflux for 2.5 h and LC-MS showed reaction was complete. After cooling the mixture was diluted with chloroform (20 mL) and poured into a stirred mixture of ice (50 g), 50% KOH (8 mL) and chloroform (100 mL). The organic layer was separated and the aqueous layer was extracted with chloroform (25 mL×2). The combined organic layers were washed with brine (100 mL), dred (Na₂SO₄), filtered and concentrated. The residue was purified by silica gel column to yield a brown solid (0.35 g).

$^1$H NMR (400 MHz, CDCl₃): δ 8.85 (s, 1H), 7.61 (d, 1H, J=2.4 Hz), 7.52 (dd, 1H, J=8.8, 2.4 Hz), 7.11 (d, 1H, J=8.8 Hz), 4.34 (s, 2H), 3.68 (t, 2H, J=5.6 Hz), 3.27 (t, 2H, J=5.6 Hz).

Intermediate 5

2-(4-Chloro-7,8-dihydropyrido[4,3-d]pyrimidin-6 (5H)-yl)-5-methylbenzonitrile

A) 2-(4-Methoxy-7,8-dihydropyrido[4,3-d]pyrimidin-6(5H)-yl)-5-methylbenzonitrile A 100 mL flask was charged with 4-methoxy-5,6,7,8-tetrahydropyrido[4,3-d]pyrimidine (2.78 g, 16 mmol), 2-bromo-5-methylbenzonitrile (4.18 g, 19.2 mmol), bis(dibenzylideneacetone)palladium(0) (372 mg, 0.64 mmol), xantphos (529 mg, 0.896 mmol), and sodium tert-butoxide (2.33 g, 24 mmol), capped with a septum and purged with nitrogen. Dry argon-sparged toluene (50 mL) was added. The heterogeneous mixture was placed in an oil bath at 100° C., and heated under argon overnight. After 14 hours, TLC showed the reaction was complete. The mixture was removed from the heat, diluted with ethyl acetate (50 mL), filtered and concentrated in vacuo. The residue was purified by silica gel column (0-100% EtOAc/hexane) to afford a light orange solid.

B) 2-(4-Chloro-7,8-dihydropyrido[4,3-d]pyrimidin-6 (5H)-yl)-5-methylbenzonitrile A mixture of 2-(4-methoxy-7,8-dihydropyrido[4,3-d]pyrimidin-6(5H)-yl)-5-methylbenzonitrile (4.15 g, 14.1 mmol), N,N-dimethylaniline (0.181 mL, 1.4 mmol), N,N-dimethylformamide (0.21 mL, 2.7 mmol) and acetonitrile (35 mL) was heated to dissolve at 105° C. Phosphoryl chloride (5.3 mL, 56 mmol) was added dropwise over 3 mins, and the reaction was heated to reflux at 110° C. After 40 mins, additional phosphoryl chloride (5.3 mL, 0.056 mol) was added dropwise over 3 mins. After another 20 hours, $^1$H NMR showed that the reaction was ca 70% complete and the reaction mixture was allowed to cool and poured over ice (200 g) and 45% aq. NaOH (75 mL) was added. The mixture was extracted with CH₂Cl₂ (3×200 mL). The combined organic layers were dried over sodium sulfate and concentrated. The residue was purified by silica gel column (0-100% EtOAc/hexane) to yield a brown oil which became a solid in the freezer.

LC-MS: 285.5 [M+H]$^+$ $^1$H NMR (300 MHz, CDCl₃): δ 8.81 (s, 1H), 7.42 (d, 1H, J=2.1 Hz), 7.34 (dd, 1H, J=8.4, 2.1 Hz), 7.04 (d, 1H, J=8.4 Hz), 4.29 (s, 2H), 3.60 (t, 2H, J=5.7 Hz), 3.23 (t, 2H, J=5.7 Hz), 2.32 (s, 3H).

Intermediate 6

5-Chloro-2-(4-chloro-7,8-dihydropyrido[4,3-d]pyrimidin-6(5H)-yl)benzonitrile

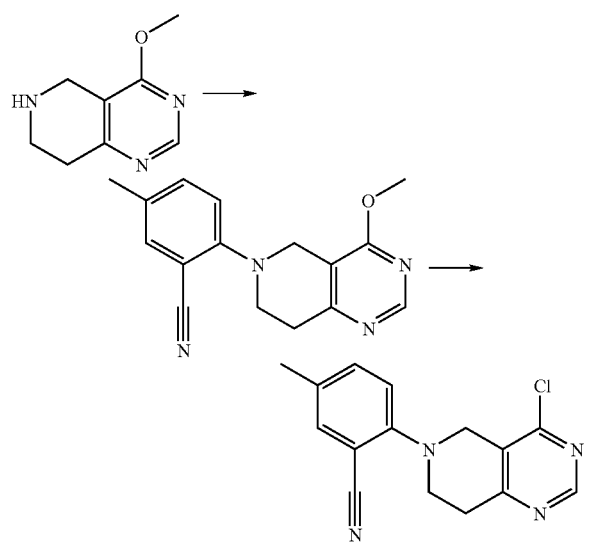

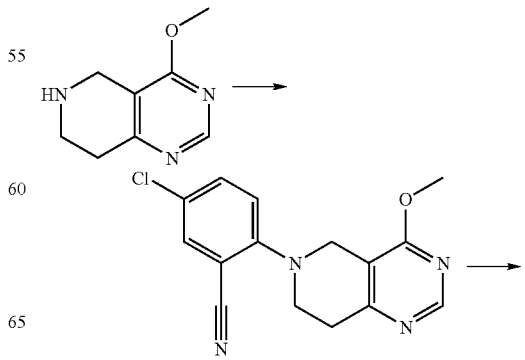

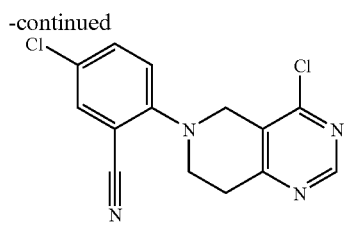

A) 5-Chloro-2-(4-methoxy-7,8-dihydropyrido[4,3-d]pyrimidin-6(5H)-yl)benzonitrile A mixture of 4-methoxy-5,6,7,8-tetrahydropyrido[4,3-d]pyrimidine (12.88 g, 0.078 mol), 5-chloro-2-fluorobenzonitrile (40 g, 0.2 mol), and 1,8-diazabicyclo[5.4.0]undec-7-ene (60 mL, 0.4 mol) was heated at 80° C. for 3 hours. After cooling the mixture was diluted with CH₂Cl₂ (300 mL), washed with water, dried, and concentrated to afford a brown solid which was purified by silica gel chromatography (0-50% EtOAc/hexane) to afford a solid (19.33 g, 78.3%).

B) 5-Chloro-2-(4-chloro-7,8-dihydropyrido[4,3-d]pyrimidin-6(5H)-yl)benzonitrile A mixture of 5-chloro-2-(4-methoxy-7,8-dihydropyrido[4,3-d]pyrimidin-6(5H)-yl)benzonitrile (4.15 g, 13.1 mmol), N,N-dimethylaniline (0.18 mL, 1.4 mmol), N,N-dimethylformamide (0.21 mL, 2.7 mmol) and acetonitrile (35 mL) was heated to dissolve at 105° C. Phosphoryl chloride (5.3 mL, 56 mmol) was added dropwise over 3 mins and the mixture was heated to reflux at 110° C. After another 20 hours refluxing, the reaction mixture was allowed to cool and poured over ice (200 g), and then 45% NaOH (75 mL) was added. The mixture was extracted with CH₂Cl₂ (3×200 mL). The combined organic layers were dried over sodium sulfate, and concentrated. The residue was purified by silica gel chromatography (0-100% EtOAc/hexane) to afford a yellow oil which became a solid in the freezer.

$^1$H NMR (300 MHz, CDCl₃): δ 8.83 (s, 1H), 7.59 (d, 1H, J=2.4 Hz), 7.50 (dd, 1H, J=8.7, 2.4 Hz), 7.09 (d, 1H, J=8.7 Hz), 4.32 (s, 2H), 3.66 (t, 2H, J=5.7 Hz), 3.25 (t, 2H, J=5.7 Hz).

Intermediates 7 and 8

(R)-1-(6-(Trifluoromethyl)pyridin-3-yl)ethanamine and (S)-1-(6-(trifluoromethyl)pyridin-3-yl)ethanamine

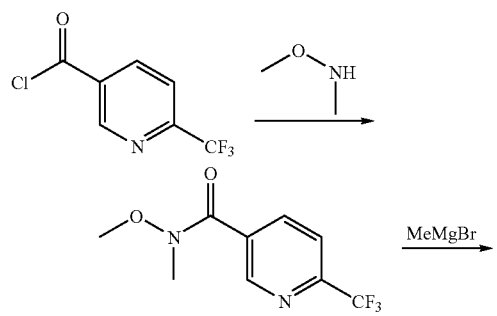

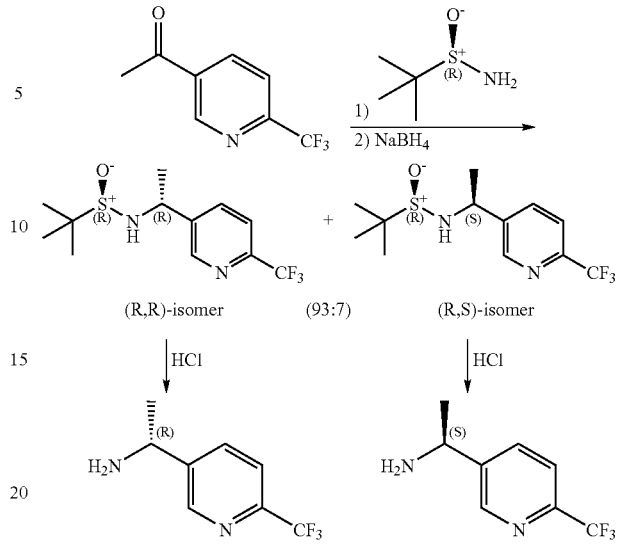

A) N-methoxy-N-methyl-6-(trifluoromethyl)nicotinamide

To a stirred mixture of N,O-dimethylhydroxylamine hydrochloride (9.47 g, 97.1 mmol) and pyridine (18.6 mL, 230 mmol) in CH₂Cl₂ (100 mL) was added a solution of 6-(trifluoromethyl)nicotinoyl chloride (18.50 g, 88.28 mmol) in CH₂Cl₂ (250 mL) over 3-5 min. The reaction mixture was stirred at rt overnight, and then carefully quenched with 150 mL of saturated aq. NaHCO₃ solution and stirred for about 1 hr. The mixture was diluted with CH₂Cl₂ (50 mL) and the organic phase was separated and washed with aq. NaHCO₃ solution (100 mL) and brine (50 mL), dried (Na₂SO₄), filtered, and evaporated. The residue was redissolved in toluene (about 50 mL) and evaporated again to azeotrope the pyridine off. This was repeated with toluene (about 50 mL). The product was isolated as a colorless oil (with a small amount of crystalline material) (19.1 g, 92%).

LC-MS: 235.4 [M+1]⁺;

$^1$H NMR (400 MHz, CDCl₃): δ 9.05 (d, 1H, J=1.6 Hz), 8.22 (dd, 1H, J=8.0, 1.6 Hz), 7.76 (d, 1H, J=8.0 Hz), 3.57 (s, 3H), 3.42 (s, 3H).

B) 1-(6-(trifluoromethyl)pyridin-3-yl)ethanone

N-Methoxy-N-methyl-6-(trifluoromethyl)nicotinamide (19.1 g, 81.6 mmol) was dissolved in tetrahydrofuran (410 mL). The system was purged with N₂ and then cooled to 0° C. 1.4 M of methylmagnesium bromide in toluene/THF (75:25) (87.4 mL, 122.4 mmol) was added dropwise using an additional funnel. At the end of the addition the mixture was cloudy off-white. The mixture was stirred at 0° C. for 1 hour and carefully quenched by dropwise addition of 1 M aq. HCl (150 mL) and diluted with ethyl ether (300 mL) and EtOAc (100 mL). The organic layer was separated and washed with 0.1 M aq. NaOH (200 mL) and brine (2×50 mL), dried (Na₂SO₄), and concentrated to yield a light yellow solid (15.04 g, 98%).

LC-MS: 190.2 [M+1]⁺; $^1$H NMR (400 MHz, CDCl₃): δ 9.25 (d, 1H, J=1.6 Hz), 8.42 (dd, 1H, J=8.0, 1.6 Hz), 7.82 (d, 1H, J=8.0 Hz), 2.70 (s, 3H).

C) (R)-2-methyl-N—((R)-1-(6-(trifluoromethyl)pyridin-3-yl)ethyl)propane-2-sulfinamide and (R)-2-methyl-N—((S)-1-(6-(trifluoromethyl)pyridin-3-yl)ethyl)propane-2-sulfinamide To a solution of 1-(6-(trifluoromethyl)pyridin-3-yl)ethanone (15.0 g, 79.3 mmol) in tetrahydrofuran (450 mL) under $N_2$ was added tetraethoxytitanium (28.8 mL, 132 mmol). Solid (R)-(+x)-2-methylpropane-2-sulfinamide (8.01 g, 66.1 mmol) was then added and the reaction was heated under reflux overnight. The resulting imine solution was cooled to −45 to −50° C. and cannulated into flask containing sodium tetrahydroborate (12.5 g, 330 mmol) and tetrahydrofuran (100 mL) that was cooled to −45 to −50° C. The resulting cloudy orange solution was stirred at −40° C. for 4 h and then slowly warmed to rt and stirred at rt for 2 days. After cooling to 0° C., the reaction mixture was carefully quenched by dropwise addition of MeOH (100 mL) followed by dropwise addition of water (40 mL). The mixture was stirred for about 20 minutes, and then rotovapped to dryness. EtOAc (500 mL) was added and the mixture was stirred for about 1 hr, and then brine (50 mL) was added portionwise. The mixture was filtered through Celite and the filter cake was washed with EtOAc (3×100 mL). The filtrate was washed with saturated aq. $NaHCO_3$, water, and brine, dried ($Na_2SO_4$), concentrated to yield a light yellow waxy solid (22.40 g, 96%). $^1$H NMR of the crude product indicates about 93:7 ratio of two diastereomers. The product was recrystallized from EtOAc (150 mL) and washed with cold EtOAc (3×20 mL) to yield a white crystalline solid (12.22 g, 52.5%) as the (R,R)-isomer. The mother liquor was concentrated and purified by silica gel column chromatography to yield additional (R,R)-isomer (5 g, 21%) and the (R,S)-isomer (1.1 g) which was recrystallized from methylcyclohexane to yield an off white solid. $^1$H NMR ($CDCl_3$ and DMSO-d6) of each recrystallized fraction (R, R and R, S) indicated less than 1% of the other isomer and good purities in all cases.

(R,R)-isomer: LC-MS: 295.4 [M+1]$^+$;
$^1$H NMR (400 MHz, $CDCl_3$): δ 8.73 (d, 1H, J=1.6 Hz), 7.90 (dd, 1H, J=8.0, 2.4 Hz), 7.69 (d, 1H, J=8.0 Hz), 4.68 (m, 1H), 3.53 (d, 1H, J=3.6 Hz), 1.59 (d, 3H, J=6.8 Hz), 1.25 (s, 9H). $^1$H NMR (d6-DMSO): 8.80 (d, 1H, J=1.6 Hz), 8.11 (dd, 1H, J=8.0, 2.0 Hz), 7.90 (d, 1H, J=8.0 Hz), 5.94 (d, 1H, J=7.6 Hz), 4.57 (p, 1H, J=7.2 Hz), 1.46 (d, 3H, J=7.2 Hz), 1.13 (s, 9H).

(R,S)-isomer: $^1$H NMR (400 MHz, $CDCl_3$): 8.73 (d, 1H, J=1.6 Hz), 7.84 (dd, 1H, J=8.0, 1.6 Hz), 7.67 (d, 1H, J=8.0 Hz), 4.72 (m, 1H), 3.42 (d, 1H, J=2.4 Hz), 1.60 (d, 3H, J=6.8 Hz), 1.23 (s, 9H).
$^1$H NMR (d6-DMSO): 8.77 (d, 1H, J=1.6 Hz), 8.06 (dd, 1H, J=8.0, 2.0 Hz), 7.90 (d, 1H, J=8.0 Hz), 5.67 (d, 1H, J=6.0 Hz), 4.62 (p, 1H, J=6.4 Hz), 1.52 (d, 3H, J=6.8 Hz), 1.12 (s, 9H).

D) (R)-1-(6-(trifluoromethyl)pyridin-3-yl)ethanamine (R)-2-Methyl-N—((R)-1-(6-(trifluoromethyl)pyridin-3-yl)ethyl)propane-2-sulfinamide (12.75 g, 43.32 mmol) was added to a 200 mL flask followed by addition of 1,4-dioxane (58 mL). 6.0 M of aqueous HCl (28.9 mL) was added and the reaction was stirred at rt for 1.5 hrs to ensure all of the sulfinyl chloride was destroyed. The solvent was evaporated and the residue was treated with $CH_2Cl_2$ (200 mL) and 1 M aq. NaOH (200 mL). The organic layer was separated and the aqueous layer was extracted with $CH_2Cl_2$ (2×50 mL). The organic layers were combined and dried with $Na_2SO_4$, and concentrated to obtain a clear colorless liquid (8.30 g). Chiral HPLC analysis (ChiralPac AD-H column 250×4.6 mm, hexane/$^i$PrOH/$Et_2$NH: 95/5/0.05): 97.8% R-isomer (10.69 min), 0.63% S-isomer (9.63 min).
LC-MS: 191.2 [M+1]$^+$;
$^1$H NMR (400 MHz, $CDCl_3$): δ 8.72 (d, 1H, J=1.6 Hz), 7.92 (dd, 1H, J=8.0, 2.0 Hz), 7.66 (d, 1H, J=8.0 Hz), 4.30 (q, 1H, J=6.8 Hz), 1.62 (s, 2H), 1.43 (d, 3H, J=6.8 Hz).

E) (S)-1-(6-(trifluoromethyl)pyridin-3-yl)ethanamine

To (R)-2-Methyl-N—((S)-1-(6-(trifluoromethyl)pyridin-3-yl)ethyl)propane-2-sulfinamide (355 mg, 1.21 mmol) in a 20 mL scintillation vial was added 1,4-dioxane (1.6 mL) and 6.0 M of aq. HCl (0.80 mL). The reaction was stirred at rt for about 2 hours and then the dioxane was evaporated. Water (3 mL) was added and 1 M aq. NaOH was added until pH>12 was attained. The basic aqueous was extracted with $CH_2Cl_2$ (5 mL×2). The combined organic layers were dried with $Na_2SO_4$, filtered and evaporated to obtain a clear light yellow liquid (123 mg, 54%). Chiral HPLC analysis (ChiralPac AD-H column 250×4.6 mm, hexane/$^i$PrOH/$Et_2$NH: 95/5/0.05): 97% S-isomer (9.61 min), no significant evidence of R-isomer at 10.7 min.
LC-MS: 191.2 [M+1]$^+$;
$^1$H NMR (400 MHz, $CDCl_3$): δ 8.72 (d, 1H, J=1.6 Hz), 7.92 (dd, 1H, J=8.0, 2.0 Hz), 7.66 (d, 1H, J=8.0 Hz), 4.30 (q, 1H, J=6.8 Hz), 1.55 (s, 2H), 1.43 (d, 3H, J=6.8 Hz).

Intermediate 9

(5-Cyclopropylpyridin-2-yl)methanamine

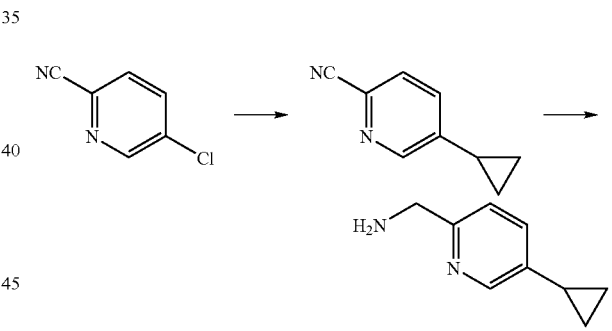

A) 2-Cyano-5-cyclopropylpyridine

To a mixture of 5-chloro-2-cyanopyridine (1.25 g, 9.02 mmol), cyclopropylboronic acid (1.00 g, 11.7 mmol), potassium phosphate (6.70 g, 31.6 mmol), tricyclohexylphosphine (380 mg, 1.4 mmol), toluene (200 mL), and water (2 mL) under argon was added palladium acetate (150 mg, 0.68 mmol). The mixture was heated at 100° C. overnight and then cooled to rt. The mixture was filtered through Celite and the filter cake was washed with EtOAc. The filtrate was washed with water, dried ($Na_2SO_4$), and concentrated. The residue was purified by silica gel column (EtOAc/hexane: 0-50%) to yield a light yellow oil which becomes solid while standing at room temperature.
LC-MS: 145.3[M+H]$^+$
$^1$H NMR (400 MHz, $CDCl_3$): δ 8.49 (d, 1H, J=2.4 Hz), 7.57 (d, 1H, J=8.0 Hz), 7.37 (dd, 1H, J=8.0, 2.4 Hz), 1.97 (m, 1H), 1.18 (m, 2H), 0.83 (m, 2H).

B) (5-Cyclopropylpyridin-2-yl)methanamine

To a solution of 2-cyano-5-cyclopropylpyridine (210 mg, 1.4 mmol) in 20 mL of 7.0 M ammonia in MeOH was added a small spoon of Raney Ni slurry. The mixture was hydrogenated at 50 psi overnight. The catalyst was filtered off and the filtrate was concentrated to yield a dark oil which was used for the next step reaction without further purification.
LC-MS: 149.2 [M+H]$^+$

Intermediate 10

(S)-2-Amino-2-(6-methoxypyridin-3-yl)ethanol

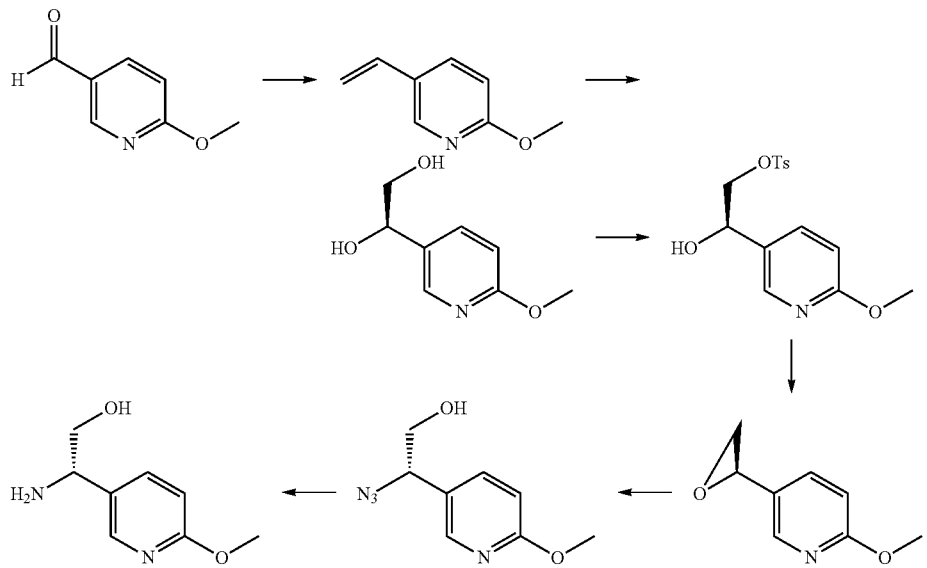

A) 2-Methoxy-5-vinylpyridine

A suspension of triphenylmethylphosphonium bromide (31.2 g, 0.0875 mol) in THF (150 mL) at −78° C. under an atmosphere of nitrogen was added 2.5 M n-BuLi (38.0 mL, 0.0948 mol) in hexane during a period of 30 min. The reaction was warmed to room temperature to yield a deep red ylide solution. To the ylide solution, cooled in ice, was introduced 6-methoxynicotinaldehyde (10.0 g, 0.0729 mol) in THF (30 mL). The reaction was allowed to reach room temperature and stirred at room temperature for 3 h. Then the result suspension was heated to 60° C. over 30 minutes and heated at 60° C. for 1 hour. After cooling, the reaction was diluted with water (500 mL). The product was extracted into ethyl ether, washed with brine, dried (MgSO$_4$), and concentrated. The residue was purified by silica gel column (0-40% EtOAc/hexane) to yield a light yellow oil. LC-MS: 136.0 [M+1]$^+$;
$^1$H NMR (400 MHz, CDCl$_3$): δ 8.12 (d, 1H, J=2.4 Hz), 7.70 (dd, 1H, J=8.4, 2.4 Hz), 6.72 (d, 1H, J=8.4 Hz), 6.65 (dd, 1H, J=17.6, 11.2 Hz), 5.64 (d, 1H, J=17.6 Hz), 5.22 (d, 1H, J=11.2 Hz), 3.94 (s, 3H).

B) (R)-1-(6-Methoxypyridin-3-yl)ethane-1,2-diol

A 500 mL flask was charged with tert-butyl alcohol (130 mL), water (130 mL), and AD-mix-β (36.5 g). Stirring at rt produced two clear phases; the lower aqueous phase appears bright yellow. The mixture was cooled to 0° C. whereupon some of the dissolved salts precipitated. 2-Methoxy-5-vinylpyridine (3.5 g, 26 mmol) was added at once, and the heterogeneous slurry was stirred vigorously at 0° C. for 6 h. LC-MS indicated completion of the reaction. While the mixture was stirred at 0° C., solid sodium sulfite (39 g) was added and the mixture was allowed to warm to rt and stirred for 1 h. EtOAc (250 mL) was added to the reaction mixture, and after separation of the layers, the aqueous phase was further extracted with EtOAc (3×100 mL). The combined organic layers were dried over anhydrous MgSO$_4$ and concentrated in vacuo. The residue was purified by silica gel column (0-100% EtOAc/hexane) to yield the diol as a white solid (2.76 g, 63%). LC-MS: 170.2 [M+1]$^+$.

C) (R)-2-Hydroxy-2-(6-methoxypyridin-3-yl)ethyl 4-methylbenzenesulfonate

To a stirred solution of (R)-1-(6-methoxypyridin-3-yl)ethane-1,2-diol (2.7 g, 0.016 mol) and pyridine (10 mL) in CH$_2$Cl$_2$ (100 mL) at 0° C. was added p-toluenesulfonyl chloride (3.6 g, 0.019 mol) in small portions. The mixture was slowly warmed to rt and stirred for 24 h, and then diluted with CH$_2$Cl$_2$ (100 mL). The organic phase was washed with aq. NaHCO$_3$, brine, dried (Na$_2$SO$_4$), and concentrated to yield a solid (6.0 g). LC-MS: 324.0 [M+H]$^+$.

D) (R)-2-Methoxy-5-(oxiran-2-yl)pyridine

To a stirred solution of (R)-2-hydroxy-2-(6-methoxypyridin-3-yl)ethyl 4-methylbenzenesulfonate in MeOH (150 mL) at 0° C. was added potassium carbonate (4.4 g, 0.032 mol) and the mixture was stirred at rt overnight. The mixture was filtered through Celite and the filter cake was washed with MeOH. The filtrate was concentrated and the residue was treated with EtOAc (150 mL) and aq. Na$_2$CO$_3$. The organic layer was separated and washed with brine, dried (Na$_2$SO$_4$), and concentrated. The residue was purified by silica gel column to yield the desired expoxide as a colorless oil (1.02 g, 42%).
$^1$H NMR (400 MHz, CDCl$_3$): δ 8.14 (d, 1H, J=2.4 Hz), 7.40 (dd, 1H, J=8.8, 2.4 Hz), 6.73 (d, 1H, J=8.4 Hz), 3.93 (s, 3H), 3.84 (m, 1H), 3.16 (m, 1H), 2.83 (m, 1H).

E) (S)-2-Azido-2-(6-methoxypyridin-3-yl)ethanol

To a stirred solution of (R)-2-methoxy-5-(oxiran-2-yl)pyridine (1.02 g, 6.75 mmol) in acetonitrile (100 mL) were added sodium azide (1.8 g, 27 mmol) and lithium perchlorate (11 g, 0.10 mol) and the mixture was stirred at 60° C. for 4 h. TLC indicated completion of the reaction. After cooling, the mixture was filtered through Celite and the filtrate was concentrated. The residue was treated with water and extracted with EtOAc (3×50 mL). The combined organic layers were washed with aq. NaHCO₃ and brine, dried (Na₂SO₄), and concentrated. The residue was purified by silica gel column (0-50% EtOAc/hexane) to yield a light yellow oil (0.9 g, 69%).

LC-MS: 195.2 [M+H]$^+$;

$^1$H NMR (400 MHz, CDCl$_3$): δ 8.14 (d, 1H, J=2.4 Hz), 7.58 (dd, 1H, J=8.4, 2.4 Hz), 6.79 (d, 1H, J=8.4 Hz), 4.64 (t, 1H, J=6.4 Hz), 3.95 (s, 3H), 3.75 (d, 2H, J=6.4 Hz), 1.90 (bs, 1H).

F) (S)-2-Amino-2-(6-methoxypyridin-3-yl)ethanol

A mixture of (S)-2-azido-2-(6-methoxypyridin-3-yl)ethanol (0.90 g, 4.6 mmol), EtOAc (50 mL), and 10% Pd—C (100 mg) was stirred under H$_2$ (1 atm) for 1 h. The catalyst was filtered off and the filtrate was concentrated in vacuo to yield a thick oil (0.78 g, 100%).

LC-MS: 169.2 [M+1]$^+$;

$^1$H NMR (400 MHz, d6-DMSO): 8.08 (d, 1H, J=2.4 Hz), 7.68 (dd, 1H, J=8.4, 2.4 Hz), 6.75 (d, 1H, J=8.4 Hz), 4.78 (t, 1H, J=5.6 Hz), 3.85-3.80 (m, 4H), 3.38 (m, 1H), 3.31 (m, 1H), 1.83 (bs, 2H).

Intermediates 11 and 12

(R)-3-Amino-3-(6-(trifluoromethyl)pyridin-3-yl)propan-1-ol and (S)-3-amino-3-(6-(trifluoromethyl)pyridin-3-yl)propan-1-ol

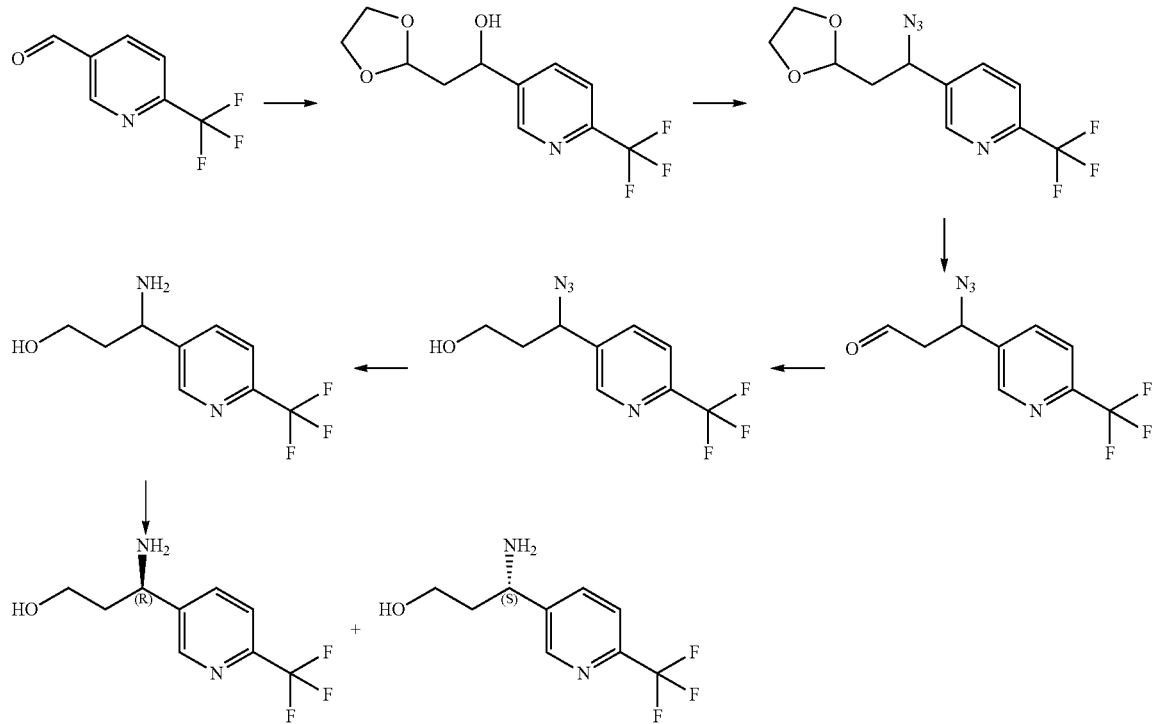

A) 2-(1,3-dioxolan-2-yl)-1-(6-(trifluoromethyl)pyridin-3-yl)ethanol

A suspension of 6-(trifluoromethyl)nicotinaldehyde (23.5 g, 0.134 mol) in tetrahydrofuran (500 mL) at 0° C. under an atmosphere of nitrogen was added 0.5 M of (1,3-dioxxlan-2-ylmethyl)-magnesium bromide solution in tetrahydrofuran (400 mL, 0.20 mol), and the reaction was warmed to room temperature and then refluxed overnight. The reaction mixture was cooled to room temperature and quenched with water. The aqueous layer was extracted with EtOAc and the organic layers were combined, dried over MgSO$_4$, filtered, and concentrated. The residue was purified by silica gel column (0-50% EtOAc/hexane) to yield a yellow oil.

B) 5-(1-azido-2-(1,3-dioxolan-2-yl)ethyl)-2-(trifluoromethyl)pyridine

A mixture of 2-(1,3-dioxolan-2-yl)-1-(6-(trifluoromethyl)pyridin-3-yl)ethanol (18.54 g, 0.070 mol) and diphenylphosphonic azide (36 mL, 0.17 mol) in toluene (40 mL) was cooled to 0° C. and neat 1,8-diazabicyclo[5.4.0]undec-7-ene (25 mL, 0.17 mol) was added. The reaction mixture was stirred at 0° C. for 2 hr and then at 20° C. overnight. The mixture was washed with water and 5% HCl. The aqueous phase was extracted with CH$_2$Cl$_2$. The combined orangic layers were concentrated in vacuo and the residue was purified by silica gel column (0-100% EtOAc/hexane) to afford a colorless oil.

C) 3-azido-3-(6-(trifluoromethyl)pyridin-3-yl)propanal

A solution of 5-(1-azido-2-(1,3-dioxolan-2-yl)ethyl)-2-(trifluoromethyl)pyridine (7.44 g, 25.8 mmol) in tetrahydrofuran (60 mL) was treated with 20% aq. HCl (60 mL) at 0° C. The mixture was stirred at room temperature for 1.5 hours. After completion of the reaction, ethyl ether was added and the organic layer was separated, dried over MgSO$_4$, and concentrated to yield a crude oil without further purification.

D) 3-azido-3-(6-(trifluoromethyl)pyridin-3-yl)propan-1-ol

To a stirred solution of the crude 3-azido-3-(6-(trifluoromethyl)pyridin-3-yl)propanal (5.0 g, 20.5 mmol) in tetrahydrofuran (100 mL) at 0° C. was added sodium tetrahydroborate (1.52 g, 40.1 mmol). The mixture was stirred at room temperature for 10 minutes. After completion of the reaction, brine was added and the mixture was extracted with ether. The organic layer was dried and concentrated to afford a crude oil which was purified by silica gel chromatography to afford a light yellow oil.

E) 3-amino-3-(6-(trifluoromethyl)pyridin-3-yl)propan-1-ol

A mixture of 3-azido-3-(6-(trifluoromethyl)pyridin-3-yl)propan-1-ol (7.29 g, 29.6 mmol), ethyl acetate (320 mL), and 10% Pd—C (3.2 g) was stirred under H$_2$ (1 atm) overnight. The catalyst was filtered off and the filtrate was concentrated in vacuo to yield the title product.

F) (S)-3-amino-3-(6-(trifluoromethyl)pyridin-3-yl)propan-1-ol and (R)-3-amino-3-(6-(trifluoromethyl)pyridin-3-yl)propan-1-ol Racemic 3-amino-3-(6-(trifluoromethyl)pyridin-3-yl)propan-1-ol (1.10 g, 5.00 mmol) was resolved by chiral HPLC (conditions: CHIRALPAK AD-H column, 20×250 mm, hexane/EtOH [88:12] at 20 mL/min, UV at 230 nm) to yield (S)-3-amino-3-(6-(trifluoromethyl)pyridin-3-yl)propan-1-ol and (R)-3-amino-3-(6-(trifluoromethyl)pyridin-3-yl)propan-1-ol. Analytical chiral HPLC: CHIRALPAK AD-H column, 250×4.6 mm, hexane/EtOH [90:10] at 1.0 mL/min, UV at 230 nm); retention time for (S)-isomer: 18.68 min (>99% ee); retention time for (R)-isomer: 23.56 min (>99% ee).

Intermediate 13

(2-Methylpyrimidin-5-yl)methanamine

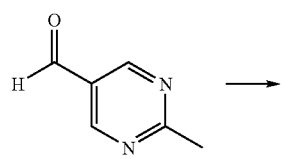

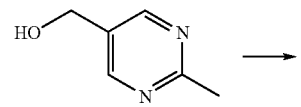

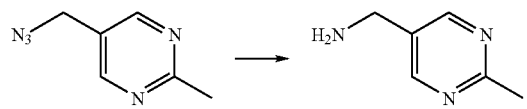

A) 2-Methylpyrimidine-5-carbaldehyde

To a stirred slurry of acetamidine hydrochloride (19.4 g, 0.20 mol) and vinamidinium salt (48.91 g, 0.183 mol) in acetonitrile (240 mL) was added a solution of 40% wt. NaOH in water (27.4 g, 0.274 mol) over a 30 minutes period. After the addition was complete, the resulting reaction mixture was stirred at room temperature overnight. The mixture was concentrated in vacuo and diluted with water (250 mL) and extracted with EtOAc (3×250 mL). The combined organic layers were dried over sodium sulfate and concentrated in vacuo. The residue was purified by silica gel chromatography (0-100% EtOAc/hexanes) to afford a white solid.

B) (2-Methylpyrimidin-5-yl)methanol

A solution of 2-methylpyrimidine-5-carbaldehyde (6.48 g, 53.1 mmol) in methanol (320 mL) was cooled to 0° C. and treated with sodium tetrahydroborate (2.9 g, 77 mmol). After 30 min, the reaction was treated with H$_2$O (50 mL) and extracted with EtOAc (250 mL×15). The organic layers were combined and dried over MgSO$_4$ and concentrated to yield a white solid.

C) 5-(Azidomethyl)-2-methylpyrimidine

A solution of (2-methylpyrimidin-5-yl)methanol (0.82 g, 6.6 mmol) in toluene (30 mL) and methylene chloride (40 mL) at 0° C. was treated with diphenylphosphonic azide (2.8 mL, 13 mmol) followed by 1,8-diazabicyclo[5.4.0]undec-7-ene (2.0 mL, 13 mmol) and stirred at 0° C. for 2 h. After being further stirred at rt for 16 h, the reaction mixture was diluted with water (50 mL) and methylene chloride (50 mL). The organic layer was separated and washed with brine, dried (Mg$_2$SO$_4$), filtered, and concentration. The residue was purified by silica gel column to yield a colorless oil.

D) (2-Methylpyrimidin-5-yl)methanamine

A mixture of 5-(azidomethyl)-2-methylpyrimidine (2.0, 13.4 mmol) in ethyl acetate (100 mL), and 10% Pd—C (4.0 g) was stirred under H$_2$ (1 atm) for 1.5 hr. The catalyst was filtered off and filtrate was concentrated in vacuo to afford a white solid.

$^1$H NMR (300 MHz, CD$_3$OD): δ 8.67 (s, 2H), 3.81 (s, 2H), 2.66 (s, 3H).

Intermediate 14

(S)-2-(tert-Butyldimethylsilyloxy)-1-(2-methoxypyrimidin-5-yl)ethanamine

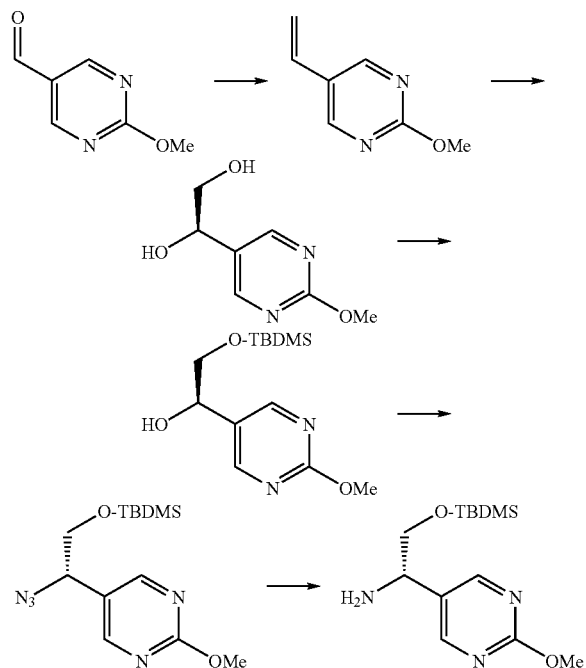

A) 2-Methoxypyrimidine-5-carbaldehyde

To a stirred slurry of O-methylisourea hemisulfate (1.08 g, 4.13 mmol), vinamidinium salt (3.00 g, 8.26 mmol), 1-methylethyl acetate (16.0 mL, 137 mmol) was added a solution of potassium bicarbonate (1.17 g, 11.6 mmol) in water (5.0 mL) over a 10 minutes period. After completion of the addition the resulting reaction mixture was stirred at room temperature for 40 hours. The mixture was diluted with water (20 mL) and extracted with EtOAc (2×25 mL). The combined organic layers were dried over sodium sulfate and concentrated to yield a white solid.

$^1$H NMR (300 MHz, CDCl$_3$) δ: 4.11 (s, 3H), 8.97 (s, 2H), 10.00 (s, 1H).

B) 2-Methoxy-5-vinylpyrimidine

A suspension of methyltriphenylphosphonium bromide (24.8 g, 69.4 mmol) in THF (150 mL) at −78° C. under an atmosphere of nitrogen was added 2.5 M of n-butyllithium in hexane (28 mL, 70 mmol) during a period of 12 mins. The reaction was warmed to room temperature to yield a deep red ylide solution. To the ylide solution, cooled in ice, was introduced 2-methoxypyrimidine-5-carbaldehyde (8 g, 65.6 mmol) in THF (50 mL). The reaction was allowed to reach room temperature and stirred for 3 hours. The result suspension was heated to 60° C. over 30 minutes and then heated at 60° C. for 1 hour. After cooling, the reaction mixture was diluted with water (400 mL) and extracted with EtOAc (2×150 mL). The combined organic layers were washed with brine, dried (MgSO$_4$), and concentrated. The residue was purified by silica gel chromatography (EtOAc/hexane 0-30%) to yield title compound.

C) (R)-1-(2-Methoxypyrimidin-5-yl)ethane-1,2-diol

A 100 mL flask was charged with tert-butyl alcohol (39 mL), water (39 mL), and AD-mix-β (11.0 g). Stirring at room temperature produced two clear phases; the lower aqueous phase appears bright yellow. The mixture was cooled to 0° C. whereupon some of the dissolved salts precipitated. 2-Methoxy-5-vinylpyrimidine (1.07 g, 7.86 mmol) was added at once, and the heterogeneous slurry was stirred vigorously at −20° C. for overnight. TLC indicated completion of the reaction. While the mixture was stirred at 0° C., solid sodium sulfite (12 g, 94 mmol) was added and the mixture was allowed to warm to rt and stirred for 1 hour. EtOAc (100 mL) was added to the reaction mixture, and after separation of the layers, the aqueous phase was further extracted with EtOAc (2×100 mL). The combined organic layers were dried over anhydrous MgSO$_4$ and concentrated in vacuo. The residue was purified by silica gel column (EtOAc/hexane: 50-100%) to yield the diol as a white solid.

D) (R)-2-(tert-Butyldimethylsilyloxy)-1-(2-methoxypyrimidin-5-yl)ethanol

A mixture of (R)-1-(2-methoxypyrimidin-5-yl)ethane-1,2-diol (3.46 g, 20.3 mmol) and imidazole (3.08 g, 44.7 mmol) was dissolved in methylene chloride (40 mL). The mixture was cooled to 0° C. and tert-butyldimethylsilyl chloride (3.48 g, 22.4 mmol) dissolved in methylene chloride (40 mL) was added. The reaction was stirred for 30 minutes at 0° C. and then reacted at room temperature overnight. The mixture was treated with water (200 mL) and extracted with methylene chloride (2×200 mL). The combined organic layers were dried over sodium sulfate and concentrated. The residue was purified by silica gel chromatography (0-50% EtOAc/hexane) to afford a colorless oil.

E) (s)-5-(1-Azido-2-(tert-butyldimethylsilyloxy)ethyl)-2-methoxypyrimidine

A mixture of (R)-2-(tert-butyldimethylsilyloxy)-1-(2-methoxypyrimidin-5-yl)ethanol (4.4 g, 15 mmol) and diphenylphosphonic azide (16.7 mL, 77.3 mmol) was dissolved in toluene (53 mL). The mixture was cooled to 0° C. and neat 1,8-diazabicyclo[5.4.0]undec-7-ene (11.8 mL, 77.3 mmol) was added. The reaction was stirred for 30 minutes at 0° C. and then reacted at 60° C. overnight. The mixture was washed with water (50 mL) and 5% HCl (50 mL). The organic layer was concentrated in vacuo and purified by silica gel chromatography (0-25% EtOAc/hexane) to afford a colorless oil.

F) (S)-2-(tert-Butyldimethylsilyloxy)-1-(2-methoxypyrimidin-5-yl)ethanamine

A mixture of (S)-5-(1-azido-2-(tert-butyldimethylsilyloxy)ethyl)-2-methoxypyrimidine (11.7 g, 37.7 mmol) in ethyl acetate (300 mL), and 10% Pd—C (70 mg) was stirred under H$_2$ (1 atm) overnight. The catalyst was filtered off and the filtrate was concentrated to yield a light oil. The residue was purified by silica gel chromatography (0-50% MeOH/EtOAc) to afford a colorless oil.

Intermediates 15 and 16

(S)-1-(2-Methylpyrimidin-5-yl)ethanamine and (R)-1-(2-methylpyrimidin-5-yl)ethanamine

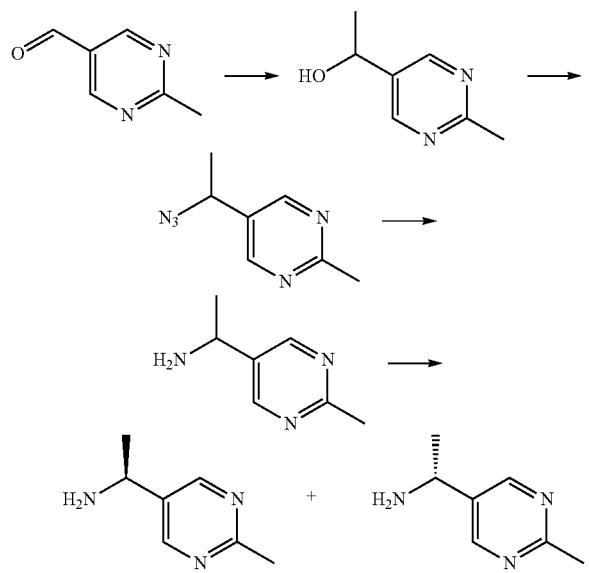

A) 2-methylpyrimidine-5-carbaldehyde

To a stirred slurry of acetamidine hydrochloride (19.4 g, 0.20 mol) and vinamidinium salt (48.91 g, 0.183 mol) in acetonitrile (240 mL) was added a solution of 40% wt. NaOH in water (27.4 g, 0.274 mol) over a 30 minutes period. After the addition was complete, the resulting reaction mixture was stirred at room temperature overnight. The mixture was concentrated in vacuo and diluted with water (250 mL) and extracted with EtOAc (3×250 mL). The combined organic layers were dried over sodium sulfate and concentrated in vacuo. The residue was purified by silica gel chromatography (0-100% EtOAc/hexanes) to afford a white solid.

B) 1-(2-methylpyrimidin-5-yl)ethanol

To a stirred solution of 2-methylpyrimidine-5-carbaldehyde (5.00 g, 38.9 mmol) in tetrahydrofuran (85 mL) was slowly added 33 µL of 1.4 M methylmagnesium bromide solution in tetrahydrofuran at 0° C. The mixture was stirred at room temperature for 1 hour and then quenched with water (50 mL) and extracted with EtOAc (3×200 mL). The combined organic layers were dried over sodium sulfate and concentrated in vacuo. The residue was purified by silica gel chromatography (0-100% EtOAc/hexane) to afford a colorless oil.

C) 5-(1-azidoethyl)-2-methylpyrimidine

To a stirred mixture of 1-(2-methylpyrimidin-5-yl)ethanol (2.48 g, 17 mmol) and diphenylphosphonic azide (9.3 mL, 41 mmol) in toluene (54.5 mL) at 0° C. was added neat 1,8-diazabicyclo[5.4.0]undec-7-ene (6.2 mL, 41 mmol). The reaction mixture was stirred at 0° C. for 30 minutes and then stirred at room temperature overnight. The mixture was diluted with EtOAc (100 mL) and washed with water (100 mL×2). The orangic layer was concentrated in vacuo and purified by silica gel chromatography (0-100% EtOAc/hexane) to afford a colorless oil.

D) 1-(2-methylpyrimidin-5-yl)ethanamine

A mixture of 5-(1-azidoethyl)-2-methylpyrimidine (2.20 g, 12.8 mmol), ethyl acetate (170 mL), and 10% palladium on carbon (1.32 g) was stirred under hydrogen (1 atm) overnight. The mixture was filtered and concentrated. The residue was purified by silica gel column (0-50% MeOH/EtOAc with 10% Et$_3$N) to afford a colorless oil.

$^1$H NMR (300 MHz, CD$_3$OD): δ 8.71 (s, 2H), 4.12 (q, 1H, J=6.6 Hz), 2.67 (s, 3H), 1.44 (d, J=6.6 Hz, 3H).

E) (S)-1-(2-methylpyrimidin-5-yl)ethanamine and (R)-1-(2-methylpyrimidin-5-yl)ethanamine Racemic 1-(2-methylpyrimidin-5-yl)ethanamine (2.78 g, 20.3 mmol) was resolved by chiral HPLC (sample preparation: sample was dissolved in 4 mL EtOH (heated) and 8 mL hexane was added). HPLC conditions: CHIRALPAK AD-H column at 0° C. [ice-bath], 20×250 mm, hexane/EtOH/Et$_2$NH [85:15:0.03] at 20 mL/min, UV detection at 230 nm) to yield (S)-1-(2-methylpyrimidin-5-yl)ethanamine (1.19 g, >99% ee) and (R)-1-(2-methylpyrimidin-5-yl)ethanamine (1.16 g, >99% ee).

Intermediate 17

(R)-3-Amino-3-(6-methylpyridin-3-yl)propan-1-ol

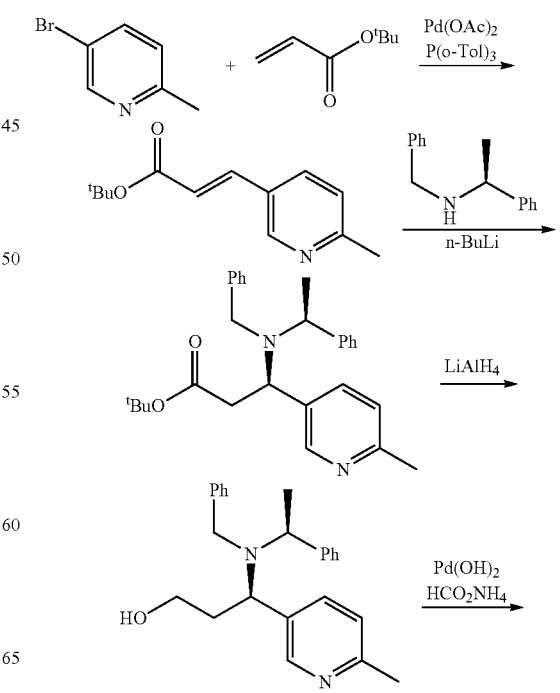

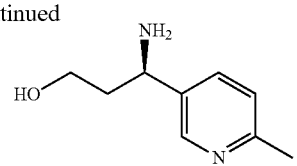

A) (E)-tert-butyl 3-(6-methylpyridin-3-yl)acrylate

To a solution of 5-bromo-2-methylpyridine (5 g, 29.06 mmol) in NMP (60 mL), were added Pd(OAc)$_2$ (0.325 g, 1.45 mmol) and P(o-tol)$_3$ (0.883 g, 2.9 mmol). Subsequently, a solution of tert-butyl acrylate (13.02 g, 101.7 mmol) in Et$_3$N (16.1 mL, 116.2 mmol) was added under N$_2$ to the above mixture and stirred at 90° C. After 16 h, water was added to the reaction mixture and extracted with Et$_2$O (3×). The combined organic phase was dried over anhydrous Na$_2$SO$_4$ and concentrated in vacuo to afford a residue. Purification of the residue by column chromatography (SiO$_2$, 100-200 mesh, Et$_2$O/Pet ether 1:9) afforded the title compound. MS: 220 [M+H]$^+$;

$^1$H NMR (300 MHz, CDCl$_3$): δ 8.6 (s, 1H), 7.7 (d, J=5.8 Hz, 1H), 7.5 (d, J=16.0 Hz, 1H), 7.1 (d, J=8.5 Hz, 1H), 6.4 (d, J=16.0 Hz, 1H), 2.6 (s, 3H) and 1.5 (s, 9H).

B) (R)-tert-butyl 3-(benzyl((S)-1-phenylethyl)amino)-3-(6-methylpyridin-3-yl)propanoate To a solution of (S)—N-benzyl-1-phenylethanamine (3.64 g, 17.26 mmol) in THF (40 mL) at −70° C., was added dropwise n-BuLi (1.6 M, 14.7 mmol) over a period of 30 min and stirred further. After 1 h, a solution of (E)-tert-butyl 3-(6-methylpyridin-3-yl)acrylate (2.7 g, 12.3 mmol) in THF was added slowly to the above mixture and stirred further. After 2 h, sat. NH$_4$Cl solution was added to the reaction mixture and extracted with EtOAc (3×). The combined organic phase was dried over anhydrous Na$_2$SO$_4$ and concentrated in vacuo to afford a residue. Purification of the residue by column chromatography (Neutral Al$_2$O$_3$, Et$_2$O/Pet ether 5:95) afforded the title compound.

MS: 431.6 [M+H]$^+$;

$^1$H NMR (300 MHz, CDCl$_3$): δ 8.5 (dd, J=2 Hz, 1H) 7.2-8.7 (m, 13H), 6.4 (d, J=16.0 Hz, 1H), 3.96 (t, J=6.8 Hz, 1H), 3.9 (q, J=6.8 Hz, 1H), 3.6 (s, 2H), 2.4-2.6 (m, 5H), 1.6 (s, 2H) and 1.2 (s, 9H).

C) (R)-3-(benzyl((S)-1-phenylethyl)amino)-3-(6-methylpyridin-3-yl)propan-1-ol To a solution of LiAlH$_4$ (1.24 g, 32.79 mmol) in THF (80 mL) at 0° C., was added dropwise a solution of (R)-tert-butyl 3-(benzyl((S)-1-phenylethyl)amino)-3-(6-methylpyridin-3-yl)propanoate (4.7 g, 10.93 mmol) in THF and was heated to 75° C. After 4 h, the reaction mixture was quenched with EtOAc and filtered. The filtrate was washed with excess EtOAc and dried under high vacuum to afford a residue. Purification of the residue by column chromatography (neutral Al$_2$O$_3$, Et$_2$O/Pet ether 15:85) afforded the title compound.

MS: 361.5 ([M−H]$^+$);

$^1$H NMR (300 MHz, CDCl$_3$): δ 7.2-8.5 (m, 13H), 4.0-4.1 (m, 2H), 3.4-3.6 (m, 3H), 3.3-3.4 (m, 1H), 2.6-2.7 (m, 3H), 2.0-2.2 (m, 3H) and 1.1 (d, J=5.6 Hz, 3H).

D) (R)-3-amino-3-(6-methylpyridin-3-yl)propan-1-ol

To a solution of (R)-3-(benzyl((S)-1-phenylethyl)amino)-3-(6-methylpyridin-3-yl)propan-1-ol (2.1 g, 5.83 mmol) in HPLC MeOH (40 mL), were added AcOH (0.34 mL, 5.8 mmol), Pd(OH)$_2$ (0.42 g) and HCOONH$_4$ (1.8 g, 29.16 mmol) and was heated to reflux. After 1 h, the reaction mixture was filtered through a Celite pad and the filtrate was concentrated in vacuo to afford a residue. Purification of the residue by column chromatography (neutral Al$_2$O$_3$, aq. NH$_3$/MeOH/CH$_2$Cl$_2$, 1:20:80) afforded the title compound.

$^1$H-NMR (300 MHz, CDCl$_3$): δ 7.2-8.4 (m, 3H), 4.2 (t, J=3.6 Hz, 1H), 3.8 (t, J=5.1 Hz, 2H), 2.6 (s, 3H), 2.2 (br, 3H) and 1.7-1.8 (m, 2H).

Intermediate 18

(S)-2-Amino-2-(4-(trifluoromethyl)phenyl)ethanol

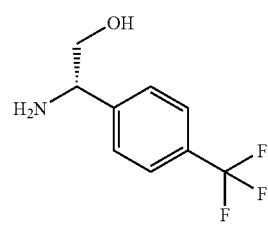

Lithium tetrahydroaluminate (0.62 g, 0.016 mol) was added slowly, in small portions, to an ice cooled mixture of 4-(trifluoromethyl)-L-phenylglycine (1.8 g, 8.2 mmol) in tetrahydrofuran (60 mL). The mixture was slowly warmed to rt over a period of 1 h and then heated to reflux overnight. The solution was cooled to 0° C. and quenched with 2.0 M aqueous NaOH solution. The precipitate was filtered off and the filter cake was washed with THF. The filtrate was concentrated and extracted with CH$_2$Cl$_2$ (50 mL×3). The combined organic layers were washed with brine, dried (Na$_2$SO$_4$), and concentrated in vacuo to give a light yellow solid (0.9 g, 59%). LC-MS: 206.2 [M+1]$^+$.

Intermediates 19 and 20

(R)-Cyclopropyl(6-(trifluoromethyl)pyridin-3-yl)methanamine and (S)-cyclopropyl(6-(trifluoromethyl)pyridin-3-yl)methanamine

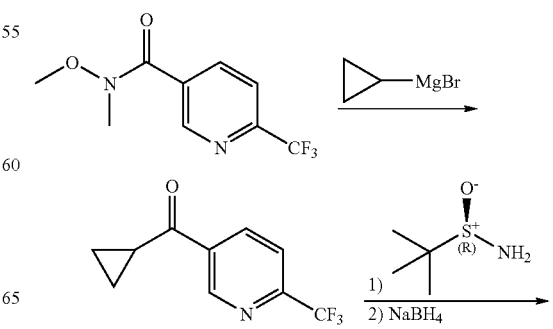

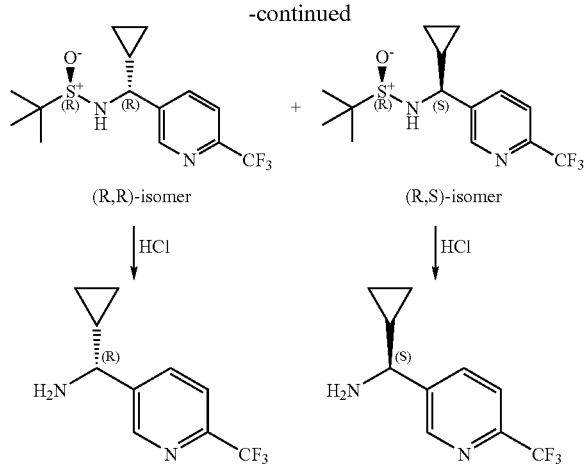

A) Cyclopropyl(6-(trifluoromethyl)pyridin-3-yl)
methanone

To a stirred solution of N-methoxy-N-methyl-6-(trifluoromethyl)nicotinamide (1.00 g, 4.27 mmol) in tetrahydrofuran (30 mL) at 0° C. was added 0.5 M of cyclopropylmagnesium bromide in tetrahydrofuran (20 μL, 0.01 mol) dropwise over 15 minutes. The mixture was stirred at 0° C. for 30 minutes then at room temperature overnight. The reaction was quenched with 1N HCl. Solvent was removed and the aqueous layer was extracted with ethyl acetate. Thr organic layers were combined and dried with MgSO₄, filtered and concentrated. The crude product was purified by silica gel column (0-60% ethyl acetate/hexane) to obtain a pale yellow solid.

B) (R)—N—((R)-Cyclopropyl(6-(trifluoromethyl)
pyridin-3-yl)methyl)-2-methylpropane-2-sulfinamide
and (R)—N—((S)-cyclopropyl(6-(trifluoromethyl)
pyridin-3-yl)methyl)-2-methylpropane-2-sulfinamide To a stirred solution of Ti(OEt)₄ (1.1 mL, 5.5 mmol) and cyclopropyl(6-(trifluoromethyl)pyridin-3-yl)methanone (0.84 g, 3.9 mmol) in tetrahydrofuran (20 mL) under N₂ was added (R)-2-methylpropane-2-sulfinamide (0.57 g, 4.7 mmol). The mixture was heated to 70° C. and heated overnight. The mixture was cooled to room temperature and then to −78° C. and cannulated slowly into a −78° C. solution of sodium tetrahydroborate (0.49 g, 13 mmol) in 20 mL of THF. The reaction was slowly warmed to room temperature and stirred overnight, and then quenched with methanol. The solution was filtered through Celite and the filter cake was washed with ethyl acetate. The filtrate was washed with brine, dried (Na₂SO₄), filtered, and concentrated. NMR showed about 10% S-isomer in the crude material (0.77 g, 62%). The diastereomers were separated by silica gel column (0-80% ethyl acetate/hexane). R,R-isomer (major) is less polar, while R,S-isomer is more polar.

C) (R)-Cyclopropyl(6-(trifluoromethyl)pyridin-3-yl)
methanamine (R)—N—((R)-Cyclopropyl(6-(trifluoromethyl)pyridin-3-yl)methyl)-2-methylpropane-2-sulfinamide (0.245 g, 0.000765 mol), ethanol (2.7 g, 0.059 mol), and 4.0 M of hydrogen chloride in dioxane (2.7 mL, 0.011 mol) were combined and stirred overnight. Reaction was concentrated to down to oil and then redissolved and washed with ethanol for 3 times, and concentrated. The residue was dried on the high vacuum overnight to obtain the title compound.

D) (S)-Cyclopropyl(6-(trifluoromethyl)pyridin-3-yl)
methanamine (S)—N—((R)-cyclopropyl(6-(trifluoromethyl)pyridin-3-yl)methyl)-2-methylpropane-2-sulfinamide (0.245 g, 0.000765 mol), ethanol (2.7 g, 0.059 mol), and 4.0 M of hydrogen chloride in dioxane (2.7 mL, 0.011 mol) are combined and stirred for 30 minutes. The mixture is allowed to stir overnight. The solvent is removed and the residue is dissolved in ethanol. After washing with ethanol for 3 times, the mixture is concentrated and the residue is dried under high vacuum overnight to obtain the title compound.

Intermediate 21

Quinolin-7-ylmethanamine

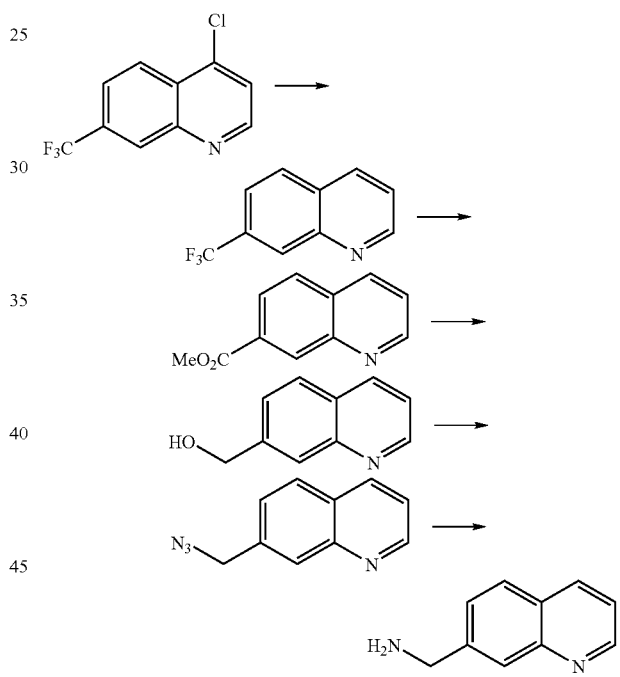

A) 7-(Trifluoromethyl)quinoline

4-Chloro-7-(trifluoromethyl)quinoline (9.35 g, 0.0404 mol) was hydrogenated in the presence of 5% palladium on carbon (4 g) in methanol (180 mL) in the presence of triethylamine (6 mL). The solution was stirred for 3.5 hours, and then filtered through Celite. The filtrate was concentrated under reduced pressure, and the residue was treated with ethyl acetate and water. The organic layer was separated, washed with water (2×75 mL), dried over MgSO₄, filtered, and concentrated under reduced pressure to a yellow solid.

B) Methyl quinoline-7-carboxylate 7-(Trifluoromethyl)quinoline (1 g, 5 mmol) was dissolved in 80% oleum (80:20, sulfuric acid:water, 50 mL), and the mixture was heated to 150° C. overnight. The solution was cooled to 0° C. and methanol (50 mL) was added slowly and the mixture was refluxed overnight. After cooling, the mixture was concentrated under reduced pressure to an oil and neutralized with saturated aqueous $Na_2CO_3$, and extracted with EtOAc (30 mL×3). The combined organic layers was dried with $MgSO_4$, and concentrated. The residue was purified by silica gel column to afford the title compound.

C) quinolin-7-ylmethanol

Methyl quinoline-7-carboxylate (5 g, 0.01 mol) was dissolved in tetrahydrofuran (40 mL) at −20° C. under an atmosphere of nitrogen. 60% REDAL (60:40, Red-Al(R):toluene, 6.53 mL, 0.0201 mol) was added and allowed to stir at −20° C. for 4 hours. After warming to room temperature, the reaction was quenched slowly with water, concentrated under reduced pressure, partitioned between EtOAc and water, and filtered through Celite. The aqueous phase was extracted with EtOAc. The combined organic layers were dried with $MgSO_4$, and concentrated under reduced pressure. The residue was purified by silica gel column to afford the title compound.

D) 7-(Azidomethyl)quinoline

A mixture of quinolin-7-ylmethanol (1.2 g, 7.2 mmol) and diphenylphosphonic azide (3.8 mL, 17 mmol) was dissolved in toluene (20 mL) and methylene chloride (6 mL). The mixture was cooled to 0° C. and neat 1,8-diazabicyclo[5.4.0]undec-7-ene (2.6 mL, 17 mmol) was added. The reaction was stirred for 30 minutes at 0° C. and then reacted at room temperature for 2 h. The mixture was diluted with $CH_2Cl_2$ (100 mL) and washed with water (100 mL×2). The organic layer was concentrated in vacuo and purified by silica gel chromatography (0-100% EtOAc/hexane) to afford a colorless oil.

E) Quinolin-7-ylmethanamine 7-(Azidomethyl)quinoline (1.1 g, 5.7 mmol) was hydrogenated (1 atm) in the presence of Raney nickel (1.5 g, 26 mmol) in methanol (30 mL) until completion of the reaction. Catalyst was filtered off and the filtrate was concentrated under reduced pressure to a yellow oil which was dissolved in EtOAc (32 mL) and extracted with 1N hydrochloric acid (3×32 mL). The combined acidic aqueous phases were adjust to pH~10 with 1N sodium hydroxide solution, and extracted with EtOAc (3×35 mL). The combined organic layers were dried over $MgSO_4$, filtered, and concentrated under reduced pressure to afford a white solid (0.89 g, 94%).

$^1$H NMR (300 MHz, $CD_3OD$) 8.83 (d, J=4.2 Hz, 1H), 8.36 (d, J=7.8 Hz, 1H), 7.97 (s, 1H), 7.94 (d, J=8.4 Hz, 1H), 7.64 (d, J=8.4 Hz, 1H), 7.52 (dd, J=7.8, 4.2 Hz, 1H), 4.05 (s, 2H).

Representative Methods

Method A (Compound 1)

5-Methyl-2-{4-[(6-trifluoromethyl-pyridin-3-ylmethyl)-amino]-7,8-dihydro-5H-pyrido[4,3-d]pyrimidin-6-yl}-benzonitrile

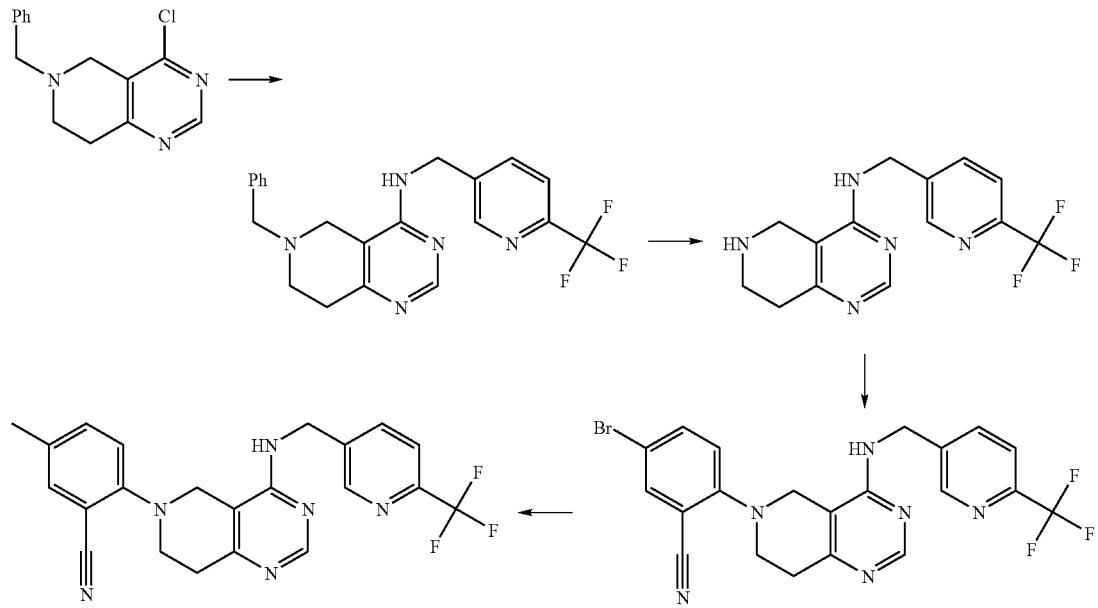

A) 6-Benzyl-N-((6-(trifluoromethyl)pyridin-3-yl)methyl)-5,6,7,8-tetrahydropyrido[4,3-d]pyrimidin-4-amine Two 20 mL microwave vials were each charged with a half portion of 6-benzyl-4-chloro-5,6,7,8-tetrahydropyrido[4,3-d]pyrimidine (5.62 g, 21.6 mmol), (6-(trifluoromethyl)pyridin-3-yl)methanamine (5.0 g, 28 mmol), N,N-diisopropylethylamine (7.6 mL, 44 mmol) and acetonitrile (10 mL), and the mixture was subjected to a microwave irradiation at 200° C. for 3.5 h. LC-MS analysis showed the reaction was complete for both samples. The samples were combined, and partitioned between CH$_2$Cl$_2$ (150 mL) and 0.5M NaH$_2$PO$_4$ (pH 4; 120 mL). The organic layer was extracted with 2M HCl (60 mL, 30 mL). The combined acid extracts were basified with 50% KOH (25 mL), extracted with CH$_2$Cl$_2$ (2×100 mL), dried (Na$_2$SO$_4$), filtered and concentrated to yield a light brown oil, which was absorbed on silica (40 g) and purified by column (120 g silica gel, 0-7.5% MeOH/CH$_2$Cl$_2$) to afford a light yellow foam (7.42 g, 86%).

LC-MS: 400.4 [M+H]$^+$ $^1$H NMR (400 MHz, CDCl$_3$): δ 8.67 (d, 1H, J=1.8 Hz), 8.45 (s, 1H), 7.83 (dd, 1H, J=8.0, 1.8 Hz), 7.62 (d, 1H, J=7.9 Hz), 7.39-7.27 (m, 5H), 4.79 (s, 2H), 3.77 (s, 2H), 3.31 (s, 2H), 2.90-2.80 (m, 4H).

B) N-((6-(Trifluoromethyl)pyridin-3-yl)methyl)-5,6,7,8-tetrahydropyrido[4,3-d]pyrimidin-4-amine A mixture of 6-benzyl-N-((6-(trifluoromethyl)pyridin-3-yl)methyl)-5,6,7,8-tetrahydropyrido[4,3-d]pyrimidin-4-amine (7.41 g, 18.6 mmol), methanol (300 mL), and 10% palladium on charcoal (1.0 g) was evacuated and purged with hydrogen 3 times, then hydrogenated (1 atm) at room temperature for 2 days. The mixture was filtered through a pad of Celite and the filter cake was washed with MeOH. The filtrate was concentrated in vacuo to yield a pale yellow foam (4.8 g).

LC-MS: 310.4 [M+H]$^+$

C) 5-Bromo-2-(4-((6-(trifluoromethyl)pyridin-3-yl)methylamino)-7,8-dihydropyrido[4,3-d]pyrimidin-6(5H)-yl)benzonitrile A mixture of N-((6-(trifluoromethyl)pyridin-3-yl)methyl)-5,6,7,8-tetrahydropyrido[4,3-d]pyrimidin-4-amine (1.0 g, 3.2 mmol), 5-bromo-2-fluorobenzonitrile (0.97 g, 4.8 mmol), N,N-diisopropylethylamine (1.7 mL, 9.7 mmol), and acetonitrile (10 mL) was subjected to microwave irradiation at 180° C. for 2 h. More 5-bromo-2-fluorobenzonitrile (1.0 g) was added and the mixture was subjected to microwave irradiation at 180° C. for another 2 h. Then additional 5-bromo-2-fluorobenzonitrile (1.0 g) was added and the reaction mixture was subjected to microwave irradiation at 180° C. for an additional 2 h. After cooling, the mixture was diluted with EtOAc (100 mL) and washed with aq. Na$_2$CO$_3$ solution and brine, dried (Na$_2$SO$_4$) and concentrated. The residue was purified by silica gel column (100% EtOAc) to yield a light yellow solid (0.90 g, 57%).

LC-MS: 491.1[M+H]$^+$ $^1$H NMR (400 MHz, d6-DMSO): δ 8.76 (s, 1H), 8.30 (s, 1H), 8.03 (d, 1H, J=2.4 Hz), 7.99 (d, 1H, J=8.8 Hz), 7.88 (dd, 1H, J=8.8, 2.4 Hz), 7.84 (d, 1H, J=8.0 Hz), 7.64 (t, 1H, J=5.6 Hz), 7.25 (d, 1H, J=8.8 Hz), 4.76 (d, 2H, J=5.6 Hz), 4.08 (s, 2H), 3.59 (t, 2H, J=5.6 Hz), 2.87 (t, 2H, J=5.6 Hz).

D) 5-Methyl-2-(4-((6-(trifluoromethyl)pyridin-3-yl)methylamino)-7,8-dihydropyrido[4,3-d]pyrimidin-6(5H)-yl)benzonitrile To a mixture of 5-bromo-2-(4-((6-(trifluoromethyl)pyridin-3-yl)methylamino)-7,8-dihydropyrido[4,3-d]pyrimidin-6(5H)-yl)benzonitrile (120 mg, 0.24 mmol), methylboronic acid (19 mg, 0.32 mmol), potassium phosphate (182 mg, 0.86 mmol), tricyclohexylphosphine (6.9 mg, 0.024 mmol), toluene (5 mL), and water (0.5 mL) under argon was added palladium acetate (2.8 mg, 0.012 mmol). The mixture was heated at 100° C. for 20 h and then cooled to rt. The mixture was filtered and concentrated. The residue was purified by semi-preparative HPLC to yield an off-white solid (75 mg, 71%).

LC-MS: 425.1 [M+H]$^+$ $^1$H NMR (400 MHz, d6-DMSO): δ 8.75 (s, 1H), 8.29 (s, 1H), 7.98 (d, 1H, J=8.0 Hz), 7.84 (d, 1H, J=8.0 Hz), 7.61 (t, 1H, J=5.6 Hz), 7.59 (d, 1H, J=1.6 Hz), 7.50 (dd, 1H, J=8.4, 1.6 Hz), 7.24 (d, 1H, J=8.4 Hz), 4.75 (d, 2H, J=5.6 Hz), 4.04 (s, 2H), 3.50 (t, 2H, J=5.6 Hz), 2.85 (t, 2H, J=5.6 Hz), 2.29 (s, 3H).

Method B (Compound 3)

5-Cyclopropyl-2-{4-[(6-trifluoromethyl-pyridin-3-ylmethyl)-amino]-7,8-dihydro-5H-pyrido[4,3-d]pyrimidin-6-yl}-benzonitrile

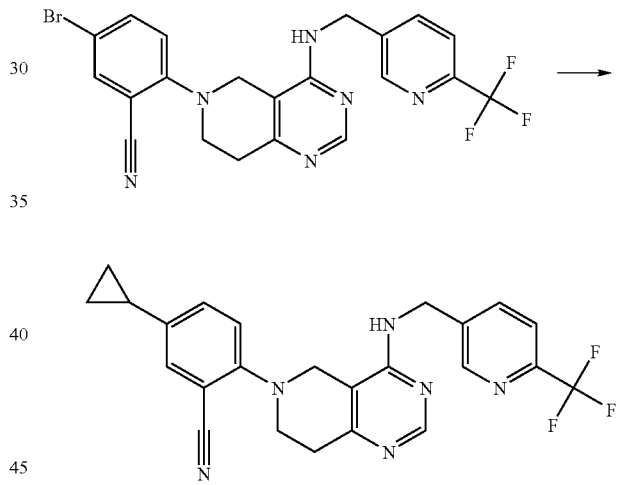

To a mixture of 5-bromo-2-(4-((6-(trifluoromethyl)pyridin-3-yl)methylamino)-7,8-dihydropyrido[4,3-d]pyrimidin-6(5H)-yl)benzonitrile (13 mg, 0.026 mmol), cyclopropylboronic acid (3.0 mg, 0.034 mmol), potassium phosphate (20 mg, 0.093 mmol), tricyclohexylphosphine (2.5 mg, 0.0090 mmol), toluene (2.0 mL), and water (0.04 mL) under argon was added palladium acetate (1.0 mg, 0.0044 mmol). The mixture was heated at 100° C. for 3 h and then cooled to rt. Water (10 mL) and EtOAc (100 mL) were added. The organic layer was separated and washed with brine, dried (Na$_2$SO$_4$), and concentrated. The residue was purified by semi-preparative HPLC to yield a white solid (7 mg, 58%).

LC-MS: 451.0 [M+H]$^+$ $^1$H NMR (400 MHz, d6-DMSO): δ 8.75 (s, 1H), 8.29 (s, 1H), 7.98 (d, 1H, J=8.0 Hz), 7.84 (d, 1H, J=8.0 Hz), 7.61 (t, 1H, J=5.6 Hz), 7.48 (d, 1H, J=2.4 Hz), 7.40 (dd, 1H, J=8.4, 2.4 Hz), 7.22 (d, 1H, J=8.4 Hz), 4.75 (d, 2H, J=5.6 Hz), 4.03 (s,

2H), 3.49 (t, 2H, J=5.6 Hz), 2.85 (t, 2H, J=5.6 Hz), 1.94 (m, 1H), 0.94 (m, 2H), 0.70 (m, 2H).

Method C (Compound 4)

5-Chloro-2-{4-[(6-trifluoromethyl-pyridin-3-ylmethyl)-amino]-7,8-dihydro-5H-pyrido[4,3-d]pyrimidin-6-yl}-benzonitrile

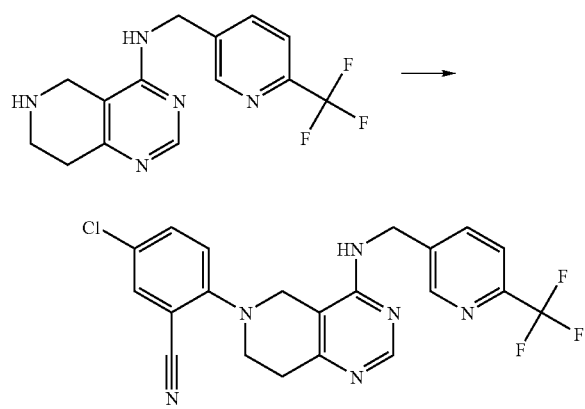

A 2 mL microwave vial was charged with N-((6-(trifluoromethyl)pyridin-3-yl)methyl)-5,6,7,8-tetrahydropyrido[4,3-d]pyrimidin-4-amine (50 mg, 0.16 mmol), 5-chloro-2-fluorobenzonitrile (150 mg, 0.97 mmol), acetonitrile (0.4 mL), and N,N-diisopropylethylamine (84 µL, 0.48 mmol). The mixture was subjected to a microwave irradiation at 200° C. for 2 h. The mixture was diluted with chloroform (7 mL), and washed with 0.1 M NaH$_2$PO$_4$ (10 mL), dried (Na$_2$SO$_4$), filtered and concentrated. The residue was purified by silica gel column to yield a light yellow solid (32 mg).

LC-MS: 445.3[M+H]$^+$ $^1$H NMR (400 MHz, d6-DMSO): δ 8.76 (s, 1H), 8.30 (s, 1H), 7.99 (dd, 1H, J=8.0, 1.6 Hz), 7.94 (d, 1H, J=2.8 Hz), 7.84 (d, 1H, J=8.0 Hz), 7.77 (dd, 1H, J=8.8, 2.8 Hz), 7.63 (t, 1H, J=5.6 Hz), 7.31 (d, 1H, J=8.8 Hz), 4.76 (d, 2H, J=5.6 Hz), 4.09 (s, 2H), 3.59 (t, 2H, J=5.6 Hz), 2.87 (t, 2H, J=5.6 Hz).

Method D (Compound 5)

5-Trifluoromethyl-2-{4-[(6-trifluoromethyl-pyridin-3-ylmethyl)-amino]-7,8-dihydro-5H-pyrido[4,3-d]pyrimidin-6-yl}-benzonitrile

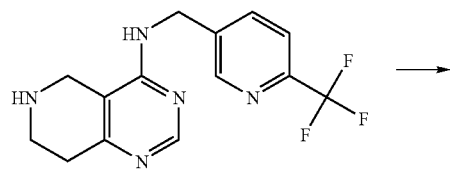

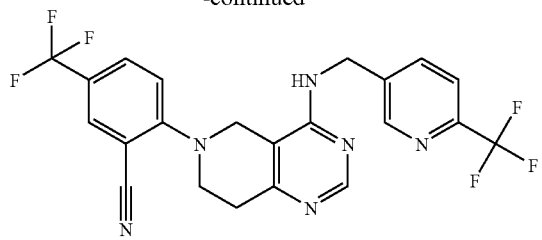

A 2 mL microwave vial was charged with N-((6-(trifluoromethyl)pyridin-3-yl)methyl)-5,6,7,8-tetrahydropyrido[4,3-d]pyrimidin-4-amine (40 mg, 0.13 mmol), 2-fluoro-5-(trifluoromethyl)benzonitrile (150 mg, 0.78 mmol), acetonitrile (0.4 mL) and N,N-diisopropylethylamine (68 µL, 0.39 mmol). The mixture was subjected to microwave irradiation at 200° C. for 2 h. The mixture was diluted with chloroform (7 mL), and washed with 0.1 M NaH$_2$PO$_4$ (10 mL), dried (Na$_2$SO$_4$), filtered and concentrated. The residue was purified by silica gel column to yield a pale brown solid.

LC-MS: 479.3 [M+H]$^+$ $^1$H NMR (400 MHz, CD$_3$OD): δ 8.72 (s, 1H), 8.33 (s, 1H), 8.02 (d, 1H, J=8.0 Hz), 7.98 (d, 1H, J=2.0 Hz), 7.86 (dd, 1H, J=8.8, 2.0 Hz), 7.76 (d, 1H, J=8.0 Hz), 7.40 (d, 1H, J=8.8 Hz), 4.86 (s, 2H), 4.23 (s, 2H), 3.80 (t, 2H, J=5.6 Hz), 3.02 (t, 2H, J=5.6 Hz).

Method E (Compound 7)

5-Methyl-2-{4-[(R)-1-(6-trifluoromethyl-pyridin-3-yl)-ethylamino]-7,8-dihydro-5H-pyrido[4,3-d]pyrimidin-6-yl}-benzonitrile

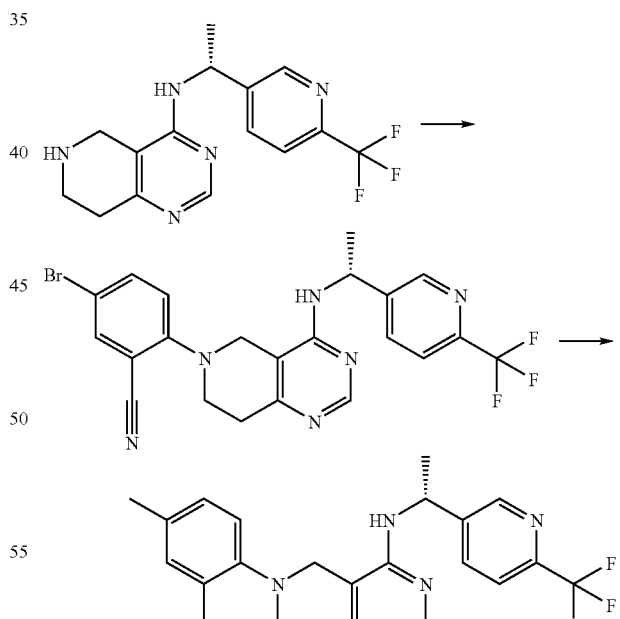

A) (R)-5-Bromo-2-(4-(1-(6-(trifluoromethyl)pyridin-3-yl)ethylamino)-7,8-dihydropyrido[4,3-d]pyrimidin-6(5H)-yl)benzonitrile A mixture of (R)—N-(1-(6-(trifluoromethyl)pyridin-3-yl)ethyl)-5,6,7,8-tetrahydropyrido[4,3-d]pyrimidin-4-amine (300 mg, 0.93 mmol), 5-bromo-2-fluorobenzonitrile (560 mg, 2.8 mmol), N,N-diisopropylethylamine (480 μL, 2.8 mmol), and acetonitrile (4 mL) was subjected to microwave irradiation at 180° C. for 2 h. More 5-bromo-2-fluorobenzonitrile (500 mg) was added and the mixture was subjected to microwave irradiation at 180° C. for another 2 h. Additional 5-bromo-2-fluorobenzonitrile (500 mg) was added and the mixture was subjected to microwave irradiation at 180° C. for an additional 2 h. LC-MS indicated the amine was nearly completely consumed. After cooling the mixture was concentrated in vacuo, and the residue was purified by silica gel column (100% EtOAc) to yield a light yellow solid (255 mg, 54%).

LC-MS: 505.0 [M+H]$^+$ $^1$H NMR (400 MHz, d6-DMSO): δ 8.82 (s, 1H), 8.25 (s, 1H), 8.07-8.04 (m, 2H), 7.89 (dd, 1H, J=8.8, 2.4 Hz), 7.84 (d, 1H, J=8.0 Hz), 7.33 (d, 1H, J=8.8 Hz), 7.24 (d, 1H, J=7.2 Hz), 5.50 (m, 1H), 4.17 and 4.07 (AB, 2H, J=15.6 Hz), 3.56 (m, 2H), 2.86 (t, 2H, J=5.6 Hz), 1.58 (d, 3H, J=7.2 Hz).

B) (R)-5-Methyl-2-(4-(1-(6-(trifluoromethyl)pyridin-3-yl)ethylamino)-7,8-dihydropyrido[4,3-d]pyrimidin-6(5H)-yl)benzonitrile To a mixture of (R)-5-bromo-2-(4-(1-(6-(trifluoromethyl)pyridin-3-yl)ethylamino)-7,8-dihydropyrido[4,3-d]pyrimidin-6(5H)-yl)benzonitrile (240 mg, 0.48 mmol), methylboronic acid (37.0 mg, 0.619 mmol), potassium phosphate (354 mg, 1.67 mmol), tricyclohexylphosphine (25 mg, 0.089 mmol), toluene (10 mL), and water (0.6 mL) under argon was added palladium acetate (10 mg, 0.04 mmol). The mixture was heated at 100° C. for 3 h and then cooled to rt. The mixture was filtered and concentrated. The residue was purified by semi-preparative HPLC to yield a light yellow solid (145 mg, 69%).

LC-MS: 439.2 [M+H]$^+$ $^1$H NMR (400 MHz, d6-DMSO): δ 8.81 (d, 1H, J=2.0 Hz), 8.24 (s, 1H), 8.05 (dd, 1H, J=8.0, 2.0 Hz), 7.84 (d, 1H, J=8.0 Hz), 7.60 (d, 1H, J=1.6 Hz), 7.52 (dd, 1H, J=8.4, 1.6 Hz), 7.31 (d, 1H, J=8.4 Hz), 7.22 (d, 1H, J=7.2 Hz), 5.50 (m, 1H), 4.13 and 4.03 (AB, 2H, J=15.6 Hz), 3.48 (m, 2H), 2.84 (t, 2H, J=5.6 Hz), 2.30 (s, 3H), 1.58 (d, 3H, J=7.2 Hz).

Method F (Compound 8)

(R)-5-Chloro-2-(4-(1-(6-(trifluoromethyl)pyridin-3-yl)ethylamino)-7,8-dihydropyrido[4,3-d]pyrimidin-6(5H)-yl)benzonitrile

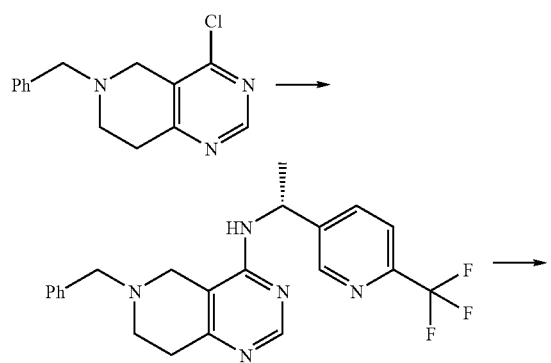

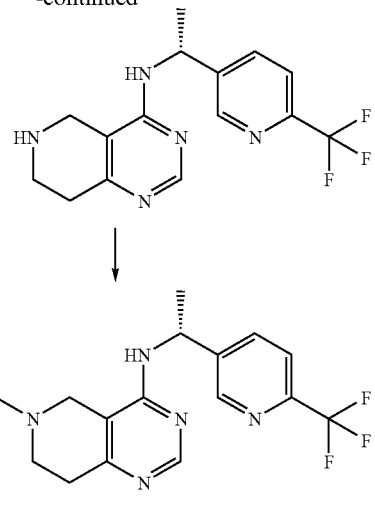

A) (R)-6-Benzyl-N-(1-(6-(trifluoromethyl)pyridin-3-yl)ethyl)-5,6,7,8-tetrahydropyrido[4,3-d]pyrimidin-4-amine 6-Benzyl-4-chloro-5,6,7,8-tetrahydropyrido[4,3-d]pyrimidine (5.00 g, 19.2 mmol), (R)-1-(6-(trifluoromethyl)pyridin-3-yl)ethanamine (4.76 g, 25.0 mmol), N,N-diisopropylethylamine (6.71 mL, 38.5 mmol), and acetonitrile (15 mL) were divided evenly between two 20 mL microwave vials. The reactions were subjected to microwave irradiation at 200° C. for 3.5 h. The two reactions were mixed together and evaporated the acetonitrile off. The residue was redissolved in CH$_2$Cl$_2$ (150 mL) and washed with 1M NaH$_2$PO$_4$ (2×50 mL). The product was extracted with 1M HCl (2×50 mL). The aqueous extracts were basified to pH 14 and extracted with CH$_2$Cl$_2$ (2×50 mL). The combined organic layers were dried with Na$_2$SO$_4$, filtered and evaporated to produce a yellow to orange solid (7.21 g). The crude product was washed with ether (25 mL) by stirring the solids for about 30 minutes. The solids were filtered from the ether and washed with ether (2×5 mL) to obtain a pale yellow powder (3.55 g, 45% yield). The ether filtrate was absorbed onto silica and purified by column with MeOH/CH$_2$Cl$_2$ (0-10%) to yield more product (2.38 g, 30% yield; 75% combined yield).

LC-MS: 414.5 [M+H]$^+$ $^1$H NMR (400 MHz, CDCl$_3$): δ 8.72 (d, 1H, J=1.6 Hz), 8.37 (s, 1H), 7.80 (dd, 1H, J=8.4, 1.6 Hz), 7.62 (d, 1H, J=8.0 Hz), 7.42-7.28 (m, 5H), 5.47 (m, 1H), 4.43 (d, 1H, J=6.4 Hz), 3.79 and 3.75 (AB, 2H, J=13.2 Hz), 3.37 (t, 2H, J=14.8 Hz), 2.88-2.76 (m, 4H), 1.62 (d, 3H, J=6.8 Hz).

B) (R)—N-(1-(6-(Trifluoromethyl)pyridin-3-yl)ethyl)-5,6,7,8-tetrahydropyrido[4,3-d]pyrimidin-4-amine A mixture of (R)-6-benzyl-N-(1-(6-(trifluoromethyl)pyridin-3-yl)ethyl)-5,6,7,8-tetrahydropyrido[4,3-d]pyrimidin-4-amine (3.55 g, 8.59 mmol), 10% palladium on charcoal (740 mg), and methanol (60 mL) were stirred under hydrogen (1 atm) for 15 h. The catalyst was filtered off through Celite and the filter cake was washed with MeOH (3×30 mL). The filtrate was concentrated to obtain an off-white foam (2.74 g, 98% yield).

LC-MS: 324.5 [M+H]+;

¹H NMR (400 MHz, CDCl₃): δ 8.74 (d, 1H, J=1.6 Hz), 8.37 (s, 1H), 7.83 (dd, 1H, J=8.0, 1.6 Hz), 7.63 (d, 1H, J=8.0 Hz), 5.48 (m, 1H), 4.55 (d, 1H, J=6.8 Hz), 3.74 (s, 2H), 3.17 (t, 2H, J=6.0 Hz), 2.75 (t, 2H, J=6.0 Hz), 1.64 (d, 3H, J=6.8 Hz).

C) (R)-5-Chloro-2-(4-(1-(6-(trifluoromethyl)pyridin-3-yl)ethylamino)-7,8-dihydropyrido[4,3-d]pyrimidin-6(5H)-yl)benzonitrile A mixture of (R)—N-(1-(6-(trifluoromethyl)pyridin-3-yl)ethyl)-5,6,7,8-tetrahydropyrido[4,3-d]pyrimidin-4-amine (500 mg, 1.55 mmol), 5-chloro-2-fluorobenzonitrile (360 mg, 2.3 mmol), N,N-diisopropylethylamine (540 mL, 3.1 mmol), and acetonitrile (3.0 mL) was subjected to microwave irradiation at 180° C. for 2 h. Then more 5-chloro-2-fluorobenzonitrile (360 mg) was added and the mixture was subjected to microwave irradiation at 180° C. for another 2 h. After that an additional 5-chloro-2-fluorobenzonitrile (360 mg) was added and the mixture was subjected to microwave irradiation at 180° C. for an additional 2 h. After cooling the mixture was concentrated in vacuo and the residue was purified by silica gel column (0-100% EtOAc/hexane) and the obtained solid was washed with ether to yield an off-white solid (370 mg, 51%).

LC-MS: 459.1 [M+H]+

¹H NMR (400 MHz, d6-DMSO): δ 8.82 (d, 1H, J=2.0 Hz), 8.25 (s, 1H), 8.05 (dd, 1H, J=8.0, 2.0 Hz), 7.95 (d, 1H, J=2.4 Hz), 7.84 (d, 1H, J=8.0 Hz), 7.79 (dd, 1H, J=8.8, 2.4 Hz), 7.40 (d, 1H, J=8.8 Hz), 7.24 (d, 1H, J=7.2 Hz), 5.50 (m, 1H), 4.18 and 4.08 (AB, 2H, J=15.6 Hz), 3.57 (m, 2H), 2.86 (t, 2H, J=5.6 Hz), 1.58 (d, 3H, J=7.2 Hz).

Method G (Compound 9)

5-Fluoro-2-{4-[(6-trifluoromethyl-pyridin-3-ylmethyl)-amino]-7,8-dihydro-5H-pyrido[4,3-d]pyrimidin-6-yl}-benzonitrile

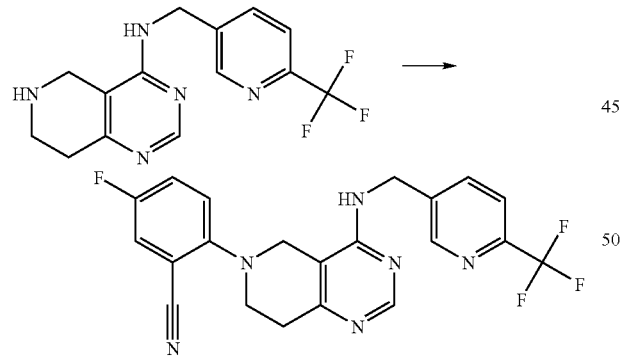

A 2 mL microwave vial was charged with N-((6-(trifluoromethyl)pyridin-3-yl)methyl)-5,6,7,8-tetrahydropyrido[4,3-d]pyrimidin-4-amine (50 mg, 0.16 mmol), 2,5-difluorobenzonitrile (130 mg, 0.97 mmol), acetonitrile (0.4 mL) and N,N-diisopropylethylamine (84 µL, 0.48 mmol). The mixture was subjected to microwave irradiation at 200° C. for 4 h. After cooling the mixture was diluted with chloroform (7 mL), and washed with 0.1 M NaH₂PO₄ (10 mL), dried (Na₂SO₄), filtered and concentrated. The residue was purified by semi-preparative HPLC (100×20.2 mm, C18 column; 20-90% MeCN/H₂O [10 mM diethylamine]) to yield an off-white solid (8 mg).

LC-MS: 429.6 [M+H]+

¹H NMR (400 MHz, CD₃OD): δ 8.70 (s, 1H), 8.32 (s, 1H), 8.00 (d, 1H, J=8.0 Hz), 7.75 (d, 1H, J=8.0 Hz), 7.51 (dd, 1H, J=8.0, 2.8 Hz), 7.45-7.39 (m, 1H), 7.34 (dd, 1H, J=9.2, 4.8 Hz), 4.84 (s, 2H), 4.08 (s, 2H), 3.56 (t, 2H, J=5.6 Hz), 2.98 (t, 2H, J=5.6 Hz).

Method H (Compound 11)

5-Chloro-2-(4-((2-methyl-6-(trifluoromethyl)pyridin-3-yl)methylamino)-7,8-dihydropyrido[4,3-d]pyrimidin-6(5H)-yl)benzonitrile

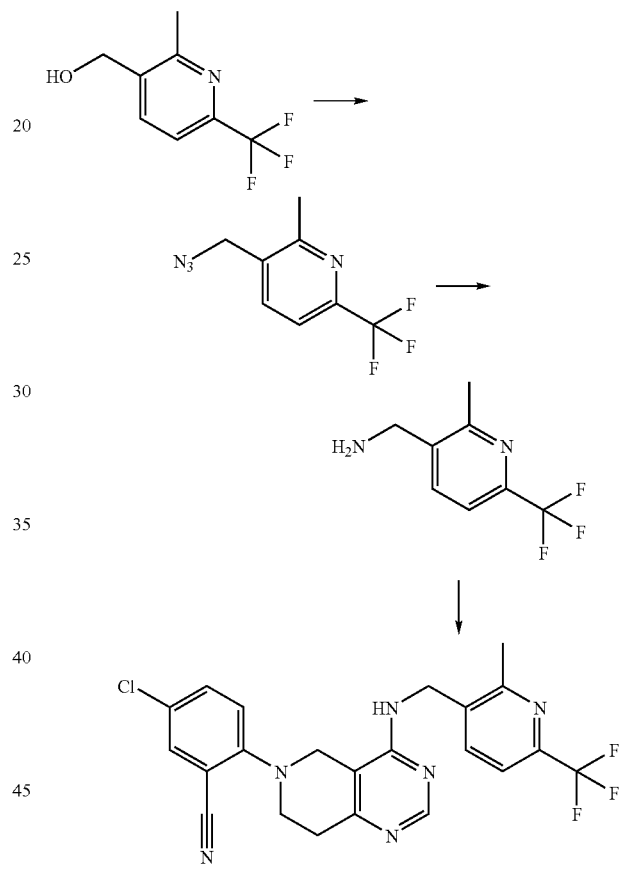

A) 3-(Azidomethyl)-2-methyl-6-(trifluoromethyl)pyridine

A 25 mL flask was charged with (2-methyl-6-(trifluoromethyl)pyridin-3-yl)methanol (287 mg, 1.50 mmol), tetrahydrofuran (5 mL) and diphenylphosphonic azide (356 µL, 1.65 mmol), purged with nitrogen, and cooled in ice. A solution of 1,8-diazabicyclo[5.4.0]undec-7-ene (236 µL, 1.57 mmol) in THF (1 mL) was added dropwise to the resultant mixture, and after 1.5 h, the mixture was warmed to room temperature and stirred overnight. Additional diphenylphosphonic azide (100 µL, 0.3 equiv.) was added followed by additional 1,8-diazabicyclo[5.4.0]undec-7-ene (90 µL, 0.4 equiv.), and the mixture was again stirred overnight. The reaction was quenched with 1M NaOH (20 mL), and poured into chloroform (20 mL). The organic layer was washed with 1M Na₂HPO₄ (pH 8, 2×15 mL), dried (Na₂SO₄), filtered and concentrated to a yellow oil which was purified by silica gel column (0-25% ethyl acetate/hexane) to yield a colorless oil (301 mg, 93%).

B) (2-Methyl-6-(trifluoromethyl)pyridin-3-yl)methanamine

To a stirred solution of 3-(azidomethyl)-2-methyl-6-(trifluoromethyl)pyridine (292 mg, 1.35 mmol) in tetrahydrofuran (5 mL) was added triphenylphosphine (710 mg, 2.7 mmol), and the mixture was stirred to dissolution. After 5 min the mixture was placed in an oil bath at 50° C. and stirred overnight. The mixture was hydrolyzed with 2M HCl (3 µL) for 0.5 h, then partitioned between ethyl acetate (30 mL) and 0.5 M NaH$_2$PO$_4$ (30 mL). The organic phase was extracted with 0.5 M NaH$_2$PO$_4$ (10 mL), and the combined acidic aqueous extracts were basified with 50% KOH, and extracted with CH$_2$Cl$_2$ (2×30 mL). The combined CH$_2$Cl$_2$ layers were dried (Na$_2$SO$_4$), filtered and concentrated to a faintly yellow semi-solid (0.53 g). NMR and LC-MS showed that the material was only partially cleaved to the free amine (40%) with the remaining 60% being the phospinimine. The mixture was dissolved in MeOH (10 mL) and heated at reflux for 2 h. The mixture was concentrated in vacuo and the residue was treated with water (10 mL) and 6N HCl to pH<1, and ether (20 mL). The aqueous phase was separated and extracted with ether (20 mL). The aqueous layer was adjusted to pH>13 with 2N aq. KOH and extracted with CH$_2$Cl$_2$ (3×50 mL). The combined organic layers were washed with brine, dried (Na$_2$SO$_4$), and concentrated to yield an oil which was used for the next step reaction without further purification.

LC-MS: 191.0 [M+H]$^+$; $^1$H NMR (400 MHz, d6-DMSO): δ 8.01 (d, 1H, J=8.0 Hz), 7.70 (d, 1H, J=8.0 Hz), 3.80 (s, 2H), 2.5 (s, 3H), 1.95 (bs, 2H).

C) 5-Chloro-2-(4-((2-methyl-6-(trifluoromethyl) pyridin-3-yl)methylamino)-7,8-dihydropyrido[4,3-d] pyrimidin-6(5H)-yl)benzonitrile A mixture of 2-methyl-6-(trifluoromethyl)pyridin-3-yl)methanamine (39.2 mg, 0.206 mmol), 2-(4-bromo-7,8-dihydropyrido[4,3-d]pyrimidin-6(5H)-yl)-5-chlorobenzonitrile (60 mg, 0.17 mmol), N,N-diisopropylethylamine (60 µL, 0.34 mmol) in acetonitrile (2.2 mL) was subjected to microwave irradiation at 180° C. for 6 hours. The reaction mixture was concentrated down to an oil and purified by semi-preparative HPLC (100×20.2 mm, C18 column; 20-80% CH$_3$CN-water [10 mM Et$_2$NH]) to obtain a white solid (35 mg).

LC-MS: 459.0 [M+H]$^+$ $^1$H NMR (400 MHz, d6-DMSO): δ 8.29 (s, 1H), 7.94 (d, 1H, J=2.8 Hz), 7.80 (d, 1H, J=8.4 Hz), 7.77 (dd, 1H, J=8.8, 2.8 Hz), 7.64 (d, H, J=8.0 Hz), 7.54 (t, 1H, J=5.6 Hz), 7.33 (d, 1H, J=8.8 Hz), 4.70 (d, 2H, J=5.6 Hz), 4.11 (s, 2H), 3.60 (t, 2H, J=5.6 Hz), 2.88 (t, 2H, J=5.6 Hz), 2.61 (s, 3H).

Method I (Compound 12)

5-Chloro-2-(4-((6-(dimethylamino)pyridin-3-yl)methylamino)-7,8-dihydropyrido[4,3-d]pyrimidin-6 (5H)-yl)benzonitrile

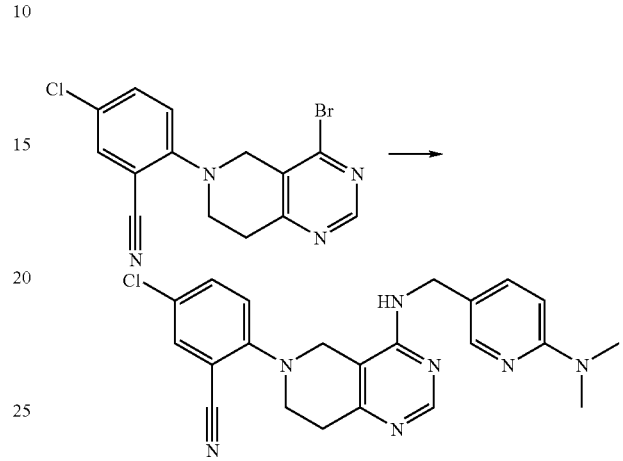

A mixture of 5-(aminomethyl)-N,N-dimethylpyridin-2-amine (24 mg, 0.16 mmol), 2-(4-bromo-7,8-dihydropyrido [4,3-d]pyrimidin-6(5H)-yl)-5-chlorobenzonitrile (50 mg, 0.14 mmol), and N,N-diisopropylethylamine (62 µL, 0.36 mmol) in acetonitrile (1.9 mL) was subjected to microwave irradiation at 180° C. for 6 hrs. The reaction mixture was concentrated to an oil which was purified by silica gel column (0-15% MeOH/CH$_2$Cl$_2$) to obtain a light yellow solid.

LC-MS: 420.5 [M+H]$^+$ $^1$H NMR (400 MHz, d6-DMSO): δ 8.33 (s, 1H), 8.07 (d, 1H, J=2.0 Hz), 7.93 (d, 1H, J=2.4 Hz), 7.75 (dd, 1H, J=8.8, 2.8 Hz), 7.49 (dd, 1H, J=8.4, 2.4 Hz), 7.35 (br, 1H), 7.31 (d, 1H, J=8.8 Hz), 6.58 (d, 1H, J=8.8 Hz), 4.49 (d, 2H, J=5.6 Hz), 3.99 (s, 2H), 3.56 (t, 2H, J=5.6 Hz), 2.97 (s, 6H), 2.84 (t, 2H, J=5.6 Hz).

Method J (Compound 13)

5-Chloro-2-(4-((6-methoxypyridin-3-yl)methylamino)-7,8-dihydropyrido[4,3-d]pyrimidin-6(5H)-yl)benzonitrile

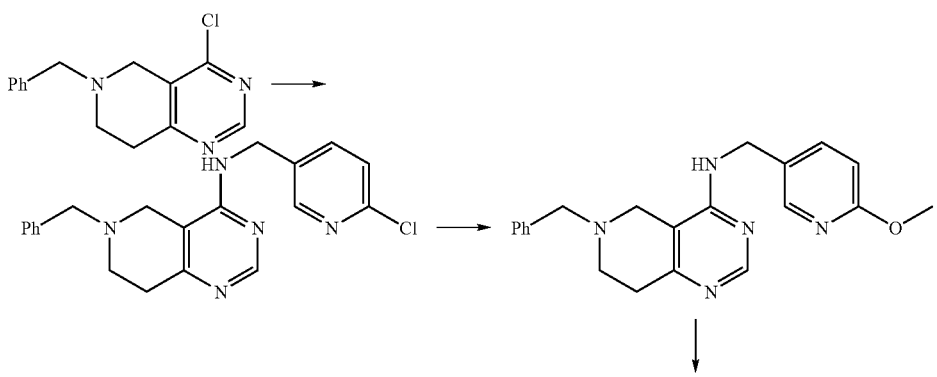

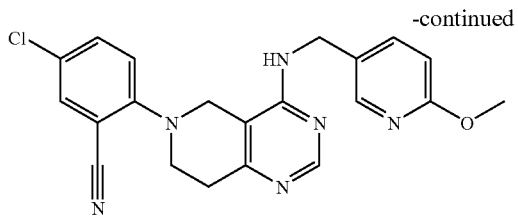
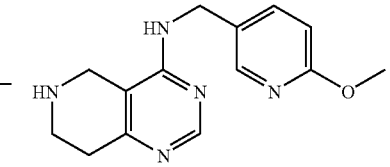

A) 6-Benzyl-N-((6-chloropyridin-3-yl)methyl)-5,6,7,8-tetrahydropyrido[4,3-d]pyrimidin-4-amine A mixture of 6-benzyl-4-chloro-5,6,7,8-tetrahydropyrido[4,3-d]pyrimidine (2.5 g, 9.6 mmol), 2-chloro-5-aminomethylpyridine (2.7 g, 19 mmol), acetonitrile (10 mL), and N,N-diisopropylethylamine (3.4 mL, 19 mmol) was subjected to microwave irradiation at 180° C. for 2 h. After standing at rt overnight, the precipitated solids were collected by filtration and washed with cold acetonitrile (5 mL×2), and dried to yield a yellow powder (2.8 g, 77%).

LC-MS: 366.3 [M+H]$^+$ $^1$H NMR (400 MHz, d6-DMSO): δ 8.34 (d, 1H, J=2.8 Hz), 8.23 (s, 1H), 7.74 (dd, 1H, J=8.4, 2.8 Hz), 7.45-7.25 (m, 7H), 4.56 (d, 2H, J=6.0 Hz), 3.72 (s, 2H), 3.36 (s, 2H), 2.72-2.62 (m, 4H).

B) 6-Benzyl-N-((6-methoxypyridin-3-yl)methyl)-5,6,7,8-tetrahydropyrido[4,3-d]pyrimidin-4-amine A mixture of 6-benzyl-N-((6-chloropyridin-3-yl)methyl)-5,6,7,8-tetrahydropyrido[4,3-d]pyrimidin-4-amine (2.5 g, 6.8 mmol), MeOH (5 mL), and 15% wt. sodium methoxide solution (10 g, 48 mmol) in MeOH was subjected to microwave irradiation at 150° C. for 60 min. The mixture was concentrated in vacuo and the residue was treated with water (50 mL) and extracted with CH$_2$Cl$_2$ (3×50 mL). The combined organic layers were washed with brine, dried (Na$_2$SO$_4$), and concentrated. The residue was purified by silica gel column (MeOH/CH$_2$Cl$_2$: 0-15%) to yield a yellow solid (2.0 g, 79%).

LC-MS: 362.3 [M+H]$^+$ $^1$H NMR (400 MHz, d6-DMSO): δ 0.24 (s, 1H), 8.09 (d, 1H, J=2.0 Hz), 7.62 (dd, 1H, J=8.4, 2.4 Hz), 7.40-7.19 (m, 6H), 6.74 (d, 1H, J=8.4 Hz), 4.48 (d, 2H, J=5.6 Hz), 3.80 (s, 3H), 3.70 (s, 2H), 3.32 (s, 2H), 2.70-2.60 (m, 4H).

C) N-((6-Methoxypyridin-3-yl)methyl)-5,6,7,8-tetrahydropyrido[4,3-d]pyrimidin-4-amine A mixture of 6-benzyl-N-((6-methoxypyridin-3-yl)methyl)-5,6,7,8-tetrahydropyrido[4,3-d]pyrimidin-4-amine (1.90 g, 5.26 mmol), MeOH (100 mL), and 10% Pd—C (600 mg) was hydrogenated at 1 atm for 3 days. LC-MS indicated complete conversion. Catalyst was filtered off and the filtrate was concentrated in vacuo to yield a light yellow foam.

LC-MS: 272.1 [M+H]+

D) 5-Chloro-2-(4-((6-methoxypyridin-3-yl)methylamino)-7,8-dihydropyrido[4,3-d]pyrimidin-6(5H)-yl)benzonitrile A mixture of N-((6-methoxypyridin-3-yl)methyl)-5,6,7,8-tetrahydropyrido[4,3-d]pyrimidin-4-amine (440 mg, 1.6 mmol), 5-chloro-2-fluorobenzonitrile (630 mg, 4.0 mmol), N,N-diisopropylethylamine (560 uL, 3.2 mmol), and acetonitrile (4.0 mL) was subjected to microwave irradiation at 180° C. for 4 h. After that an additional 5-chloro-2-fluorobenzonitrile (400 mg) was added and the mixture was subjected to microwave irradiation at 180° C. for another 2 h. After cooling, the mixture was treated with aq. NaHCO$_3$ and EtOAc (100 mL). The organic layer was separated, washed with brine, dried (Na$_2$SO$_4$), and concentrated in vacuo. The residue was purified by silica gel column (EtOAc: 100%) and the obtained solid was washed with ether to yield an off-white solid (290 mg, 44%).

LC-MS: 407.1 M+H]$^+$ $^1$H NMR (400 MHz, d6-DMSO): δ 8.32 (s, 1H), 8.15 (d, 1H, J=2.0 Hz), 7.93 (d, 1H, J=2.8 Hz), 7.75 (dd, 1H, J=9.2, 2.8 Hz), 7.67 (dd, 1H, J=8.4, 2.4 Hz), 7.44 (t, 1H, J=5.6 Hz), 7.31 (d, 1H, J=9.2 Hz), 6.76 (d, 1H, J=8.4 Hz), 4.57 (d, 2H, J=5.6 Hz), 4.02 (s, 2H), 3.81 (s, 3H), 3.57 (t, 2H, J=5.6 Hz), 2.85 (t, 2H, J=5.6 Hz).

Method K (Compound 14)

5-Bromo-2-(4-((6-methoxypyridin-3-yl)methylamino)-7,8-dihydropyrido[4,3-d]pyrimidin-6(5H)-yl)benzonitrile

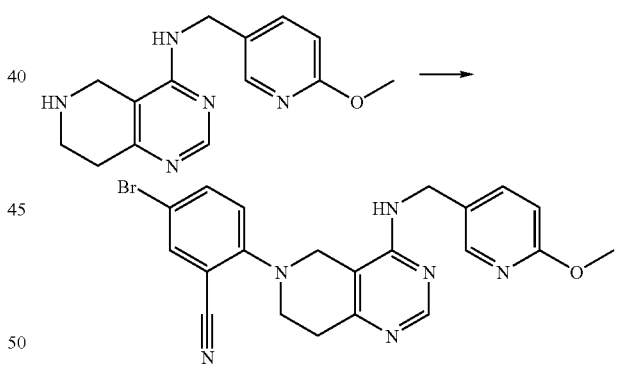

A mixture of N-((6-methoxypyridin-3-yl)methyl)-5,6,7,8-tetrahydropyrido[4,3-d]pyrimidin-4-amine (350 mg, 1.3 mmol), 5-bromo-2-fluorobenzonitrile (640 mg, 3.2 mmol), N,N-diisopropylethylamine (0.67 mL, 3.9 mmol), and acetonitrile (4 mL) was subjected to microwave irradiation at 180° C. for 3 h. After that additional 5-bromo-2-fluorobenzonitrile (450 mg) was added and the mixture was subjected to microwave irradiation at 180° C. for another 2 h. After cooling, the mixture was diluted with EtOAc (100 mL) and washed with aq. Na$_2$CO$_3$ solution and brine, dried (Na$_2$SO$_4$) and concentrated. The residue was purified by silica gel column (EtOAc: 100%) to yield a light yellow solid.

LC-MS: 453.1 [M+H]$^+$ $^1$H NMR (400 MHz, d6-DMSO): δ 8.32 (s, 1H), 8.14 (d, 1H, J=2.0 Hz), 8.02 (d, 1H, J=2.4 Hz), 7.86 (dd, 1H, J=9.2, 2.4

Hz), 7.67 (dd, 1H, J=8.4, 2.4 Hz), 7.44 (t, 1H, J=5.6 Hz), 7.24 (d, 1H, J=8.8 Hz), 6.76 (d, 1H, J=8.4 Hz), 4.57 (d, 2H, J=5.6 Hz), 4.01 (s, 2H), 3.81 (s, 3H), 3.57 (t, 2H, J=5.6 Hz), 2.85 (t, 2H, J=5.6 Hz).

Method L (Compound 15)

2-(4-((6-Methoxypyridin-3-yl)methylamino)-7,8-dihydropyrido[4,3-d]pyrimidin-6(5H)-yl)-5-methyl-benzonitrile

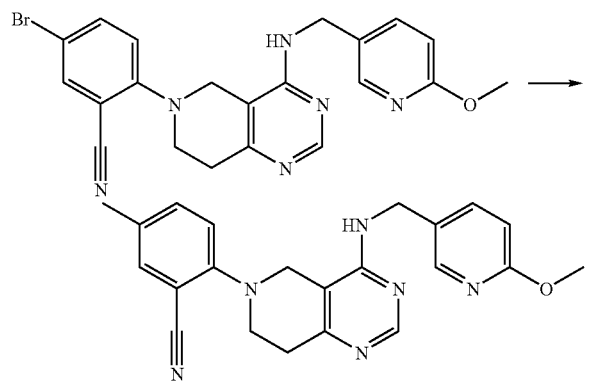

To a mixture of 5-bromo-2-(4-((6-methoxypyridin-3-yl)methylamino)-7,8-dihydropyrido[4,3-d]pyrimidin-6(5H)-yl)benzonitrile (55 mg, 0.12 mmol), methylboronic acid (18 mg, 0.30 mmol), potassium phosphate (90.6 mg, 0.427 mmol), tricyclohexylphosphine (6.8 mg, 0.024 mmol), toluene (3 mL), and water (0.2 mL) under argon was added palladium acetate (2.7 mg, 0.012 mmol). The mixture was heated at 100° C. for 3 h and then cooled to rt. The mixture was filtered through Celite and the filter cake was washed with EtOAc. The filtrate was concentrated and the residue was purified by preparative HPLC to yield an off-white solid.

LC-MS: 387.1 [M+H]$^+$ $^1$H NMR (400 MHz, d6-DMSO): δ 8.31 (s, 1H), 8.14 (d, 1H, J=2.0 Hz), 7.67 (dd, 1H, J=8.8, 2.4 Hz), 7.58 (d, 1H, J=1.2 Hz), 7.49 (dd, 1H, J=8.4, 1.6 Hz), 7.42 (t, 1H, J=5.6 Hz), 7.23 (d, 1H, J=8.8 Hz), 6.76 (d, 1H, J=8.8 Hz), 4.57 (d, 2H, J=5.6 Hz), 3.97 (s, 2H), 3.81 (s, 3H), 3.48 (t, 2H, J=5.6 Hz), 2.83 (t, 2H, J=5.6 Hz), 2.28 (s, 3H).

Method M (Compound 20)

5-Chloro-2-{4-[(R)-3-hydroxy-1-(6-trifluoromethyl-pyridin-3-yl)-propylamino]-7,8-dihydro-5H-pyrido[4,3-d]pyrimidin-6-yl}-benzonitrile

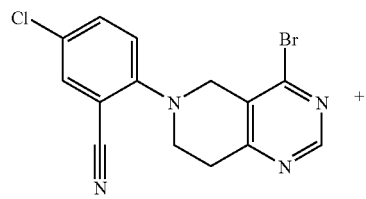

+

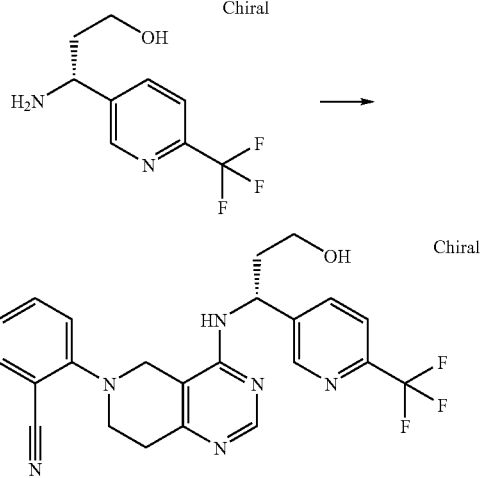

A reaction mixture of 2-(4-bromo-7,8-dihydropyrido[4,3-d]pyrimidin-6(5H)-yl)-5-chlorobenzonitrile (35 mg, 0.10 mmol) and (R)-3-amino-3-(6-(trifluoromethyl)pyridin-3-yl)propan-1-ol (22 mg, 0.10 μmol) in acetonitrile (1 mL) and N,N-diisopropylethylamine (0.035 mL, 0.20 mmol) was subjected to microwave irradiation at 200° C. for 2 h. The reaction mixture was concentrated and the residue was purified by preparative HPLC (100×20.2 mm, C18 column; 30-70% CH$_3$CN-water [10 mM Et$_2$NH]) to yield an off-white solid.

LC-MS: 489.2 [M+H]$^+$ $^1$H NMR (400 MHz, d6-DMSO): δ 8.80 (s, 1H), 8.24 (s, 1H), 8.05 (d, 1H, J=8.4 Hz), 7.96 (d, 1H, J=2.8 Hz), 7.85 (d, 1H, J=8.4 Hz), 7.79 (dd, 1H, J=8.8, 2.4 Hz), 7.39 (d, 1H, J=8.8 Hz), 7.23 (d, 1H, J=7.6 Hz), 5.52 (m, 1H), 4.68 (t, 1H, J=4.8 Hz), 4.18 and 4.07 (AB, 2H, J=15.6 Hz), 3.60-3.40 (m, 4H), 2.85 (m, 2H), 2.12 (m, 1H), 1.97 (m, 1H).

Method N (Compound 21)

2-{4-[(R)-3-Hydroxy-1-(6-methyl-pyridin-3-yl)-propylamino]-7,8-dihydro-5H-pyrido[4,3-d]pyrimidin-6-yl}-5-methyl-benzonitrile

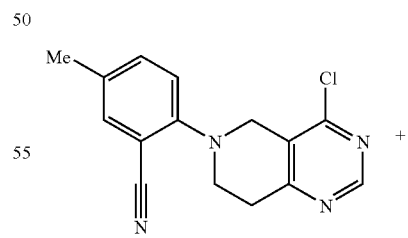

+

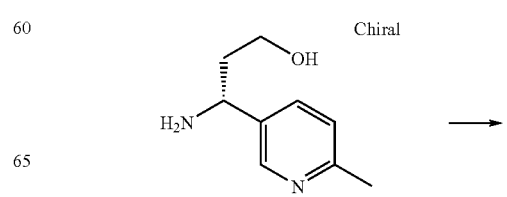

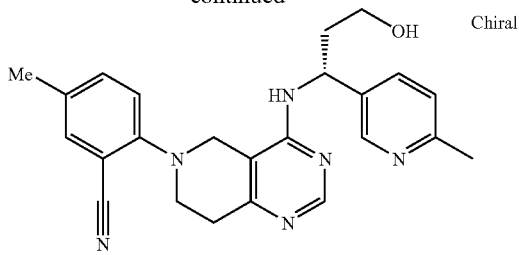

A reaction mixture of 2-(4-chloro-7,8-dihydropyrido[4,3-d]pyrimidin-6(5H)-yl)-5-methylbenzonitrile (60 mg, 0.21 mmol) and (R)-3-amino-3-(6-methylpyridin-3-yl)propan-1-ol (35 mg, 0.21 mmol) in acetonitrile (2 mL) and N,N-diisopropylethylamine (73 µL, 0.42 mmol) was subjected to microwave irradiation at 180° C. for 3 h. The reaction mixture was concentrated and the residue was purified by silica gel column (0-30% MeOH/CH$_2$Cl$_2$) followed by preparative HPLC (100×20.2 mm, C18 column; 20-50% CH$_3$CN-water [10 mM Et$_2$NH]) to yield an off-white solid (29 mg).

LC-MS: 415.5 [M+H]$^+$ $^1$H NMR (400 MHz, d6-DMSO): δ 8.45 (d, 1H, J=1.6 Hz), 8.23 (s, 1H), 7.65 (dd, 1H, J=8.0, 2.4 Hz), 7.60 (d, 1H, J=1.6 Hz), 7.52 (dd, 1H, J=8.4, 1.6 Hz), 7.31 (d, 1H, J=8.4 Hz), 7.16 (d, 1H, J=8.0 Hz), 7.07 (d, 1H, J=8.0 Hz), 5.40 (m, 1H), 4.61 (t, 1H, J=4.8 Hz), 4.07 and 3.99 (AB, 2H, J=15.6 Hz), 3.53-3.38 (m, 4H), 2.82 (m, 2H), 2.40 (s, 3H), 2.30 (s, 3H), 2.08 (m, 1H), 1.91 (m, 1H).

Method O (Compound 30)

2-{4-[(5-Cyclopropyl-pyridin-2-ylmethyl)-amino]-7,8-dihydro-5H-pyrido[4,3-d]pyrimidin-6-yl}-5-methyl-benzonitrile

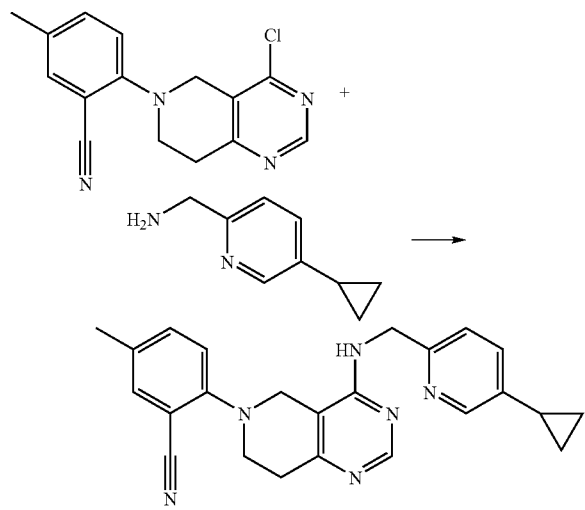

A reaction mixture of 2-(4-chloro-7,8-dihydropyrido[4,3-d]pyrimidin-6(5H)-yl)-5-methylbenzonitrile (150 mg, 0.53 mmol) and (5-cyclopropylpyridin-2-yl)methanamine (115 mg, 0.78 mmol) in acetonitrile (2 mL) and N,N-diisopropylethylamine (0.14 mL, 0.78 mmol) was subjected to microwave irradiation at 180° C. for 2 h. The mixture was concentrated and the residue was purified by preparative HPLC (100×20.2 mm, C18 column; 50-70% CH$_3$CN-water [10 mM Et$_2$NH]) to yield an off-white foam.

LC-MS: 397.3 [M+H]$^+$ $^1$H NMR (400 MHz, d6-DMSO): δ 8.32 (d, 1H, J=2.0 Hz), 8.25 (s, 1H), 7.59 (d, 1H, J=1.2 Hz), 7.55-7.47 (m, 2H), 7.32 (dd, 1H, J=8.4, 2.0 Hz), 7.25 (d, 1H, J=8.4 Hz), 7.16 (d, 1H, J=8.0 Hz), 4.67 (d, 2H, J=5.6 Hz), 4.03 (s, 2H), 3.51 (t, 2H, J=5.6 Hz), 2.85 (t, 2H, J=5.6 Hz), 2.29 (s, 3H), 191 (m, 1H), 0.99-0.93 (m, 2H), 0.70-0.65 (m, 2H).

Method P (Compound 35)

5-Chloro-2-{4-[(S)-2-hydroxy-1-(6-methoxy-pyridin-3-yl)-ethylamino]-7,8-dihydro-5H-pyrido[4,3-d]pyrimidin-6-yl}-benzonitrile

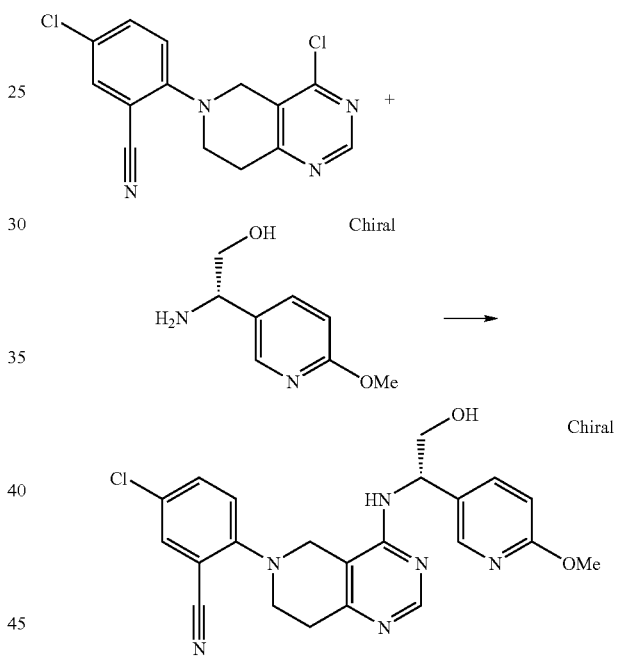

A reaction mixture of 5-chloro-2-(4-chloro-7,8-dihydropyrido[4,3-d]pyrimidin-6(5H)-yl)benzonitrile (250 mg, 0.82 mmol) and (S)-2-amino-2-(6-methoxypyridin-3-yl)ethanol (110 mg, 0.68 mmol) in acetonitrile (3 mL) and N,N-diisopropylethylamine (240 µL, 1.4 mmol) was subjected to microwave irradiation at 180° C. for 4 h. The reaction mixture was concentrated and the residue was purified by silica gel column (0-15% MeOH/CH$_2$Cl$_2$) to yield a crude product which was recrystallized from MeOH to yield colorless crystals.

LC-MS: 437.4 [M+H]$^+$ $^1$H NMR (400 MHz, d6-DMSO): δ 8.27 (s, 1H), 8.18 (d, 1H, J=2.4 Hz), 7.95 (d, 1H, J=2.4 Hz), 7.78 (dd, 1H, J=8.8, 2.4 Hz), 7.72 (dd, 1H, J=8.4, 2.4 Hz), 7.41 (d, 1H, J=8.8 Hz), 6.97 (d, 1H, J=8.0 Hz), 6.76 (d, 1H, J=8.4 Hz), 5.32 (m, 1H), 4.99

(t, 1H, J=6.0 Hz), 4.13 and 4.06 (AB, 2H, J=15.6 Hz), 3.81 (s, 3H), 3.80-3.63 (m, 2H), 3.56 (t, 2H, J=5.6 Hz), 2.84 (m, 2H).

Method Q (Compound 37)

2-{4-[(imidazo[1,2-a]pyridin-7-ylmethyl)-amino]-7,8-dihydro-5H-pyrido[4,3-d]pyrimidin-6-yl}-5-methyl-benzonitrile

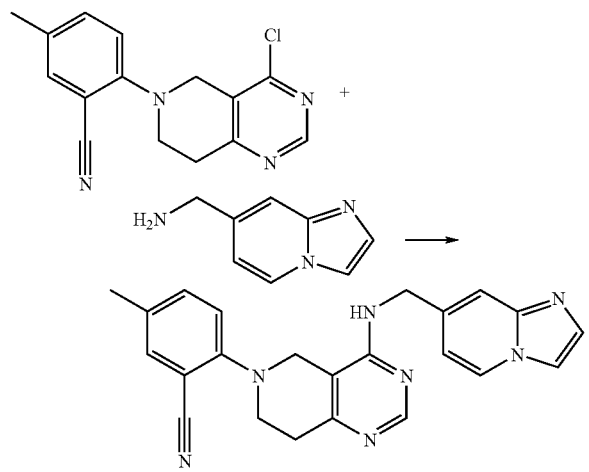

A reaction mixture of 2-(4-chloro-7,8-dihydropyrido[4,3-d]pyrimidin-6(5H)-yl)-5-methylbenzonitrile (300 mg, 1.05 mmol) and imidazo[1,2-a]pyridin-7-ylmethanamine (400 mg, 2.31 mmol) in acetonitrile (10 mL) and N,N-diisopropylethylamine (1.0 mL, 5.7 mmol) was subjected to microwave irradiation at 185° C. for 2.5 h. The reaction mixture was concentrated and purified by semi-preparative HPLC (100× 20.2 mm, C18 column; 30-60% CH$_3$CN-water [10 mM Et$_2$NH]) to yield a light yellow solid.

LC-MS: 396.4 [M+H]$^+$ $^1$H NMR (400 MHz, d6-DMSO): δ 8.46 (d, 1H, J=6.9 Hz), 8.30 (s, 1H), 7.87 (s, 1H), 7.59 (d, 1H, J=1.4 Hz), 7.54 (t, 1H, J=5.8 Hz), 7.50 (s, 1H), 7.48 (d, 1H, J=1.7 Hz), 7.38 (s, 1H), 7.25 (d, 1H, J=8.5 Hz), 6.86 (dd, 1H, J=7.0, 1.5 Hz), 4.67 (d, 2H, J=5.7 Hz), 4.05 (s, 2H), 3.52 (t, 2H, J=5.5 Hz), 2.86 (t, 2H, J=5.3 Hz), 2.29 (s, 3H).

Method R (Compound 38)

2-{4-[(Benzooxazol-5-ylmethyl)-amino]-7,8-dihydro-5H-pyrido[4,3-d]pyrimidin-6-yl}-5-methyl-benzonitrile

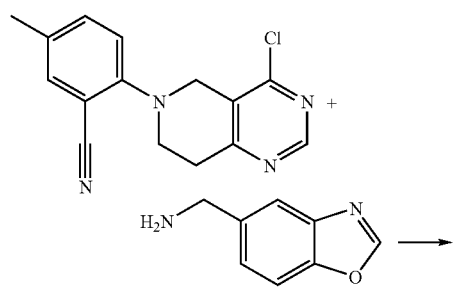

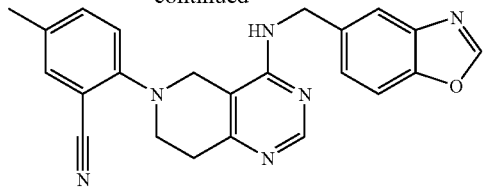

A reaction mixture of 2-(4-chloro-7,8-dihydropyrido[4,3-d]pyrimidin-6(5H)-yl)-5-methylbenzonitrile (100 mg, 0.35 mmol) and benzo[d]oxazol-5-ylmethanamine (150 mg, 0.41 mmol) in acetonitrile (3 mL) and N,N-diisopropylethylamine (0.37 mL, 2.1 mmol) was subjected to microwave irradiation at 185° C. for 2.5 h. The reaction mixture was concentrated and purified by preparative HPLC (100×20.2 mm, C18 column; 30-60% CH$_3$CN-water [10 mM Et$_2$NH]) to yield a light yellow solid.

LC-MS: 397.4 [M+H]$^+$ $^1$H NMR (400 MHz, d6-DMSO): δ 8.71 (s, 1H), 8.30 (s, 1H), 7.75 (d, 1H, J=0.9 Hz), 7.70 (d, 1H, J=8.4 Hz), 7.58 (d, 1H, J=1.5 Hz), 7.55 (t, 1H, J=5.9 Hz), 7.49 (dd, 1H, J=8.5, 1.7 Hz), 7.42 (dd, 1H, J=8.4, 1.5 Hz), 7.25 (d, 1H, J=8.5 Hz), 4.77 (d, 2H, J=5.8 Hz), 4.02 (s, 2H), 3.51 (t, 2H, J=5.6 Hz), 2.85 (t, 2H, J=5.4 Hz), 2.29 (s, 3H).

Method S (Compound 39)

5-Methyl-2-{4-[(2-methyl-pyrimidin-5-ylmethyl)-amino]-7,8-dihydro-5H-pyrido[4,3-d]pyrimidin-6-yl}-benzonitrile

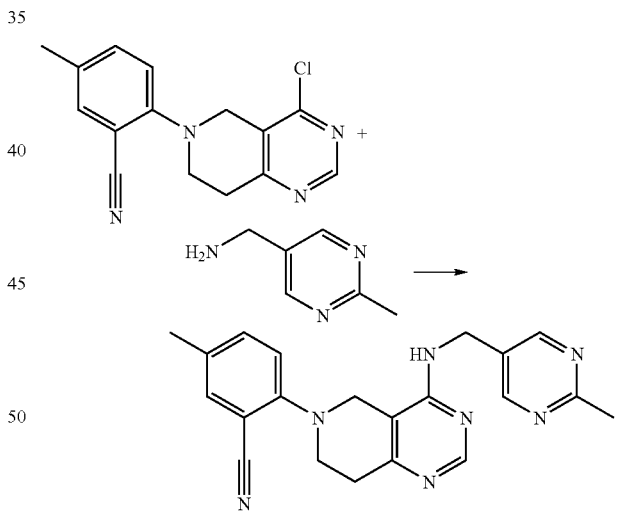

A reaction mixture of 2-(4-chloro-7,8-dihydropyrido[4,3-d]pyrimidin-6(5H)-yl)-5-methylbenzonitrile (400 mg, 1.41 mmol) and (2-methylpyrimidin-5-yl)methanamine (400 mg, 3.25 mmol) in acetonitrile (3 mL) and N,N-diisopropylethylamine (1.5 mL, 8.6 mmol) was subjected to microwave irradiation at 185° C. for 2.5 h. The reaction mixture was concentrated and purified by preparative HPLC (100×20.2 mm, C18 column; 40-60% CH$_3$CN-water [10 mM Et$_2$NH]) to yield a light brown solid.

LC-MS: 372.2 [M+H]$^+$ $^1$H NMR (400 MHz, d6-DMSO): δ 8.66 (s, 2H), 8.32 (s, 1H), 7.59 (d, 1H, J=1.5 Hz), 7.50 (d, 1H, J=2.4 Hz), 7.48 (d,

1H, J=1.3 Hz), 7.23 (d, 1H, J=8.5 Hz), 4.60 (d, 2H, J=5.6 Hz), 4.00 (s, 2H), 3.49 (t, 2H, J=5.6 Hz), 2.85 (t, 2H, J=5.4 Hz), 2.57 (s, 3H), 2.29 (s, 3H).

Method T (Compound 44)

5-Chloro-2-{4-[(imidazo[1,2-a]pyridin-7-ylmethyl)-amino]-7,8-dihydro-5H-pyrido[4,3-d]pyrimidin-6-yl}-benzonitrile

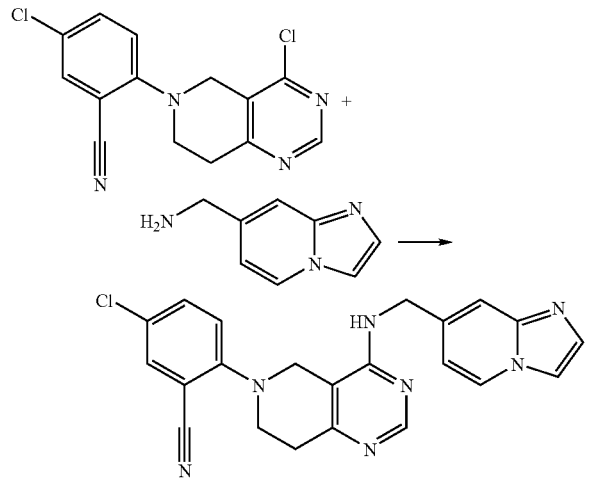

A reaction mixture of 5-chloro-2-(4-chloro-7,8-dihydro-pyrido[4,3-d]pyrimidin-6(5H)-yl)benzonitrile (250 mg, 0.82 mmol) and imidazo[1,2-a]pyridin-7-ylmethanamine (270 mg, 1.83 mmol) in acetonitrile (10 mL) and N,N-diisopropylethylamine (1.0 mL, 5.7 mmol) was subjected to microwave irradiation at 185° C. for 4 h. The reaction mixture was concentrated and purified by semi-preparative HPLC (100× 20.2 mm, C18 column; 40-60% CH₃CN-water [10 mM Et₂NH]) to yield a light yellow solid.

LC-MS: 416.4 [M+H]⁺

¹H NMR (400 MHz, d6-DMSO): δ 8.47 (d, 1H, J=7.0 Hz), 8.30 (s, 1H), 7.94 (d, 1H, J=2.6 Hz), 7.87 (s, 1H), 7.76 (dd, 1H J=8.9, 2.6 Hz), 7.56 (t, 1H, J=6.0 Hz), 7.50 (s, 1H), 7.36 (s, 1H), 7.33 (d, 1H, J=9.0 Hz), 6.87 (dd, 1H, J=7.0, 1.4 Hz), 4.68 (d, 2H, J=5.7 Hz), 4.10 (s, 2H), 3.60 (t, 2H, J=5.5 Hz), 2.88 (t, 2H, J=5.4 Hz).

Method U (Compound 46)

2-{4-[(S)-2-Hydroxy-1-(6-trifluoromethyl-pyridin-3-yl)-ethylamino]-7,8-dihydro-5H-pyrido[4,3-d]pyrimidin-6-yl}-5-methyl-benzonitrile

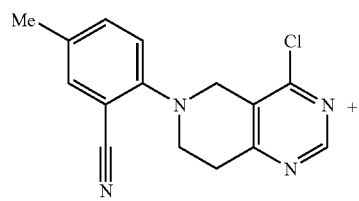

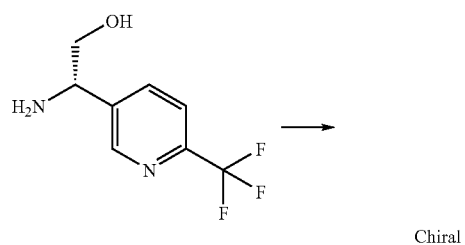

A reaction mixture of 2-(4-chloro-7,8-dihydropyrido[4,3-d]pyrimidin-6(5H)-yl)-5-methylbenzonitrile (160 mg, 0.56 mmol) and (S)-2-amino-2-(6-(trifluoromethyl)pyridin-3-yl)ethanol (118 mg, 0.57 mmol) (prepared similarly according to the method for Intermediate 10) in acetonitrile (2 mL) and N,N-diisopropylethylamine (0.4 mL) was subjected to microwave irradiation at 185° C. for 3.5 h. The reaction mixture was concentrated and the residue was purified by semi-preparative HPLC (100×20.2 mm, C18 column; 40-60% acetonitrile-water [10 mM diethylamine]) to yield a light brown solid.

LC-MS: 455.2 [M+H]⁺

¹H NMR (400 MHz, d6-DMSO): δ 8.81 (d, 1H, J=1.5 Hz), 8.25 (s, 1H), 8.07 (dd, 1H J=8.1, 1.7 Hz), 7.85 (d, 1H, J=8.1 Hz), 7.61 (d, 1H, J=1.5 Hz), 7.53 (dd, 1H, J=8.6, 1.8 Hz), 7.33 (d, 1H, J=8.5 Hz), 7.11 (d, 1H, J=7.5 Hz), 5.43 (q, 1H, J=6.8 Hz), 5.14 (t, 1H, J=5.9 Hz), 4.15 and 4.06 (AB, 2H, J=15.5 Hz), 3.88-3.70 (m, 2H), 3.49 (t, 2H, J=5.7 Hz), 2.85 (m, 2H), 2.30 (s, 3H).

Method V (Compound 47)

5-Chloro-2-{4-[(S)-2-hydroxy-1-(6-trifluoromethyl-pyridin-3-yl)-ethylamino]-7,8-dihydro-5H-pyrido[4,3-d]pyrimidin-6-yl}-benzonitrile

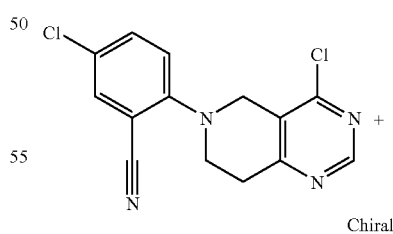

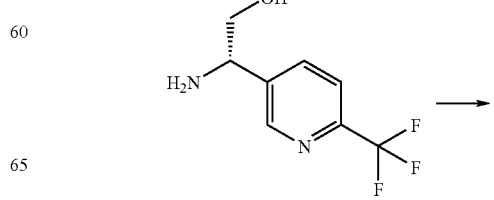

-continued

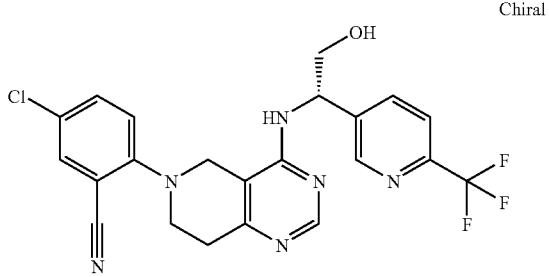

A reaction mixture of 5-chloro-2-(4-chloro-7,8-dihydro-pyrido[4,3-d]pyrimidin-6(5H)-yl)benzonitrile (150 mg, 0.49 mmol) and (S)-2-amino-2-(6-(trifluoromethyl)pyridin-3-yl)ethanol (150 mg, 0.74 mmol) (prepared similarly according to the method for Intermediate 10) in acetonitrile (3 mL) and N,N-diisopropylethylamine (170 μL, 0.98 mmol) was subjected to microwave irradiation at 180° C. for 4 h. The reaction mixture was concentrated and the residue was purified by silica gel column (100% EtOAc and then 0-20% MeOH/CH$_2$Cl$_2$) followed by semi-preparative HPLC (100×20.2 mm, C18 column; 30-70% acetonitrile-water [10 mM Et$_2$NH]) to yield a light yellow foam (44 mg).

LC-MS: 475.4 [M+H]$^+$ $^1$H NMR (400 MHz, d6-DMSO): δ 8.81 (d, 1H, J=1.6 Hz), 8.26 (s, 1H), 8.08 (dd, 1H, J=8.0, 1.6 Hz), 7.96 (d, 1H, J=2.8 Hz), 7.85 (d, 1H, J=7.6 Hz), 7.79 (dd, 1H, J=9.2, 2.8 Hz), 7.41 (d, 1H, J=9.2 Hz), 7.13 (d, 1H, J=7.6 Hz), 5.44 (q, 1H, J=6.8 Hz), 5.15 (t, 1H, J=5.6 Hz), 4.20 and 4.10 (AB, 2H, J=15.6 Hz), 3.87-3.74 (m, 2H), 3.57 (t, 2H, J=5.6 Hz), 2.86 (t, 2H, J=5.6 Hz).

Method W (Compound 51)

5-Chloro-2-[4-(3-[1,2,4]triazol-4-yl-benzylamino)-7,8-dihydro-5H-pyrido[4,3-d]pyrimidin-6-yl]-benzonitrile

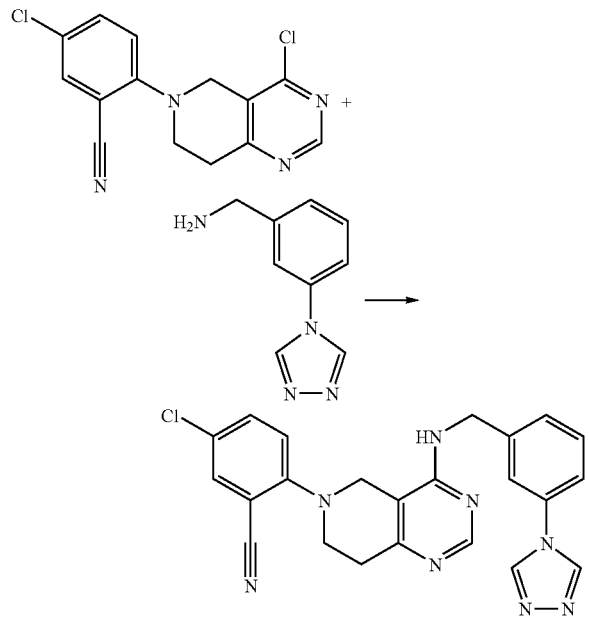

A reaction mixture of 5-chloro-2-(4-chloro-7,8-dihydro-pyrido[4,3-d]pyrimidin-6(5H)-yl)benzonitrile (80 mg, 0.26 mmol) and (3-(4H-1,2,4-triazol-4-yl)phenyl)methanamine (120 mg, 0.40 mmol) in acetonitrile (1 mL) and N,N-diisopropylethylamine (0.6 mL, 4 mmol) was subjected to microwave irradiation at 185° C. for 2.5 h. The reaction mixture was concentrated and purified by semi-preparative HPLC (100×20.2 mm, C18 column; 30-50% CH$_3$CN-water [10 mM Et$_2$NH]) to yield a light yellow solid.

LC-MS: 443.5 [M+H]$^+$ $^1$H NMR (400 MHz, d6-DMSO): δ 9.10 (s, 2H), 8.30 (s, 1H), 7.94 (d, 1H, J=2.6 Hz), 7.76 (dd, 1H, J=8.9, 2.6 Hz), 7.66 (s, 1H), 7.60-7.52 (m, 2H), 7.50 (t, 1H, J=7.8 Hz), 7.38 (d, 1H, J=7.6 Hz), 7.33 (d, 1H, J=9.0 Hz), 4.73 (d, 2H, J=5.7 Hz), 4.09 (s, 2H), 3.59 (t, 2H, J=5.5 Hz), 2.87 (t, 2H, J=5.4 Hz).

Method X (Compound 57)

5-Chloro-2-{4-[(R)-1-(2-methoxy-pyrimidin-5-yl)-ethylamino]-7,8-dihydro-5H-pyrido[4,3-d]pyrimidin-6-yl}-benzonitrile

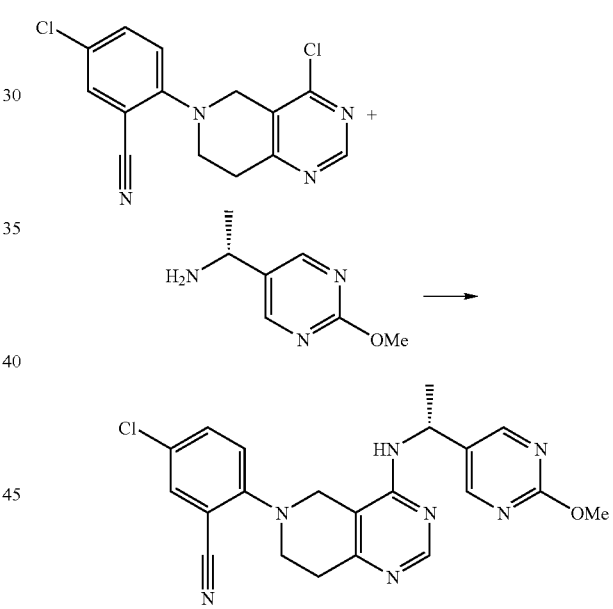

A reaction mixture of 5-chloro-2-(4-chloro-7,8-dihydro-pyrido[4,3-d]pyrimidin-6(5H)-yl)benzonitrile (130 mg, 0.41 mmol) and (R)-1-(2-methoxypyrimidin-5-yl)ethanamine (85 mg, 0.55 mmol) (prepared similarly according to the method for Intermediate 16) in acetonitrile (3 mL) and N,N-diisopropylethylamine (140 μL, 0.83 mmol) was subjected to microwave irradiation at 180° C. for 3 h. The reaction mixture was concentrated and the residue was purified by semi-preparative HPLC (100×20.2 mm, C18 column; 30-60% acetonitrile-water [10 mM Et$_2$NH]) to yield a white solid.

LC-MS: 422.4 [M+H]$^+$ $^1$H NMR (400 MHz, d6-DMSO): δ 8.62 (s, 2H), 8.29 (s, 1H), 7.94 (d, 1H, J=2.8 Hz), 7.77 (dd, 1H, J=8.8, 2.8 Hz), 7.37 (d, 1H, J=8.8 Hz), 7.10 (d, 1H, J=7.2 Hz), 5.39 (p, 1H, J=7.2

Hz), 4.12 and 4.02 (AB, 2H, J=15.6 Hz), 3.88 (s, 3H), 3.56 (m, 2H), 2.85 (t, 2H, J=5.6 Hz), 1.55 (d, 3H, J=7.2 Hz).

Method Y (Compound 58)

2-{4-[(R)-1-(2-Methoxy-pyrimidin-5-yl)-ethylamino]-7,8-dihydro-5H-pyrido[4,3-d]pyrimidin-6-yl}-5-methyl-benzonitrile

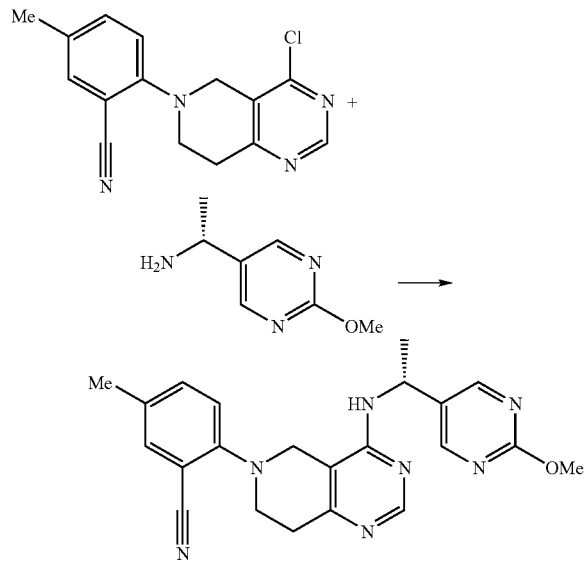

A reaction mixture of 2-(4-chloro-7,8-dihydropyrido[4,3-d]pyrimidin-6(5H)-yl)-5-methylbenzonitrile (430 mg, 1.51 mmol) and (R)-1-(2-methoxypyrimidin-5-yl)ethanamine (238 mg, 1.56 mmol) (prepared similarly according to the method for Intermediate 16) in acetonitrile (6 mL) and N,N-diisopropylethylamine (2 mL, 9 mmol) was subjected to microwave irradiation at 185° C. for 3.5 h. The reaction mixture was concentrated and the residue was purified by semi-preparative HPLC (100×20.2 mm, C18 column; 30-60% acetonitrile-water [10 mM $Et_2NH$]) to yield a light yellow solid.

LC-MS: 402.0 [M+H]$^+$ $^1$H NMR (400 MHz, d6-DMSO): δ 8.62 (s, 2H), 8.29 (s, 1H), 7.59 (d, 1H, J=1.5 Hz), 7.51 (dd, 1H, J=8.5, 1.6 Hz), 7.29 (d, 1H, J=8.5 Hz), 7.09 (d, 1H, J=7.5 Hz), 5.39 (p, 1H, J=7.2 Hz), 4.07 and 3.98 (AB, 2H, J=15.5 Hz), 3.88 (s, 3H), 3.55-3.40 (m, 2H), 2.84 (t, 2H, J=5.4 Hz), 2.29 (s, 3H), 1.55 (d, 3H, J=7.1 Hz).

Method Z (Compound 60)

2-{4-[(S)-2-Hydroxy-1-(2-methoxy-pyrimidin-5-yl)-ethylamino]-7,8-dihydro-5H-pyrido[4,3-d]pyrimidin-6-yl}-5-methyl-benzonitrile

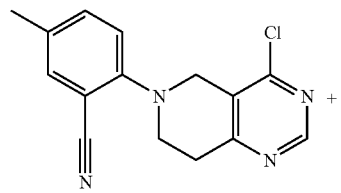

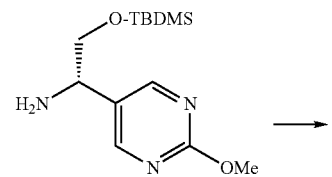

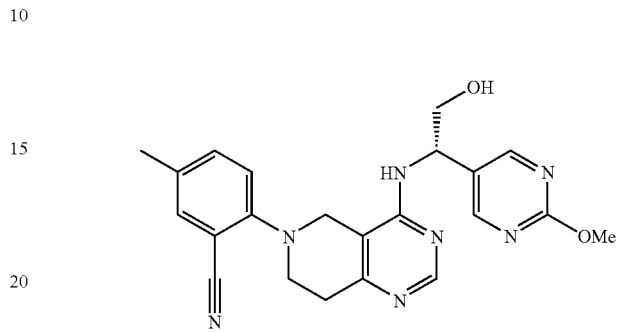

A) (S)-2-(4-(2-(tert-butyldimethylsilyloxy)-1-(2-methoxypyrimidin-5-yl)ethylamino)-7,8-dihydropyrido[4,3-d]pyrimidin-6(5H)-yl)-5-methylbenzonitrile A reaction mixture of 2-(4-chloro-7,8-dihydropyrido[4,3-d]pyrimidin-6(5H)-yl)-5-methylbenzonitrile (500 mg, 1.76 mmol) and (S)-2-(tert-butyldimethylsilyloxy)-1-(2-methoxypyrimidin-5-yl)ethanamine (800 mg, 2.82 mmol) in acetonitrile (10 mL) and N,N-diisopropylethylamine (1 mL) was subjected to microwave irradiation at 185° C. for 3 h. The reaction mixture was concentrated and the residue was purified by silica-gel column to afford a light yellow solid.

LC-MS: 532.5 [M+H]+

B) 2-{4-[(S)-2-hydroxy-1-(2-methoxy-pyrimidin-5-yl)-ethylamino]-7,8-dihydro-5H-pyrido[4,3-d]pyrimidin-6-yl}-5-methyl-benzonitrile To a solution of (S)-2-(4-(2-(tert-butyldimethylsilyloxy)-1-(methoxypyrimidin5-yl)ethylamino)-7,8-dihydropyrido[4,3-d]pyrimidin-6(5H)-yl)-5-methylbenzonitrile (740 mg, 1.39 mmol) in THF (10 mL) was added 1M TBAF in THF (5 mL). The reaction mixture was stirred at room temperature for 10 minutes, and then treated with water and EtOAc. The organic layer was washed with aq. NaHCO$_3$ and brine, dried (MgSO$_4$), and concentrated. The residue was purified by semi-preparative HPLC to yield a white solid.

LC-MS: 418.4 [M+H]$^+$ $^1$H NMR (400 MHz, d6-DMSO): δ 8.62 (s, 2H), 8.28 (s, 1H), 7.60 (d, 1H, J=1.5 Hz), 7.51 (dd, 1H, J=8.5, 1.7 Hz), 7.31 (d, 1H, J=8.5 Hz), 6.97 (d, 1H, J=7.7 Hz), 5.31 (q, 1H, J=6.7 Hz), 5.08 (t, 1H, J=5.9 Hz), 4.11 and 4.01 (AB, 2H, J=15.5 Hz), 3.88 (s, 3H), 3.85-3.67 (m, 2H), 3.48 (t, 2H, J=5.7 Hz), 2.91-2.78 (m, 2H), 2.30 (s, 3H).

Method AA (Compound 61)

2-{4-[(2-Isopropyl-pyrimidin-5-ylmethyl)-amino]-7,8-dihydro-5H-pyrido[4,3-d]pyrimidin-6-yl}-5-methyl-benzonitrile

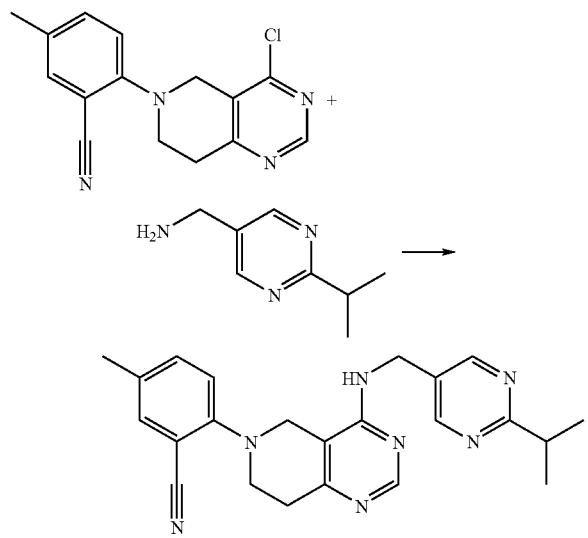

A reaction mixture of 2-(4-chloro-7,8-dihydropyrido[4,3-d]pyrimidin-6(5H)-yl)-5-methylbenzonitrile (80 mg, 0.28 mmol) and (2-isopropylpyrimidin-5-yl)methanamine (60 mg, 0.40 mmol) (prepared similarly according to the method for Intermediate 13) in acetonitrile (1 mL) and N,N-diisopropylethylamine (0.3 mL, 2 mmol) was subjected to microwave irradiation at 185° C. for 3 h. The reaction mixture was concentrated and purified by semi-preparative HPLC (100×20.2 mm, C18 column; 40-60% CH$_3$CN-water [10 mM Et$_2$NH]) to yield a light yellow solid.

LC-MS: 400.4 [M+H]$^+$ $^1$H NMR (400 MHz, d6-DMSO): δ 8.70 (s, 2H), 8.33 (s, 1H), 7.59 (d, 1H, J=1.5 Hz), 7.53-7.45 (m, 2H), 7.23 (d, 1H, J=8.5 Hz), 4.60 (d, 2H, J=5.6 Hz), 4.00 (s, 2H), 3.49 (t, 2H, J=5.6 Hz), 3.18-3.03 (m, 1H), 2.84 (t, 2H, J=5.5 Hz), 2.29 (s, 3H), 1.24 (d, 6H, J=6.8 Hz).

Method AB (Compound 64)

2-{4-[(R)-3-Hydroxy-1-(6-trifluoromethyl-pyridin-3-yl)-propylamino]-7,8-dihydro-5H-pyrido[4,3-d]pyrimidin-6-yl}-5-methyl-benzonitrile

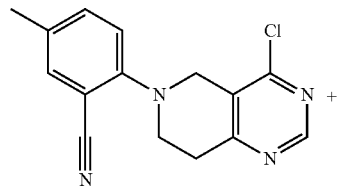

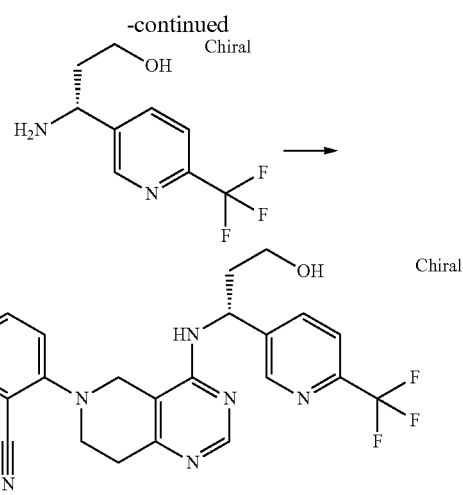

A reaction mixture of 2-(4-chloro-7,8-dihydropyrido[4,3-d]pyrimidin-6(5H)-yl)-5-methylbenzonitrile (200 mg, 0.70 mmol) and (R)-3-amino-3-(6-(trifluoromethyl)pyridin-3-yl)propan-1-ol (180 mg, 0.82 mmol) in acetonitrile (2 mL) and N,N-diisopropylethylamine (0.7 mL, 4 mmol) was subjected to microwave irradiation at 185° C. for 2.5 h. The reaction mixture was concentrated and the residue was purified by semi-preparative HPLC (100×20.2 mm, C18 column; 40-60% acetonitrile-water [10 mM Et$_2$NH]) to yield an off-white solid.

LC-MS: 469.4 [M+H]$^+$ $^1$H NMR (400 MHz, d6-DMSO): δ 8.80 (d, 1H, J=0.9 Hz), 8.23 (s, 1H), 8.05 (dd, 1H, J=8.1, 1.4 Hz), 7.85 (d, 1H, J=8.1 Hz), 7.61 (d, 1H, J=1.4 Hz), 7.53 (dd, 1H, J=8.5, 1.6 Hz), 7.31 (d, 1H, J=8.4 Hz), 7.22 (d, 1H, J=7.5 Hz), 5.52 (q, 1H, J=5.7 Hz), 4.69 (t, 1H, J=4.7 Hz), 4.13 and 4.03 (AB, 2H, J=15.5 Hz), 3.60-3.40 (m, 4H), 2.83 (m, 2H), 2.31 (s, 3H), 2.23-2.08 (m, 1H), 2.03-1.90 (m, 1H).

Method AC (Compound 66)

5-Methyl-2-{4-[(R)-1-(2-methyl-pyrimidin-5-yl)-ethylamino]-7,8-dihydro-5H-pyrido[4,3-d]pyrimidin-6-yl}-benzonitrile

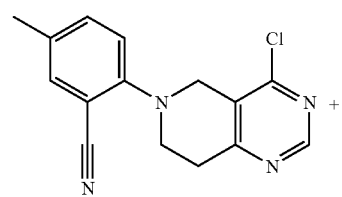

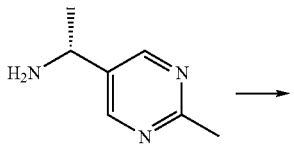

-continued

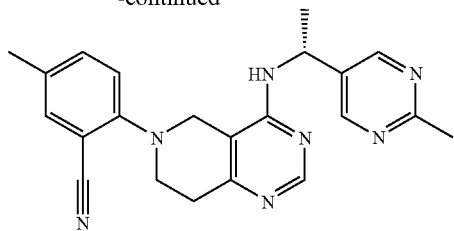

A reaction mixture of 2-(4-chloro-7,8-dihydropyrido[4,3-d]pyrimidin-6(5H)-yl)-5-methylbenzonitrile (350 mg, 1.23 mmol) and (R)-1-(2-methylpyrimidin-5-yl)ethanamine (300 mg, 2.19 mmol) in acetonitrile (3 mL) and N,N-diisopropylethylamine (0.86 mL, 4.9 mmol) was subjected to microwave irradiation at 185° C. for 3.5 h. The reaction mixture was concentrated and the residue was purified by semi-preparative HPLC (100×20.2 mm, C18 column; 30-55% acetonitrile-water [10 mM Et$_2$NH]) to yield an off-white solid.

LC-MS: 386.1 [M+H]$^+$ $^1$H NMR (400 MHz, d6-DMSO): δ 8.70 (s, 2H), 8.27 (s, 1H), 7.59 (d, 1H, J=1.5 Hz), 7.51 (dd, 1H, J=8.5, 1.7 Hz), 7.30 (d, 1H, J=8.4 Hz), 7.13 (d, 1H, J=7.4 Hz), 5.39 (m, 1H), 4.09 and 3.99 (AB, 2H, J=15.5 Hz), 3.55-3.20 (m, 2H), 2.84 (t, 2H, J=5.3 Hz), 2.57 (s, 3H), 2.30 (s, 3H), 1.56 (d, 3H, J=7.1 Hz).

Method AD (Compound 67)

5-Methyl-2-{4-[(S)-1-(2-methyl-pyrimidin-5-yl)-ethylamino]-7,8-dihydro-5H-pyrido[4,3-d]pyrimidin-6-yl}-benzonitrile

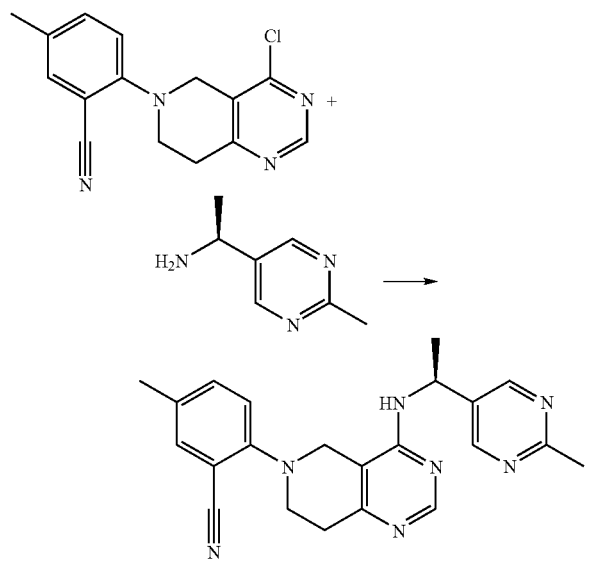

A reaction mixture of 2-(4-chloro-7,8-dihydropyrido[4,3-d]pyrimidin-6(5H)-yl)-5-methylbenzonitrile (60 mg, 0.21 mmol) and (S)-1-(2-methylpyrimidin-5-yl)ethanamine (29 mg, 0.21 mmol) in acetonitrile (2 mL) and N,N-diisopropylethylamine (74 µL, 0.42 mmol) was subjected to microwave irradiation at 180° C. for 1 h. The reaction mixture was concentrated and the residue was purified by semi-preparative HPLC (100×20.2 mm, C18 column; 30-60% acetonitrile-water [10 mM Et$_2$NH]) to yield an off-white solid.

LC-MS: 385.9 [M+H]$^+$ $^1$H NMR (400 MHz, d6-DMSO): δ 8.70 (s, 2H), 8.26 (s, 1H), 7.59 (d, 1H, J=1.6 Hz), 7.51 (dd, 1H, J=8.4, 1.6 Hz), 7.29 (d, 1H, J=8.4 Hz), 7.13 (d, 1H, J=7.2 Hz), 5.39 (p, 1H, J=7.2 Hz), 4.09 and 3.99 (AB, 2H, J=15.6 Hz), 3.48 (m, 2H), 2.84 (t, 2H, J=5.2 Hz), 2.57 (s, 3H), 2.30 (s, 3H), 1.55 (d, 3H, J=7.2 Hz).

Method AE (Compound 73)

5-Chloro-2-{4-[(S)-2-hydroxy-1-(2-methyl-pyrimidin-5-yl)-ethylamino]-7,8-dihydro-5H-pyrido[4,3-d]pyrimidin-6-yl}-benzonitrile

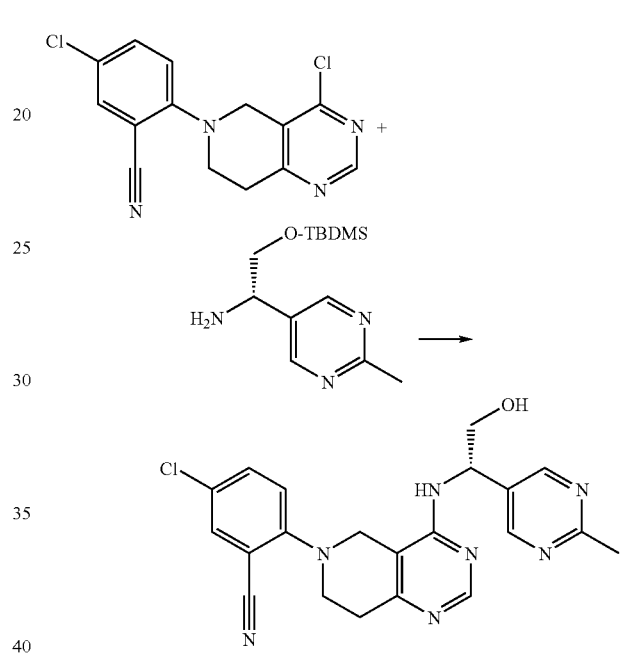

A) (S)-2-(4-(2-(tert-Butyldimethylsilyloxy)-1-(2-methylpyrimidin-5-yl)ethylamino)-7,8-dihydropyrido[4,3-d]pyrimidin-6(5H)-yl)-5-chlorobenzonitrile A reaction mixture of 5-chloro-2-(4-chloro-7,8-dihydropyrido[4,3-d]pyrimidin-6(5H)-yl)benzonitrile (150 mg, 0.49 mmol) and (S)-2-(tert-butyldimethylsilyloxy)-1-(2-methylpyrimidin-5-yl)ethanamine (144 mg, 0.54 mmol) in acetonitrile (2 mL) and N,N-diisopropylethylamine (0.5 mL, 3 mmol) was subjected to microwave irradiation at 185° C. for 3.5 h. The reaction mixture was concentrated and the residue was purified by semi-preparative HPLC to yield the product as a yellow solid.

LC-MS: 536.7 [M+H]+

B) 5-Chloro-2-{4-[(S)-2-hydroxy-1-(2-methyl-pyrimidin-5-yl)-ethylamino]-7,8-dihydro-5H-pyrido[4,3-d]pyrimidin-6-yl}-benzonitrile To a solution of (S)-2-(4-(2-(tert-butyldimethylsilyloxy)-1-(2-methylpyrimidin-5-yl)ethylamino)-7,8-dihydropyrido[4,3-d]pyrimidin-6(5H)-yl)-5-chlorobenzonitrile (60 mg, 0.11 mmol) in THF (10 mL) was added 1M TBAF in THF (5 mL). The reaction mixture was stirred at room temperature for 10 minutes, and then treated with water and EtOAc. The organic layer was washed with aq. NaHCO₃ and brine, dried (MgSO₄), and concentrated. The residue was washed by ethyl ether and water (to completely remove TBAF) and dried to yield the final product as a light colored solid.

LC-MS: 422.5 [M+H]⁺

$^1$H NMR (400 MHz, d6-DMSO): δ 8.70 (s, 2H), 8.27 (s, 1H), 7.94 (d, 1H, J=2.6 Hz), 7.77 (dd, 1H, J=8.9, 2.6 Hz), 7.41 (d, 1H, J=9.0 Hz), 7.04 (d, 1H, J=8.0 Hz), 5.32 (q, 1H, J=6.8 Hz), 5.12 (t, 1H, J=5.9 Hz), 4.18 and 4.08 (AB, 2H, J=15.5 Hz), 3.88-3.68 (m, 2H), 3.57 (t, 2H, J=5.6 Hz), 2.86 (t, 2H, J=5.6 Hz), 2.57 (s, 3H).

Method AF (Compound 74)

2-{4-[(S)-2-Hydroxy-1-(2-methyl-pyrimidin-5-yl)-ethylamino]-7,8-dihydro-5H-pyrido[4,3-d]pyrimidin-6-yl}-5-methyl-benzonitrile

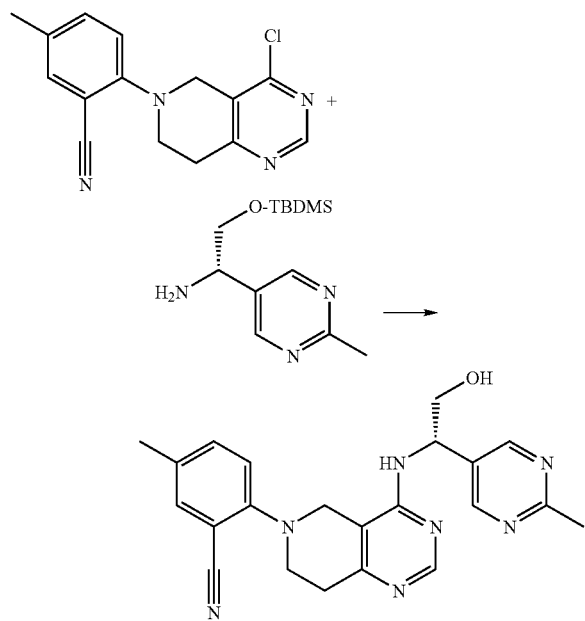

A) (S)-2-(4-(2-(tert-Butyldimethylsilyloxy)-1-(2-methylpyrimidin-5-yl)ethylamino)-7,8-dihydropyrido[4,3-d]pyrimidin-6(5H)-yl)-5-methylbenzonitrile A reaction mixture of 2-(4-chloro-7,8-dihydropyrido[4,3-d]pyrimidin-6(5H)-yl)-5-methylbenzonitrile (420 mg, 1.48 mmol) and (S)-2-(tert-butyldimethylsilyloxy)-1-(2-methylpyrimidin-5-yl)ethanamine (742 mg, 2.78 mmol) in acetonitrile (8 mL) and N,N-diisopropylethylamine (1 mL) was subjected to microwave irradiation at 185° C. for 3 h. The reaction mixture was concentrated and the residue was purified by silica-gel column to yield the product as a light yellow solid.

LC-MS: 516.5 [M+H]⁺

B) 2-{4-[(S)-2-Hydroxy-1-(2-methyl-pyrimidin-5-yl)-ethylamino]-7,8-dihydro-5H-pyrido[4,3-d]pyrimidin-6-yl}-5-methyl-benzonitrile To a solution of (S)-2-(4-(2-(tert-butyldimethylsilyloxy)-1-(2-methylpyrimidin-5-yl)ethylamino)-7,8-dihydropyrido [4,3-d]pyrimidin-6(5H)-yl)-5-methylbenzonitrile (630 mg, 1.22 mmol) in THF (10 mL) was added 1M TBAF in THF (5 mL). The reaction mixture was stirred at room temperature for 10 minutes, and then treated with water and EtOAc. The organic layer was washed with aq. NaHCO₃ and brine, dried (MgSO₄), and concentrated. The residue was washed by ethyl ether to yield a light colored solid.

LC-MS: 402.3 [M+H]⁺

$^1$H NMR (400 MHz, d6-DMSO): δ 8.70 (s, 2H), 8.27 (s, 1H), 7.60 (d, 1H, J=1.4 Hz), 7.51 (dd, 1H, J=8.5, 1.7 Hz), 7.32 (d, 1H, J=8.4 Hz), 7.02 (d, 1H, J=7.6 Hz), 5.32 (q, 1H, J=6.8 Hz), 5.11 (t, 1H, J=5.9 Hz), 4.13 and 4.02 (AB, 2H, J=15.5 Hz), 3.88-3.68 (m, 2H), 3.48 (t, 2H, J=5.6 Hz), 2.92-2.75 (m, 2H), 2.57 (s, 3H), 2.30 (s, 3H).

Method AG (Compound 79)

5-Methyl-2-(4-(quinoxalin-6-ylmethylamino)-7,8-dihydropyrido[4,3-d]pyrimidin-6(5H)-yl)benzonitrile

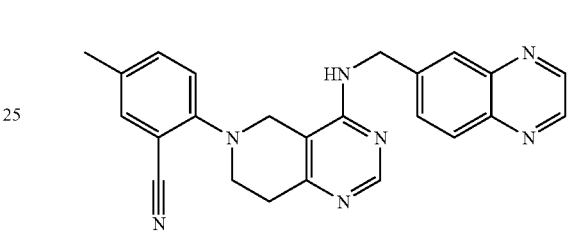

A reaction mixture of 2-(4-chloro-7,8-dihydropyrido[4,3-d]pyrimidin-6(5H)-yl)-5-methylbenzonitrile (100 mg, 0.35 mmol) and quinoxalin-6-ylmethanamine (150 mg, 0.94 mmol) in acetonitrile (1 mL) and N,N-diisopropylethylamine (500 μL, 3 mmol) was subjected to microwave irradiation at 185° C. for 3.5 h. The reaction mixture was concentrated and the residue was purified by preparative HPLC (30-60% acetonitrile-water [10 mM DEA]) to afford a light yellow solid.

LC-MS: 408.2 [M+H]⁺

$^1$H NMR (400 MHz, d6-DMSO): δ 8.91 and 8.90 (AB, 2H, J=1.8 Hz), 8.29 (s, 1H), 8.06 (d, 1H, J=8.6 Hz), 7.97 (d, 1H, J=1.2 Hz), 7.85 (dd, 1H, J=8.6, 1.9 Hz), 7.71 (t, 1H, J=5.8 Hz), 7.60 (d, 1H, J=1.6 Hz), 7.50 (dd, 1H, J=8.6, 1.8 Hz), 7.26 (d, 1H, J=8.5 Hz), 4.91 (d, 2H, J=5.8 Hz), 4.08 (s, 2H), 3.53 (t, 2H, J=5.6 Hz), 2.87 (t, 2H, J=5.5 Hz), 2.29 (s, 3H).

Method AH (Compound 80)

5-Methyl-2-(4-(quinolin-2-ylmethylamino)-7,8-dihydropyrido[4,3-d]pyrimidin-6(5H)-yl)benzonitrile

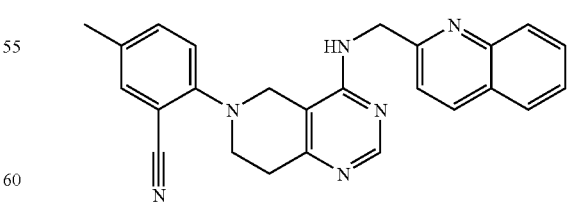

A reaction mixture of 2-(4-chloro-7,8-dihydropyrido[4,3-d]pyrimidin-6(5H)-yl)-5-methylbenzonitrile (150 mg, 0.52 mmol) and quinolin-2-ylmethanamine hydrochloride (206.0 mg, 1.058 mmol) in acetonitrile (1 mL) and N,N-diisopropylethylamine (1 mL, 6 mmol) was subjected to microwave irradiation at 185° C. for 3.5 h. The reaction mixture was concentrated and the residue was purified by preparative HPLC (30-60% acetonitrile-water [10 mM DEA]) to afford a light yellow solid.

LC-MS: 407.3 [M+H]+

$^1$H NMR (400 MHz, CDCl$_3$): δ 8.55 (s, 1H), 8.16 (d, 1H, J=8.4 Hz), 8.08 (d, 1H, J=8.5 Hz), 7.84 (d, 1H, J=8.1 Hz), 7.74 (t, 1H, J=8.0 Hz), 7.56 (t, 1H, J=7.9 Hz), 7.44 (s, 1H), 7.41 (d, 1H, J=8.4 Hz), 7.35 (dd, 1H, J=8.4, 0.94 Hz), 7.05 (d, 1H, J=8.4 Hz), 6.72-6.65 (m, 1H), 4.97 (d, 2H, J=4.0 Hz), 4.24 (s, 2H), 3.65 (t, 2H, J=5.6 Hz), 3.03 (t, 2H, J=5.5 Hz), 2.34 (s, 3H).

Method AI (Compound 81)

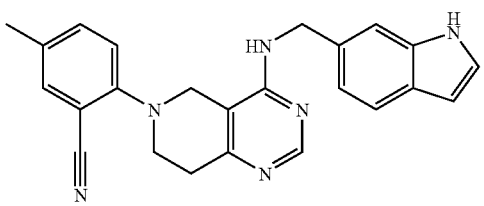

2-(4-((1H-Indol-6-yl)methylamino)-7,8-dihydropyrido[4,3-d]pyrimidin-6(5H)-yl)-5-methylbenzonitrile A reaction mixture of 2-(4-chloro-7,8-dihydropyrido[4,3-d]pyrimidin-6(5H)-yl)-5-methylbenzonitrile (100 mg, 0.35 mmol) and 1-(1H-indol-5-yl)-methylamine (139 mg, 0.95 mmol) in acetonitrile (1 mL) and N,N-diisopropylethylamine (0.4 mL, 2 mmol) was subjected to microwave irradiation at 185° C. for 3 h. The reaction mixture was concentrated and the residue was purified by preparative HPLC (30-60% acetonitrile-water [10 mM DEA]) to afford a light yellow solid.

LC-MS: 395.3 [M+H]+

$^1$H NMR (400 MHz, CDCl$_3$): δ 8.56 (s, 1H), 8.48 (bs, 1H), 7.61 (d, 1H, J=8.1 Hz), 8.39 (s, 1H), 8.38 (s, 1H), 7.28 (dd, 1H, J=8.4, 1.6 Hz), 7.21 (t, 1H, J=2.8 Hz), 7.10 (dd, 1H, J=8.1, 1.4 Hz), 6.97 (d, 1H, J=8.4 Hz), 6.57-6.50 (m, 1H), 4.82 (d, 2H, J=5.2 Hz), 4.69 (t, 1H, J=5.1 Hz), 3.96 (s, 2H), 3.53 (t, 2H, J=5.7 Hz), 3.04 (t, 2H, J=5.6 Hz), 2.29 (s, 3H).

Method AJ (Compound 82)

2-(4-(Benzo[d][1,3]dioxol-5-ylmethylamino)-7,8-dihydropyrido[4,3-d]pyrimidin-6(5H)-yl)-5-methyl-benzonitrile

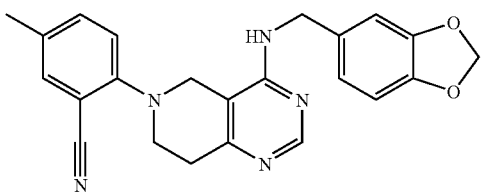

A reaction mixture of 2-(4-chloro-7,8-dihydropyrido[4,3-d]pyrimidin-6(5H)-yl)-5-methylbenzonitrile (100 mg, 0.35 mmol) and piperonylamine (120 mg, 0.79 mmol) in acetonitrile (1 mL) and N,N-diisopropylethylamine (400 μL) was subjected to microwave irradiation at 185° C. for 3 h. The reaction mixture was concentrated and the residue was purified by preparative HPLC (100×20.2 mm, C18 column; 30-60% acetonitrile-water [10 mM Et$_2$NH]) to afford a light yellow solid.

LC-MS: 400.2 [M+H]+

$^1$H NMR (400 MHz, d6-DMSO): δ 8.30 (s, 1H), 7.58 (d, 1H, J=1.5 Hz), 7.49 (dd, 1H, J=8.6, 1.6 Hz), 7.40 (t, 1H, J=5.8 Hz), 7.24 (d, 1H, J=8.5 Hz), 6.89 (d, 1H, J=1.3 Hz), 6.88-6.75 (m, 2H), 5.96 (s, 2H), 4.55 (d, 2H, J=5.8 Hz), 3.98 (s, 2H), 3.49 (t, 2H, J=5.6 Hz), 2.84 (t, 2H, J=5.5 Hz), 2.29 (s, 3H).

Method AK (Compounds 89 and 90)

(R)-2-(4-(1-(Benzo[d][1,3]dioxol-5-yl)ethylamino)-7,8-dihydropyrido[4,3-d]pyrimidin-6(5H)-yl)-5-methylbenzonitrile and (S)-2-(4-(1-(benzo[d][1,3]dioxol-5-yl)ethylamino)-7,8-dihydropyrido[4,3-d]pyrimidin-6(5H)-yl)-5-methylbenzonitrile

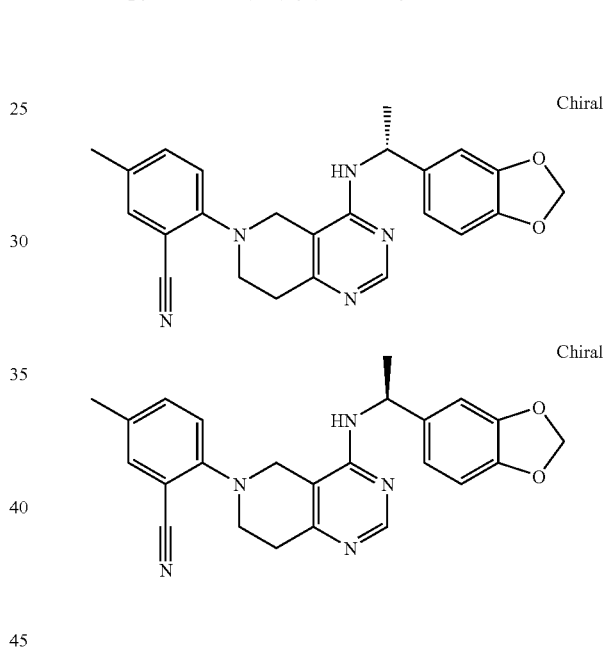

A) 2-(4-(1-(benzo[d][1,3]dioxol-5-yl)ethylamino)-7,8-dihydropyrido[4,3-d]pyrimidin-6(5H)-yl)-5-methylbenzonitrile A reaction mixture of 2-(4-chloro-7,8-dihydropyrido[4,3-d]pyrimidin-6(5H)-yl)-5-methylbenzonitrile (100 mg, 0.35 mmol) and 1-(benzo[d][1,3]dioxol-5-yl)ethanamine (150 mg, 0.91 mmol) in acetonitrile (1 mL) and N,N-diisopropylethylamine (400 μL) was subjected to microwave irradiation at 185° C. for 3 h. The reaction mixture was concentrated and the residue was purified by preparative HPLC (100×20.2 mm, C18 column; 30-60% acetonitrile-water [10 mM Et$_2$NH]) to afford a light yellow solid.

LC-MS: 413.9 [M+H]+;

$^1$H NMR (400 MHz, d6-DMSO): δ 8.25 (s, 1H), 7.59 (d, 1H, J=1.6 Hz), 7.51 (dd, 1H, J=8.6, 1.8 Hz), 7.32 (d, 1H, J=8.4 Hz), 7.00-6.77 (m, 4H), 5.95 (d, 2H, J=6.6 Hz), 5.40-5.30 (m, 1H), 4.05 and 3.98 (AB, 2H, J=15.6 Hz), 3.55-3.45 (m, 2H), 2.83 (t, 2H, J=5.5 Hz), 2.30 (s, 3H), 1.47 (d, 3H, J=7.0 Hz).-

B) (R)-2-(4-(1-(benzo[d][1,3]dioxol-5-yl)ethylamino)-7,8-dihydropyrido[4,3-d]pyrimidin-6(5H)-yl)-5-methylbenzonitrile and (S)-2-(4-(1-(benzo[d][1,3]dioxol-5-yl)ethylamino)-7,8-dihydropyrido[4,3-d]pyrimidin-6(5H)-yl)-5-methylbenzonitrile Racemic 2-(4-(1-(benzo[d][1,3]dioxol-5-yl)ethylamino)-7,8-dihydropyrido[4,3-d]pyrimidin-6(5H)-yl)-5-methylbenzonitrile (70 mg, 0.17 mmol) was resolved by chiral HPLC (CHIRALPAK AD-H column at 0° C. [ice-bath], 20×250 mm, hexane/EtOH/Et$_2$NH [85:15:0.085] at 20 mL/min, UV at 240 nm) to afford the title compounds.

(R)-isomer:

LC-MS: 414.4 [M+H]$^+$;

$^1$H NMR (400 MHz, d6-DMSO): δ 8.25 (s, 1H), 7.59 (d, 1H, J=1.6 Hz), 7.51 (dd, 1H, J=8.6, 1.7 Hz), 7.32 (d, 1H, J=8.5 Hz), 7.00-6.77 (m, 4H), 5.95 (d, 2H, J=6.6 Hz), 5.40-5.30 (m, 1H), 4.05 and 3.98 (AB, 2H, J=15.6 Hz), 3.55-3.45 (m, 2H), 2.83 (t, 2H, J=5.5 Hz), 2.30 (s, 3H), 1.46 (d, 3H, J=7.0 Hz).

(S)-isomer:

LC-MS: 414.4 [M+H]$^+$;

$^1$H NMR (400 MHz, d6-DMSO): 8.25 (s, 1H), 7.59 (d, 1H, J=1.6 Hz), 7.51 (dd, 1H, J=8.6, 1.7 Hz), 7.32 (d, 1H, J=8.4 Hz), 7.00-6.77 (m, 4H), 5.95 (d, 2H, J=6.6 Hz), 5.40-5.30 (m, 1H), 4.05 and 3.98 (AB, 2H, J=15.6 Hz), 3.55-3.45 (m, 2H), 2.83 (t, 2H, J=5.5 Hz), 2.30 (s, 3H), 1.46 (d, 3H, J=7.0 Hz).

Method AL (Compound 91)

5-Methyl-2-(4-(1-(4-methyl-3-(methylsulfonyl)phenyl)ethylamino)-7,8-dihydropyrido[4,3-d]pyrimidin-6(5H)-yl)benzonitrile

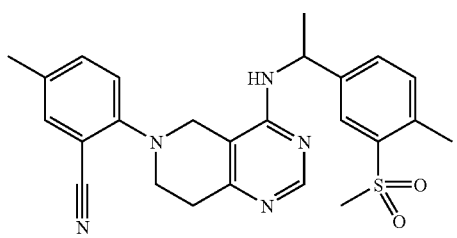

A reaction mixture of 2-(4-chloro-7,8-dihydropyrido[4,3-d]pyrimidin-6(5H)-yl)-5-methylbenzonitrile (360 mg, 1.26 mmol) and 1-(4-methyl-3-(methylsulfonyl)phenyl)ethanamine (400 mg, 1.88 mmol) in acetonitrile (3 mL) and N,N-diisopropylethylamine (1 mL) was subjected to microwave irradiation at 185° C. for 3.5 h. The reaction mixture was concentrated and the residue was purified by preparative HPLC (100×20.2 mm, C18 column; 30-60% acetonitrile-water [10 mM Et$_2$NH]) to afford a light yellow solid (290 mg).

LC-MS: 462.3 [M+H]$^+$ $^1$H NMR (400 MHz, d6-DMSO): δ 8.25 (s, 1H), 7.94 (d, 1H, J=1.8 Hz), 7.65-7.55 (m, 2H), 7.51 (dd, 1H, J=8.7, 1.8 Hz), 7.39 (d, 1H, J=8.0 Hz), 7.31 (d, 1H, J=8.4 Hz), 7.18 (d, 1H, J=7.6 Hz), 5.52-5.42 (m, 1H), 4.06 and 4.01 (AB, 2H, J=15.5 Hz), 3.57-3.42 (m, 2H), 3.19 (s, 3H), 2.83 (t, 2H, J=5.4 Hz), 2.59 (s, 3H), 2.30 (s, 3H), 1.52 (d, 3H, J=7.0 Hz).

Method AM (Compound 92)

5-Methyl-2-(4-(quinolin-7-ylmethylamino)-7,8-dihydropyrido[4,3-d]pyrimidin-6(5H)-yl)benzonitrile

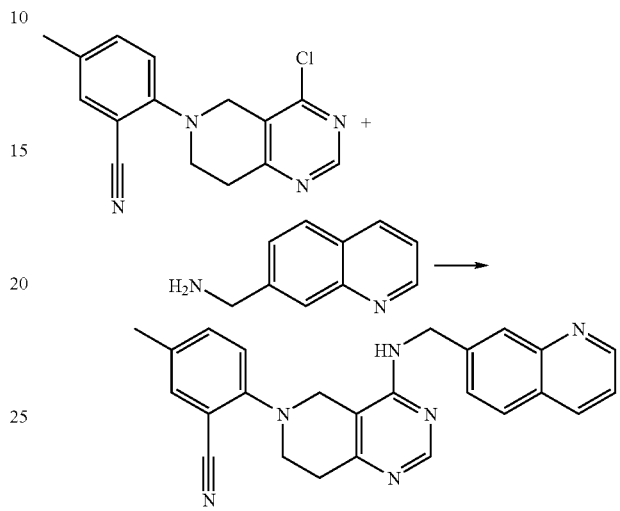

A reaction mixture of 2-(4-chloro-7,8-dihydropyrido[4,3-d]pyrimidin-6(5H)-yl)-5-methylbenzonitrile (480 mg, 1.69 mmol) and quinolin-7-ylmethanamine (400 mg, 2.53 mmol) in acetonitrile (5 mL) and N,N-diisopropylethylamine (1.5 mL, 8.6 mmol) was subjected to microwave irradiation at 185° C. for 3.5 h. The reaction mixture was concentrated and the residue was purified by semi-prep HPLC (100×20.2 mm, C18 column; 30-60% acetonitrile-water [10 mM diethylamine]) to yield an off white solid.

LC-MS: 407.3 [M+H]$^+$ $^1$H NMR (400 MHz, d6-DMSO): δ 8.85 (dd, 1H, J=4.0, 1.6 Hz), 8.33 (d, 1H, J=8.0 Hz), 8.29 (s, 1H), 7.93 (d, 1H, J=8.4 Hz), 7.89 (s, 1H), 7.65 (t, 1H, J=5.6 Hz), 7.63-7.56 (m, 2H), 7.52-7.45 (m, 2H), 7.26 (d, 1H, J=8.4 Hz), 4.87 (d, 2H, J=5.6 Hz), 4.07 (s, 2H), 3.53 (t, 2H, J=5.6 Hz), 2.86 (t, 2H, J=5.6 Hz), 2.29 (s, 3H).

Method AN (Compounds 93 and 94)

(R)-2-(4-(1-(4-Chloro-3-(methylsulfonyl)phenyl)ethylamino)-7,8-dihydropyrido[4,3-d]pyrimidin-6(5H)-yl)-5-methylbenzonitrile and (S)-2-(4-(1-(4-chloro-3-(methylsulfonyl)phenyl)ethylamino)-7,8-dihydropyrido[4,3-d]pyrimidin-6(5H)-yl)-5-methylbenzonitrile

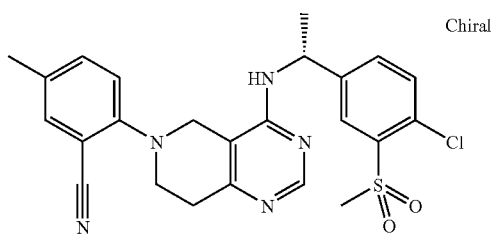

-continued

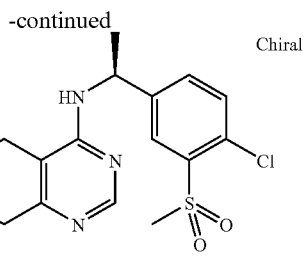

A) 2-(4-(1-(4-chloro-3-(methylsulfonyl)phenyl)ethylamino)-7,8-dihydropyrido[4,3-d]pyrimidin-6(5H)-yl)-5-methylbenzonitrile A reaction mixture of 2-(4-chloro-7,8-dihydropyrido[4,3-d]pyrimidin-6(5H)-yl)-5-methylbenzonitrile (250 mg, 0.88 mmol) and 1-(4-chloro-3-(methylsulfonyl)phenyl)ethanamine (300 mg, 1.28 mmol) in acetonitrile (2 mL) and N,N-diisopropylethylamine (700 μL) was subjected to microwave irradiation at 185° C. for 3.5 h. The reaction mixture was concentrated and the residue was purified by preparative HPLC (100×20.2 mm, C18 column; 30-60% acetonitrile-water [10 mM Et$_2$NH]) to afford a light yellow solid.

LC-MS: 482.2 [M+H]$^+$ $^1$H NMR (400 MHz, d6-DMSO): δ 8.25 (s, 1H), 8.08 (d, 1H, J=2.1 Hz), 7.75 (dd, 1H, J=8.3, 2.1 Hz), 7.67 (d, 1H, J=8.2 Hz), 7.60 (d, 1H, J=1.6 Hz), 7.52 (dd, 1H, J=8.5, 1.8 Hz), 7.30 (d, 1H, J=8.5 Hz), 7.23 (d, 1H, J=7.4 Hz), 5.52-5.42 (m, 1H), 4.07 and 4.03 (AB, 2H, J=15.5 Hz), 3.57-3.42 (m, 2H), 3.36 (s, 3H), 2.83 (t, 2H, J=5.4 Hz), 2.30 (s, 3H), 1.53 (d, 3H, J=7.1 Hz).

B) (R)-2-(4-(1-(4-chloro-3-(methylsulfonyl)phenyl)ethylamino)-7,8-dihydropyrido[4,3-d]pyrimidin-6(5H)-yl)-5-methylbenzonitrile and (S)-2-(4-(1-(4-chloro-3-(methylsulfonyl)phenyl)ethylamino)-7,8-dihydropyrido[4,3-d]pyrimidin-6(5H)-yl)-5-methylbenzonitrile Racemic 2-(4-(1-(4-chloro-3-(methylsulfonyl)phenyl)ethylamino)-7,8-dihydropyrido[4,3-d]pyrimidin-6(5H)-yl)-5-methylbenzonitrile (100 mg, 0.21 mmol) was resolved by chiral HPLC(CHIRALPAK AD-H column at ambient, 20×250 mm, hexane/EtOH/Et$_2$NH [75:25:0.05] at 20 mL/min, UV at 240 nm; 100 mg sample was dissolved in 3 mL EtOH and 3 mL hexane; maximum injection 3 mL) to afford the title compounds.

(R)-isomer:
LC-MS: 482.3 [M+H]$^+$;
$^1$H NMR (400 MHz, d6-DMSO): δ 8.25 (s, 1H), 8.08 (d, 1H, J=2.1 Hz), 7.75 (dd, 1H, J=8.3, 2.1 Hz), 7.67 (d, 1H, J=8.2 Hz), 7.60 (d, 1H, J=1.6 Hz), 7.52 (dd, 1H, J=8.5, 1.8 Hz), 7.30 (d, 1H, J=8.5 Hz), 7.23 (d, 1H, J=7.4 Hz), 5.52-5.42 (m, 1H), 4.07 and 4.03 (AB, 2H, J=15.5 Hz), 3.57-3.42 (m, 2H), 3.36 (s, 3H), 2.83 (t, 2H, J=5.4 Hz), 2.30 (s, 3H), 1.53 (d, 3H, J=7.1 Hz).

(S)-isomer:
LC-MS: 482.3 [M+H]$^+$;
$^1$H NMR (400 MHz, d6-DMSO): δ 8.25 (s, 1H), 8.08 (d, 1H, J=2.1 Hz), 7.75 (dd, 1H, J=8.3, 2.1 Hz), 7.67 (d, 1H, J=8.2 Hz), 7.60 (d, 1H, J=1.6 Hz), 7.52 (dd, 1H, J=8.5, 1.8 Hz), 7.30 (d, 1H, J=8.5 Hz), 7.23 (d, 1H, J=7.4 Hz), 5.52-5.42 (m, 1H), 4.07 and 4.03 (AB, 2H, J=15.5 Hz), 3.57-3.42 (m, 2H), 3.36 (s, 3H), 2.83 (t, 2H, J=5.4 Hz), 2.30 (s, 3H), 1.53 (d, 3H, J=7.1 Hz).

Method AO (Compounds 95 and 96)

(R)-5-Methyl-2-(4-(1-(quinoxalin-6-yl)ethylamino)-7,8-dihydropyrido[4,3-d]pyrimidin-6(5H)-yl)benzonitrile and (S)-5-methyl-2-(4-(1-(quinoxalin-6-yl)ethylamino)-7,8-dihydropyrido[4,3-d]pyrimidin-6(5H)-yl)benzonitrile

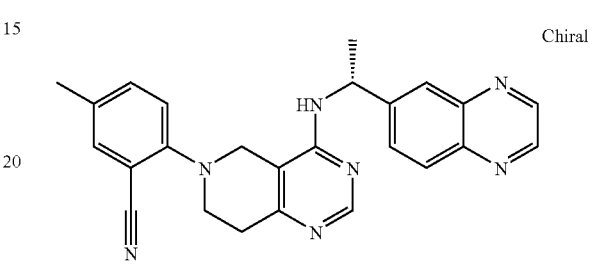

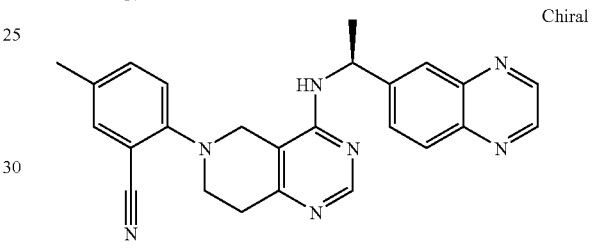

A) 5-methyl-2-(4-(1-(quinoxalin-6-yl)ethylamino)-7,8-dihydropyrido[4,3-d]pyrimidin-6(5H)-yl)benzonitrile A reaction mixture of 2-(4-chloro-7,8-dihydropyrido[4,3-d]pyrimidin-6(5H)-yl)-5-methylbenzonitrile (200 mg, 0.70 mmol) and 1-(quinoxalin-6-yl)ethanamine (150 mg, 0.87 mmol) in acetonitrile (2 mL) and N,N-diisopropylethylamine (734 μL, 4.2 mmol) was subjected to microwave irradiation at 185° C. for 3.5 h. The reaction mixture was concentrated and the residue was purified by preparative HPLC (100×20.2 mm, C18 column; 30-60% acetonitrile-water [10 mM Et$_2$NH]) to afford a light brown solid (45 mg).

LC-MS: 421.9 [M+H]$^+$;
$^1$H NMR (400 MHz, d6-DMSO): δ 8.91 and 8.89 (AB, 2H, J=1.8 Hz), 8.23 (s, 1H), 8.06 (d, 1H, J=8.8 Hz), 8.04 (d, 1H, J=1.6 Hz), 7.94 (dd, 1H, J=8.7, 1.9 Hz), 7.61 (d, 1H, J=1.6 Hz), 7.53 (dd, 1H, J=8.6, 1.7 Hz), 7.35 (d, 1H, J=8.5 Hz), 7.30 (d, 1H, J=7.6 Hz), 5.80-5.55 (m, 1H), 4.16 and 4.07 (AB, 2H, J=15.5 Hz), 3.57-3.42 (m, 2H), 2.86 (t, 2H, J=4.8 Hz), 2.31 (s, 3H), 1.64 (d, 3H, J=7.1 Hz).

B) (R)-5-methyl-2-(4-(1-(quinoxalin-6-yl)ethylamino)-7,8-dihydropyrido[4,3-d]pyrimidin-6(5H)-yl)benzonitrile and (S)-5-methyl-2-(4-(1-(quinoxalin-6-yl)ethylamino)-7,8-dihydropyrido[4,3-d]pyrimidin-6(5H)-yl)benzonitrile Racemic 5-methyl-2-(4-(1-(quinoxalin-6-yl)ethylamino)-7,8-dihydropyrido[4,3-d]pyrimidin-6(5H)-yl)benzonitrile (40 mg, 0.095 mmol) was resolved by chiral HPLC (CHIRALPAK AD-H column at ambient, 20×250 mm, hexane/EtOH/MeOH [80:10:10] at 20 mL/min, UV at 254 nm; 40 mg sample was dissolved in 2 mL EtOH and 2 mL hexane; maximum injection 1.8 mL) to afford the title compounds.

(R)-isomer:
LC-MS: 422.5 [M+H]$^+$;
$^1$H NMR (400 MHz, d6-DMSO): δ 8.91 and 8.89 (AB, 2H, J=1.8 Hz), 8.23 (s, 1H), 8.06 (d, 1H, J=8.7 Hz), 8.04 (d, 1H, J=1.7 Hz), 7.93 (dd, 1H, J=8.7, 2.0 Hz), 7.61 (d, 1H, J=1.6 Hz), 7.53 (dd, 1H, J=8.6, 1.7 Hz), 7.34 (d, 1H, J=8.5 Hz), 7.29 (d, 1H, J=7.6 Hz), 5.75-5.55 (m, 1H), 4.16 and 4.07 (AB, 2H, J=15.6 Hz), 3.57-3.42 (m, 2H), 2.86 (t, 2H, J=5.0 Hz), 2.31 (s, 3H), 1.64 (d, 3H, J=7.1 Hz).

(S)-isomer:
LC-MS: 422.5 [M+H]$^+$;
$^1$H NMR (400 MHz, d6-DMSO): δ 8.91 and 8.89 (AB, 2H, J=1.8 Hz), 8.23 (s, 1H), 8.06 (d, 1H, J=8.8 Hz), 8.04 (d, 1H, J=1.5 Hz), 7.94 (dd, 1H, J=8.7, 1.9 Hz), 7.61 (d, 1H, J=1.6 Hz), 7.53 (dd, 1H, J=8.6, 1.7 Hz), 7.34 (d, 1H, J=8.5 Hz), 7.29 (d, 1H, J=7.6 Hz), 5.72-5.55 (m, 1H), 4.16 and 4.07 (AB, 2H, J=15.5 Hz), 3.57-3.42 (m, 2H), 2.86 (t, 2H, J=4.6 Hz), 2.31 (s, 3H), 1.64 (d, 3H, J=7.1 Hz).

Assays

Compounds provided herein can be evaluated using cell-based assays, such as calcium influx or electrophysiological assays, using biochemical assays, such as binding assays to P2X2 and P2X3 receptors, or can be evaluated in animal models of pain or urinary function. Examples of assays are described below.

The purinergic receptors P2X2 and P2X3 are expressed in a variety of tissues including various sensory and sympathetic ganglia, such as the dorsal root (DRG), nodose (ND), trigeminal (TG), and superior cervical ganglia (SCG) and also in smooth muscle cells (Burnstock, *Trends Pharmacol. Sci.* 27:166-76, 2006). In several regions, P2X2 and P2X3 receptors are coexpressed and functional studies have demonstrated the presence of heteromeric P2X2/3 receptors whose properties differ from those of either homomeric receptor. In addition, chimeric P2X2/3 receptors, containing the N-terminal cytoplasmic domain of P2X2 fused to the first transmembrane domain of P2X3 have been described; these chimeric channels retain the pharmacological profile of homomeric P2X3 receptors, while gaining the non-desensitizing phenotype of the homomeric P2X2 receptor (Neelands et al., *Br. J. Pharmacol.* 140:202-10, 2003). The non-desensitizing behavior of the chimeric receptor is especially useful for screening.

Members of the P2X family are ligand-gated non-selective cation channels whose activity can be characterized by using electrophysiological methods, or by measuring calcium ion influx using calcium-sensitive fluorescent dyes. Applications of agonists such as ATP, or an ATP analog such as α,β-Methyleneadenosine 5'-triphosphate (αβMeATP, Sigma-Aldrich), causes channel opening, resulting in current flow and calcium influx (Bianchi et al., *Eur. J. Pharmacol.* 376:127-38, 1999).

The compounds provided herein can be tested for antagonist activity at P2X3 and P2X2/3 receptors by measuring their ability to affect channel opening by ATP, αβMeATP, or other agonists. Functional tests of receptor activity include but are not limited to: (i) calcium ion influx measured by fluorescence of a calcium-sensitive dye and; (ii) ion flux resulting from channel opening measured by electrophysiological methods. These methods can be used to evaluate channel function when the relevant receptor is heterologously expressed in mammalian or amphibian cells. These methods can also be used to evaluate compounds provided herein in rodent primary neurons and other mammalian primary cells and cell lines that normally express the receptor of interest.

Compounds can further be evaluated for their ability to bind P2X3 and P2X2/3 receptors using biochemical approaches.

Compounds can also be evaluated for their ability to modify sensory and autonomic nervous system signaling where the receptors are known to have a role (e.g., urinary bladder afferent signaling, sensory nerve pain sensation). Finally, compounds provided herein can be tested in vivo in relevant animal models known to one skilled in the art, such as, for example, models of neuropathic, inflammatory, or visceral pain, or models of urinary incontinence.

The following biological examples are offered to illustrate the compounds, pharmaceutical compositions and methods provided herein and are not to be construed in any way as limiting the scope thereof.

Calcium Uptake Assay

Clones and Cell Lines:
Human P2X3 (Accession no. NM_002559), P2X2 (Accession no. NM_170682) and Rat P2X3 (Accession no. NM_031075) and P2X2 (Accession no. NM_053656) are cloned into a mammalian expression vector (e.g., pcDNA5/TO or pcDNA3 Invitrogen). The human P2X2/3 chimera clone is created as described by Neelands et al, and then cloned into an expression vector as above. Receptors are expressed in cells (e.g., HEK293 or 1321N1 (obtained from the ECACC)) via transient transfection using standard lipid mediated transfection, or by creation of stable transfectants for each receptor. For expression of the P2X2/3 heteromeric receptor, the P2X3 expression vector is stably transfected into a cell line already stably expressing P2×2. P2X2/3 heteromer function is isolated using pharmacological methods. Cell lines are maintained in DMEM+5% Glutamax, the appropriate level of selective antibiotic, and 10% heat inactivated FBS.

P2X Antagonist Assay:
Functional activity of compounds at the P2X receptor is determined by measuring their ability to inhibit agonist-induced calcium influx. Compounds are tested for antagonist activity against the P2X2/3 chimera, the P2X3 homomer, or the P2X2/3 heteromer. At the start of each screening day, the agonist EC$_{50}$ is determined. Compound % inhibition or IC$_{50}$s are subsequently determined using a pre-determined agonist concentration (EC$_{50-90}$ depending on cell line) as a stimulus. The agonists used are αβMeATP, ATP, or other ATP analogs. Compounds may be tested at concentrations ranging from 1 µM to 10 µM.

To test for antagonist activity, cells expressing the appropriate receptor are seeded onto 96 or 384 well plates 18-24 hours prior to assay. On the day of the assay, cells are loaded with calcium-sensitive fluorescent dye (e.g., Fluo-4 no wash reagent-Invitrogen cat# F36206, or the BD™ PBX Calcium Assay Kit-BD cat# 640175) in Hank's Buffered Salt Solution (HBSS) with up to 10 mM supplemental CaCl$_2$. Plates are incubated at 37° C. and then equilibrated at room temperature. Antagonism of agonist-induced calcium influx is measured using a fluorescent imaging plate reader (e.g. FLIPR$^{TETRA}$, Molecular Devices, Sunnyvale, Calif.). The assay comprises two stages: a pre-treatment phase followed by a treatment phase. Compounds may be tested as follows: For the pre-treatment phase, 50 µL of 3× concentration of test compound in HBSS is added to cells containing 100 µL of dye loading media to achieve a final concentration of 1× test compound. For the treatment phase, at a set interval after pre-treatment (1-30 minutes), 50 µL of 1× test compound plus 4× agonist solution is added, resulting in a final concentration of 1× compound and 1X agonist. Fluorescence is measured at 0.1-3 second intervals—with an excitation wavelength of 494 nM and an emission wavelength of 515 nM. Responses are measured as (peak fluorescence after agonist addition) minus (baseline fluorescence prior to treatment). Percent inhibition is calculated as follows:

$$\text{Percentage inhibition} = 1 - \frac{\left(\begin{array}{c}\text{Compound Response} - \\ \text{Control Resonse}\end{array}\right)}{\left(\begin{array}{c}\text{Agonist Response} - \\ \text{Control Response}\end{array}\right)} \times 100$$

IC$_{50}$ values are determined by analyzing dose response data in a 4 parameter logistic fit using GraphPad Prism.

Electrophysiological Experiments

Whole Cell Patch Clamp:

Whole cell recordings are made using the Multiclamp 700A patch-clamp amplifier and Clampex acquisition program (Molecular Devices Corporation). Whole-cell recordings are obtained from 1321N1 or HEK cells stably or transiently transfected with P2X3 and/or P2X2 expression vectors. Solutions are either applied for periods of 1 to 3s by a gravity flow, 8-valve delivery system, or for periods of milliseconds using the quick-change Dynaflow perfusion system (Cellectricon Inc.). The internal pipette solution may include 140 mM Cesium-Chloride, 10 mM EGTA, and 5 mM Hepes at pH 7.2; normal external solution is 140 mM NaCl, 5 mM KCl, 1 mM CaCl$_2$, 2 mM MgCl$_2$, 25 mM Hepes, and 10 mM glucose. Concentration-response curves are obtained by recording currents in response to brief applications of agonist at 1-3 min intervals where regular external solution is perfused during the intervals. To obtain inhibition curves, antagonists are pre-applied to the cells for a defined time period before a short application of the agonist+antagonist. The periods of antagonist pre-application and agonist+antagonist applications are constant for the entire test concentration series. Agonist evoked currents are measured in cells that are voltage clamped at −60 or −80 millivolts. IC$_{50}$ values are determined by analyzing dose response data in a 4 parameter logistic fit using GraphPad Prism or Origin.

Automated Two-Electrode Voltage Clamp Recording:

*Xenopus* oocytes (Nasco) are isolated by enzymatic dissociation using collagenase (Worthington, 2 mg/ml). Oocytes are then individually injected with P2×3, P2×2, or a combination of P2X2 and P2X3 mRNA. Each oocyte receives ~64 mL of RNA solution in water at a concentration of ~0.01 µg/µL. Injected oocytes are stored in standard oocyte incubation solution, ND96, containing (in mM) 96 NaCl, 2 KCl, 1 MgCl$_2$, 1-5 CaCl$_2$ and 50 µg/mL Gentamicin at 16° C. Agonist-induced-current caused by P2X channel opening is observed in oocytes 1-5 days after injection. For automated recordings, 8 oocytes are placed in the recording chambers. Each oocyte is impaled by 2 glass electrodes having resistances of 0.5 to 1 MOhm when filled with a 3 M KCl solution. Electrode advancement and oocyte implement are under software control (OPUSXPRESS 1.1, Molecular devices Corporation). The solutions are prepared in 96 well plates and robotically pipetted into the oocyte recording chambers by an 8 channel pipettor. Inhibition by antagonists is determined by calculating % current remaining when oocytes are stimulated with agonist in the presence of test compound compared to the peak current in the presence of agonist alone. The sequence of solution application to the oocyte is as follows: a specific concentration (e.g., EC$_{50}$, EC$_{80}$, or EC$_{90}$) of the agonist is added first to elicit the maximal response. After the pulse, oocytes are washed for several minutes with ND96. The test compound is then added at a particular concentration, followed by the compound at the same concentration along with the agonist. Concentrations for the compounds may range from 0.3 to 10,000 nM. IC$_{50}$ values are determined by analyzing dose response data using a 4 parameter logistic fit using GraphPad Prism or Origin software.

Manual Two-Electrode Voltage Clamp:

Individual oocytes are impaled manually with 2 electrodes and agonist evoked current are measured using an Oocyte clamp amplifier (Warner Instrument Corp.) and Clampex (Molecular Devices Corporation) acquisition software. Solutions are delivered using gravity flow and applied as above. The agonist induced current is measured in the absence and presence of antagonist. Antagonists are tested in a concentration series to obtain an inhibition curve as described above.

Selectivity Screens:

Compounds that inhibit P2X3 and/or P2X2/3 activation will be tested for activity against other P2X receptors to determine their selectivity for specific P2X family members. The list of receptors to be assayed includes, but is not restricted to P2X1, P2×2, P2×4, P2×5, P2×6, and P2×7. The types of assay used for selectivity determination may include: 1) Agonist-induced Calcium influx in cells heterologously expressing the relevant receptor, 2) Electrophysiological determination of receptor inhibition in either mammalian cells or *Xenopus* oocytes heterologously expressing the receptor of interest. Methods and data analysis are similar to those described above for P2X3 and P2X2/3.

Radioligand Binding:

Radioligand experiments are done to determine the affinity of test compounds for P2X3 homomeric and P2X2/3 heteromeric receptors. These studies also provide valuable insights into the mechanism of action of antagonism. The general methodologies used for radioligand binding experiments for P2X3 and P2X2/3 receptors are described by Jarvis et al., *J. Pharmacol. Exp. Ther.* 10:407-16, 2004.

Briefly, cell membranes are prepared from cells transiently or stably expressing P2X3 or P2X2/3 receptors. Cells are grown to confluence, washed, isolated, and stored as pellets at −80° C. until use. Some studies may require the addition of Apyrase or hexokinase (Sigma-Aldrich) during membrane preparation to minimize ATP-mediated receptor desensitization during membrane preparation. Membranes are prepared by resuspending the cell pellet in homogenization buffer, homogenizing, and centrifuging to obtain a membrane pellet. Total protein concentrations are determined using standard methods.

Displacement binding studies are conducted using procedures adapted from Jarvis et al. Under optimized conditions, ligand competition experiments are conducted using radioligand ([$^3$H]A-317491, Abbott), or other high affinity radioligands and a range of different concentrations of test compounds in binding buffer. Ligand saturation studies are conducted using a range of concentrations of radioligand. All binding reactions are terminated by rapid filtration through a glass fiber filter. Membranes are washed, incubated in scintillant, and counted in a scintillation counter. IC$_{50}$ values are determined using a four-parameter logistic Hill equation.

Drug Metabolism and Pharmacokinetics

Caco-2 Permeability:

Caco-2 permeability is measured according to the method described in Yee, *Pharm. Res.* 14:763-6, 1997. Caco-2 cells are grown on filter supports (Falcon HTS multiwell insert system) for 14 days. Culture medium is removed from both the apical and basolateral compartments and the monolayers are preincubated with pre-warmed 0.3 mL apical buffer and 1.0 mL basolateral buffer for 0.75 hour at 37° C. in a shaker water bath at 50 cycles/min. The apical buffer consists of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consists of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media is removed and test compound solution (10 μM) in buffer is added to the apical compartment. The inserts are moved to wells containing fresh basolateral buffer and incubated for 1 hr. Drug concentration in the buffer is measured by LC/MS analysis.

Flux rate (F, mass/time) is calculated from the slope of cumulative appearance of substrate on the receiver side and apparent permeability coefficient (Papp) is calculated from the following equation:

$$Papp(cm/sec)=(F*VD)/(SA*MD)$$

where SA is surface area for transport (0.3 $cm^2$), VD is the donor volume (0.3 mL), MD is the total amount of drug on the donor side at t=0. All data represent the mean of 2 inserts. Monolayer integrity is determined by Lucifer Yellow transport.

Human Dofetilide Binding:

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells are homogenized using a Polytron homogenizer (at the maximum power for 20 seconds) and centrifuged at 48,000 g for 20 minutes at 4° C. The pellet is resuspended, homogenized and centrifuged once more in the same manner. The resultant supernatant is discarded and the final pellet was resuspended (10-fold volume of 50 mM Tris buffer) and homogenized at the maximum power for 20 seconds. The membrane homogenate is aliquoted and stored at −80° C. until use. An aliquot is used for protein concentration determination using a Protein Assay Rapid Kit and ARVO SX plate reader (Wallac). All the manipulation, stock solution and equipment are kept on ice at all time. For saturation assays, experiments are conducted in a total volume of 200 μL. Saturation is determined by incubating 20 μL of [$^3$H]-dofetilide and 160 μl of membrane homogenates (20-30 μg protein per well) for 60 min at room temperature in the absence or presence of 10 μM dofetilide at final concentrations (20 μL) for total or nonspecific binding, respectively. All incubations are terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity is quantified by liquid scintillation counting using Packard LS counter.

For the competition assay, compounds are diluted in 96 well polypropylene plates as 4-point dilutions in semi-log format. All dilutions are performed in DMSO first and then transferred into 50 mM Tris buffer (pH 7.5 at 25° C.) containing 1 mM $MgCl_2$, 10 mM KCl so that the final DMSO concentration became equal to 1%. Compounds are dispensed in triplicate in assay plates (4 μL). Total binding and nonspecific binding wells are set up in 6 wells as vehicle and 10 μM dofetilide at final concentration, respectively. The radioligand is prepared at 5.6× final concentration and this solution is added to each well (36 μL). The assay is initiated by addition of YSi poly-L-lysine Scintillation Proximity Assay (SPA) beads (50 μL, 1 mg/well) and membranes (110 μL, 20 μg/well). Incubation is continued for 60 min at room temperature. Plates are incubated for a further 3 hours at room temperature for beads to settle. Receptor-bound radioactivity is quantified by counting WALLAC MICROBETA plate counter.

HERG Assay:

HEK 293 cells which stably express the HERG potassium channel are used for electrophysiological study. The methodology for stable transfection of this channel in HEK cells can be found elsewhere (Zhou et al., *Biophys. J.* 74:230-41, 1998). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MOhm and seal resistances >1 GOhm are accepted for further experimentation. Series resistance compensation was applied up to a maximum of 80%. No leak subtraction is done. However, acceptable access resistance depends on the size of the recorded currents and the level of series resistance compensation that can safely be used. Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This was followed by a descending voltage ramp (rate 0.5 mV msec-1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristaltic pump. Provided there are minimal changes in the amplitude of the evoked current response in the vehicle control condition, the test compound of either 0.3, 1, 3, 10 mM is applied for a 10 min period. The 10 min period includes the time which supplying solution is passing through the tube from solution reservoir to the recording chamber via the pump. Exposing time of cells to the compound solution is more than 5 min after the drug concentration in the chamber well reaches the attempting concentration. There is a subsequent wash period of a 10-20 min to assess reversibility. Finally, the cells are exposed to high dose of dofetilide (5 mM), a specific IKr blocker, to evaluate the insensitive endogenous current.

All experiments are performed at room temperature (23±1° C.). Evoked membrane currents are recorded on-line on a computer, filtered at 500-1 KHz (Bessel-3 dB) and sampled at 1-2 KHz using the patch clamp amplifier and specific data analyzing software. Peak current amplitude, which occurs at around −40 mV, is measured off line on the computer.

The arithmetic mean of the ten values of amplitude is calculated under vehicle control conditions and in the presence of drug. Percent decrease of IN in each experiment was obtained by the normalized current value using the following formula: $IN=(1-ID/IC)\times 100$, where ID is the mean current value in the presence of drug and IC is the mean current value under control conditions. Separate experiments are performed for each drug concentration or time-matched control, and arithmetic mean in each experiment is defined as the result of the study.

Half-Life in Human Liver Microsomes (HLM):

Test compounds (1 μM) are incubated with 3.3 mM $MgCl_2$ and 0.78 mg/mL HLM (HL101) in 100 mM potassium phosphate buffer (pH 7.4) at 37° C. on a 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 min time point indicates the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in a centrifuge (2000 rpm, 15 min). The compound concentration in the supernatant is measured by LC/MS/MS system. The half-life value is obtained by plotting the natural logarithm of the peak area ratio of compounds/internal standard versus time. The slope of the line of best fit through the points yields the rate of metabolism (k). This is converted to a half-life value using following equation:

$$\text{Half-life} = ln2/k.$$

In Vivo Efficacy Assays

P2X3, P2X2/3 antagonists may be tested in various animal models of human diseases, including models of neuropathic, inflammatory, and visceral pain, and models of bladder function. P2X3 antagonists may be administered prior to or post-induction of the model depending upon the specific model and the compound PK characteristics. The route of administration may include intraperitoneal, (i.p.), subcutaneous (s.c.), oral (p.o.), intravenous (i.v.), intrathecal (i.t.), or intraplantar. The endpoints for these studies may include mechanical allodynia, thermal hyperalgesia, cold allodynia, decreased formalin-induced pain responses, decreased writhing and contractions or altered bladder mechanosensation as appropriate for the model as described below.

Formalin Model:

Test compounds are administered at various times prior to intraplantar administration of formalin. A dilute solution of formalin (25-50 μL of 1-2.5% formaldehyde/saline) is administered s.c. into the plantar surface of the left hind paw under light restraint. Immediately following injection, animals are placed on a mesh stand inside a clear observation chamber large enough to allow for free movement of the animals during the study. Behaviors are scored using manual scoring or automated scoring.

Manual scoring: Using a three channel timer, the observer records the time (t in seconds) of decreased weight-bearing ($t_1$), paw lifting ($t_2$), and licking/biting/shaking ($t_3$). Results are weighted according to the method of Dubuisson and Dennis, Pain, 4:161-174, 1977, using the formula $t_1+2t_2+3t_3/180$ where 180 s is the evaluation time for each increment. Behaviors are acquired in alternating 3 min increments starting at time=0 min (i.e. 0-3 min, 6-9 min etc.) and ending at 60 min.

Automated scoring: A small metal band weighing 0.5 g is placed on the left paw. Formalin is administered and the animal placed unrestrained inside an observation chamber over an electromagnetic detector system (Automated Nociception Analyzer, University of California, San Diego). The number of paw flinches is electronically recorded.

ATP and αβ-methylene ATP (αβ meATP)—Induced Inflammatory Pain:

Rats are administered up to 1 μMol αβmeATP, ATP, adenosine, or PBS in a volume up to 100 μL subcutaneously into the dorsal surface of the hindpaw. Immediately after injection, animals are placed on a stand inside a clear observation chamber large enough to allow for free movement of the animals. The duration of flinching and licking are recorded over a 20 minute interval to evaluate nocifensive behavior. Responses are measured using the either the manual or automated methods described above for the Formalin test. Additional behavioral testing may include assessment of mechanical allodynia and thermal hyperalgesia. For testing, compounds are administered prior to agonist injection.

Complete Freund's Adjuvant Model (CFA):

Animals receive an s.c. injection of 100 μL complete Freund's adjuvant containing 100 μg Mycobacterium tuberculosis strain H37Ra into the plantar surface of the right hind paw under isoflurane anesthesia. Swelling and inflammation are visible within 1 h after administration. Nociceptive testing may begin 24 h post CFA administration. Compounds are generally administered 0.5-12 hrs before testing.

Carageenan Induced Acute Pain:

Animals receive a subcutaneous injection of 100 μL of 2% carrageenan into the plantar surface of the right hind paw under isoflurane anesthesia. Swelling and inflammation are visible within 1 h after administration. Nociceptive testing may start 3-24 h post carageenan administration (Hargreaves et al., Pain, 32:77-88, 1988). Compounds are generally administered 0.5-12 hrs before testing.

Chronic Constriction Injury Model (CCI or Bennett Model):

The CCI model is performed according to the method described by Bennett and Xie, Pain, 33:87-107, 1988. Briefly, under isoflurane anesthesia, the right sciatic nerve is exposed at mid-thigh level via blunt dissection through the biceps femoris. Proximal to the bifurcation of the sciatic nerve, about 7 mm of nerve is freed of adhering tissue and 4 loose ligatures of 4.0 chromic gut are tied around the nerve. Spacing between ligatures is approximately 1 mm. The wound is closed in layers, and the skin closed with staples or non-silk sutures. Sham operated animals are treated identically with the exception that the sciatic nerve will not be ligated. Nociceptive testing can be done 7-21 days post surgery. Compounds are generally administered 0.5-12 hrs before testing.

Spinal Nerve Transection (SNT or Chung model):

Under pentobarbital anesthesia (60 mg/kg, i.p.), rats are placed in a prone position on a flat, sterile surface. A midline incision from L4-S2 is made and the left paraspinal muscles are separated from the spinous processes. The L5 and L6 spinal nerves are tightly ligated with a 4-0 silicon-treated silk suture, according to the method described by Kim and Chung, Pain, 50:355-363, 1992. The L4 spinal nerve is carefully preserved from being surgically injured. The skin is closed with wound clips and animals are returned to their home cages. Rats exhibiting prolonged postoperative neurological deficits or poor grooming are excluded from the experiments.

The animals are assessed for nociceptive responses prior to surgery (baseline), then at various timepoints after administration of test compounds. Nociceptive testing can be done 7-21 days post surgery. Compounds are generally administered 0.5-12 hrs before testing.

Chemotherapy-induced Painful Neuropathy:

Chemotherapy neuropathy is induced by i.p. administration of 1 mg/kg Taxol administered once/day on 4 alternating days (total dose=4 mg/kg) (Polomano et al., *Pain*, 94:293-304, 2001). Nociceptive testing can be done 9-30 days after the start of Taxol administration. Compounds are generally administered 0.5-12 hrs before testing.

Nociceptive Testing:

Mechanical Allodynia: Mechanical allodynia testing is performed using the up-down method of Dixon, *Ann. Rev. Pharmacol. Toxicol.* 20:441-462, 1980, modified for mechanical thresholds by Chaplan et al., *J. Neurosci. Methods* 53:55-63, 1994. To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. Each presentation lasts for a period of 4-8 seconds or until a nociceptive withdrawal behavior is observed. Flinching, paw withdrawal or licking of the paw are considered nociceptive behavioral responses. The 50% withdrawal threshold will be calculated using the method described by Chaplan et al., *J. Neurosci. Methods* 53:55-63, 1994

Thermal Hyperalgesia: Hind paw withdrawal latencies to a noxious thermal stimulus are determined using a plantar test apparatus (Ugo Basile) following the technique described by Hargreaves et al., *Pain* 32: 77-88, 1988. The radiant heat sourced is focused onto the plantar surface of the ipsilateral paw, and the paw withdrawal latency is determined. An increase latency of paw withdrawal demonstrates reversal of hyperalgesia.Mechanical Hyperalgesia: The paw pressure assay can be used to assess mechanical hyperalgesia. For this assay, hind paw withdrawal thresholds (PWT) to a noxious mechanical stimulus are determined using an analgesymeter (Ugo Basile) as described in Stein et al., *Pharmacol. Biochem. Behav.* 31:451-455, 1988.

Mechanical Hyperalgesia: The paw pressure assay can be used to assess mechanical hyperalgesia. For this assay, hind paw withdrawal thresholds (PWT) to a noxious mechanical stimulus are determined using an analgesymeter (Ugo Basile) as described in Stein et al., *Pharmacol. Biochem. Behav.* 31:451-455, 1988. The maximum weight that can be applied to the hind paw is set at 250 g and the end point is taken as complete withdrawal of the paw. PWT is determined once for each rat at each time point and only the affected (ipsilateral) paw is tested.

Cold allodynia: To measure cold allodynia, a drop of acetone is applied to the plantar surface of the paw through the underside of the grating on which the animals are standing using a 50 μL Hamilton syringe. The process is performed 5 times with a 3 min interval between each time. Vigorous shaking will be recorded as a positive response, and the time spent shaking is recorded. Alternatively, cold allodynia may be tested using the cold water bath method in which animals are placed into a cold water bath with water at a depth of 1.5-2.0 cm and at a temperature of 3-4 degrees centigrade and the number of paw lifts counted.

Colo-rectal Distension (CRD):

Prior to induction of the model, animals are deprived of food but allowed access to water ad libitum for 16 h prior to the induction of the model. A 5 cm latex balloon is attached to a barostat system composed of a flow meter and pressure control program by a length of tubing. Under isoflurane anesthesia, the balloon is inserted into the distal colon via the anus at a distance of 5 cm from the anus and taped to the base of the tail. Post-anesthesia, the animal is placed unrestrained into a clean polypropylene cage and allowed to acclimate for 30 mins. The balloon is progressively inflated from 0-75 mmHg in 5 mm increments every 30 seconds. The colonic reaction threshold is defined as the pressure inducing the first abdominal contraction. Abdominal contraction indicative of visceral pain correlates with hunching, hump-backed position, licking of the lower abdomen, repeated waves of contraction of the ipsilateral oblique musculature with inward turning of the ipsilateral hindlimb, stretching, squashing of the lower abdomen against the floor (Wesselman, *Neurosci. Lett.,* 246:73-76, 1998). Alternatively, electrodes may be placed into the external oblique musculature for eletromyographic recordings of abdominal contractions. In this case, EMG activity is quantified during colonic balloon inflation. Compounds are generally administered 0.5-12 hrs before testing.

Acetic Acid Writhing Test:

A 0.6% solution of acetic acid (10 mL/kg) is administered i.p. to rats and the number of abdominal constrictions within 30 min are counted. Compounds are generally administered 0.5-12 hrs before testing.

Bladder Afferent Nerve Recordings:

In order to determine the precise role of inhibition of P2X3 and P2X2/3 receptors in the micturition response, test compounds will be examined for their ability to modulate afferent signaling from the urinary bladder. Compounds are evaluated in the urinary bladder/pelvic nerve preparation described by Vlaskovska et al., *J Neuroscience,* 21:5670-7, 2001, and Cockayne et al., *J. Physiol.* 567:621-39, 2005. Briefly, the whole urinary tract attached to the lower vertebrae and surrounding tissues is isolated en bloc and superfused in a recording chamber with oxygenated (5% $CO_2$ and 95% $O_2$) Krebs solution. The bladder is catheterized through the urethra for intraluminal infusion. A second double lumen catheter is inserted into the bladder to measure intraluminal pressure and to drain the bladder. After the bladder is prepared, the pelvic nerve exiting the vertebrae is dissected and impaled with a suction glass electrode. Nerve activity is measured using standard electrophysiological methods. Following a 60 min stabilization period, repeated ramp distensions are performed until the afferent response stabilizes. This stabilized afferent response was used for comparing mechanosensitivity of bladder afferents between different treatment groups.

Isovolumetric Bladder Contraction Assay:

Female Sprague-Dawley rats are anesthetized, tracheotomized, and cannulated in the carotid artery and femoral vein. The urinary bladder is accessed via an abdominal incision, and the ureters ligated and transected. For fluid infusion and pressure measurements, the urinary bladder is cannulated.

Post surgery, the bladder is infused with saline until stable volume-induced bladder contractions are elicited. Once stable threshold volumes and contraction frequencies are obtained, the animal is dosed with compound and contraction frequency is measured.

Refill and Cystitis Models of Bladder Function:

Animals are anaesthetized, and transurethral closed cystometry was conducted as previously described (Dmitrieva et al., *Neuroscience* 78:449-59, 1997; Cockayne et al., Nature 407:1011-5, 2000). The bladder is catheterized transurethrally with a PE-10 polypropylene catheter. Each cystometrogram consists of slowly filling the bladder with normal saline via the transurethral catheter, and then recording the pressure associated with filling via a pressure transducer. Contractions greater than a predetermined threshold value are interpreted as micturition contractions. For each cystometrogram, the volume at which active contractions occurred (micturition threshold) and the number of contractions per cystometrogram are recorded. The effects of compounds are then determined.

Cystometrograms may also be obtained in animal cystitis models in which bladders are irritated by injection of cyclophosphamide (150 mg/kg, i.p.) 24 hrs prior to cystometry, or by infusion of up to 1% acetic acid during cystometry.

The synthetic and biological examples described in this application are offered to illustrate the compounds, pharmaceutical compositions and methods provided herein and are not to be construed in any way as limiting their scope. In the examples, all temperatures are in degrees Celsius (unless otherwise indicated). Compounds that can be prepared in accordance with the methods provided herein along with their biological activity data are presented in following Table. The syntheses of these representative compounds are carried out in accordance with the methods set forth above.

Exemplary Compounds Provided Herein

The following compounds can be prepared according to the synthetic methods described herein. A calcium uptake assay was performed as described above and the results are shown in Table 1 wherein the activity of each compound is expressed in Table 1 as follows:

TABLE 1

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 1 | 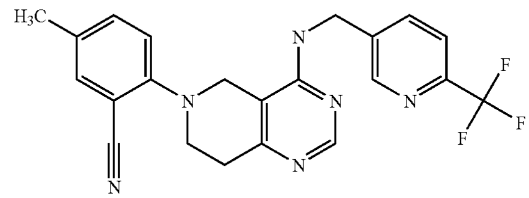 | 424.43 | 425.2 | 19 | 92 |
| 2 | 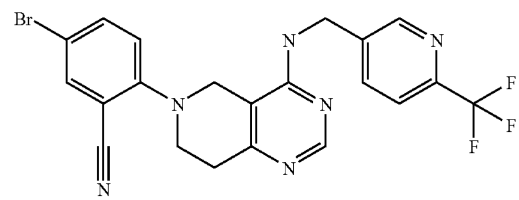 | 489.3 | 491.1 | 80 | |
| 3 | 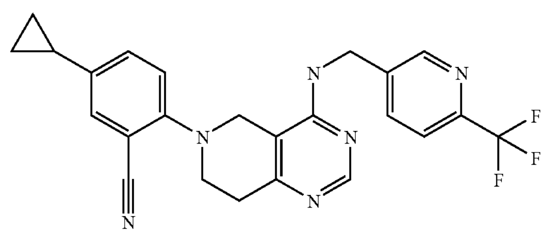 | 450.47 | 451 | 870 | |
| 4 | 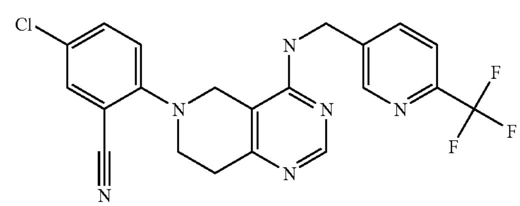 | 444.85 | 444.7 | 37 | 842 |
| 5 | 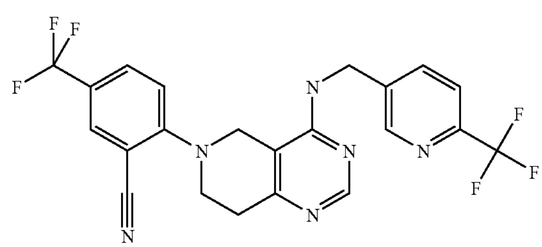 | 478.4 | 479.3 | 1840 | |

TABLE 1-continued

Exemplary 2-Cyanophenyl Fused Heterocyclic Compounds

| ID | STRUCTURE | | MW | MS (obsd) | P2X3 IC$_{50}$ (nM) | P2X2/3 IC$_{50}$ (nM) |
|---|---|---|---|---|---|---|
| 6 | 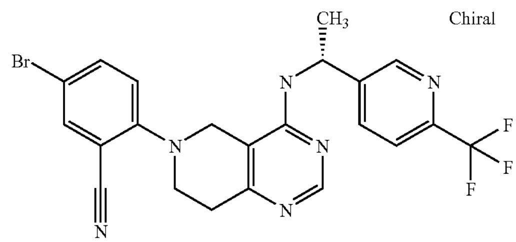 | Chiral | 503.32 | 505 | 42 | 455 |
| 7 | 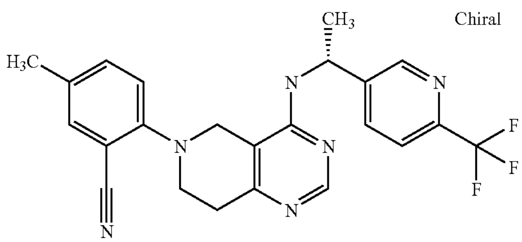 | Chiral | 438.45 | 439.2 | 22 | 42 |
| 8 | 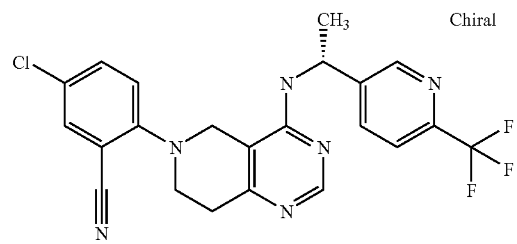 | Chiral | 458.87 | 459.1 | 25 | 383 |
| 9 | 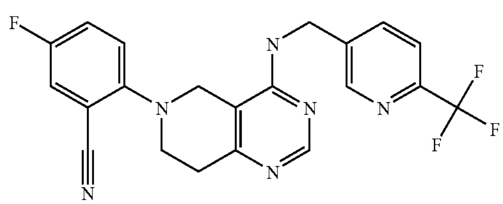 | | 428.39 | 429.6 | 85 | 11432 |
| 10 | 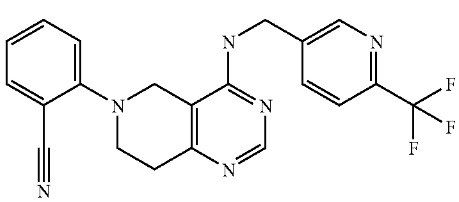 | | 410.4 | 411.2 | 63 | 1814 |
| 11 | 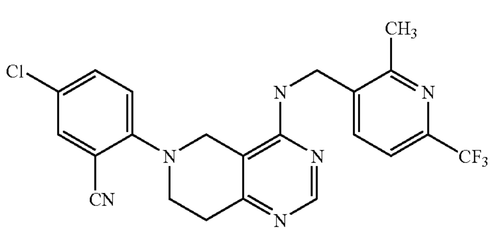 | | 458.87 | 459 | 187 | >10000 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 12 | 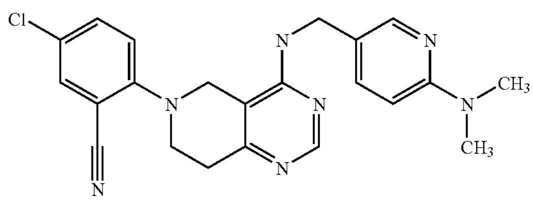 | 419.92 | 420.5 | 628 | 1190 |
| 13 | 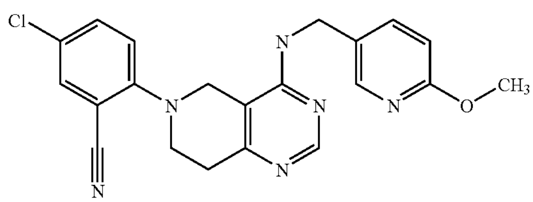 | 406.88 | 407.1 | 59 | 169 |
| 14 | 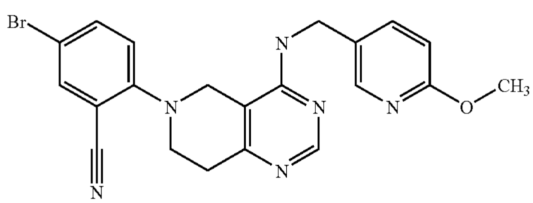 | 451.33 | 453.1 | 78 | 325 |
| 15 | 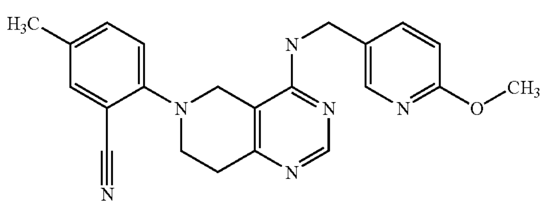 | 386.46 | 387.4 | 9 | 27 |
| 16 | 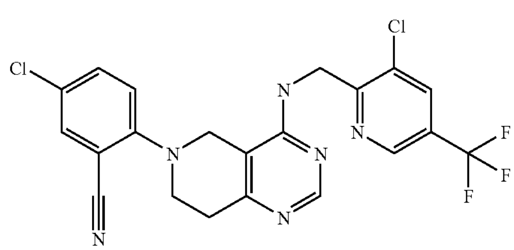 | 479.29 | 481.1 | 91 | 1128 |
| 17 | 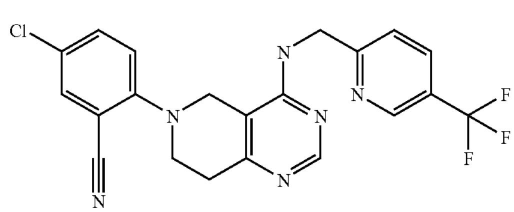 | 444.85 | 445.3 | 118 | 4886 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 18 | 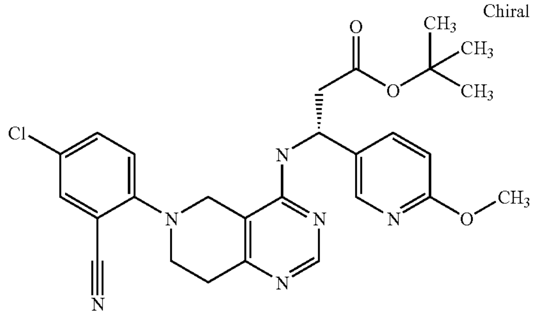 | 521.02 | 521.4 | >10000 | >10000 |
| 19 | 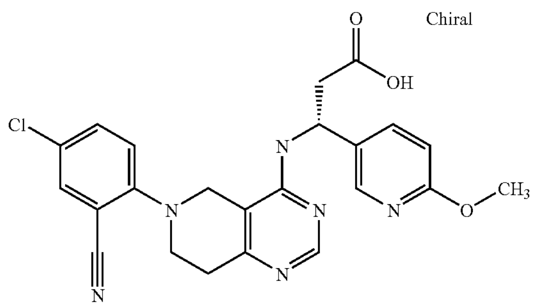 | 464.91 | | 1379 | >10000 |
| 20 | 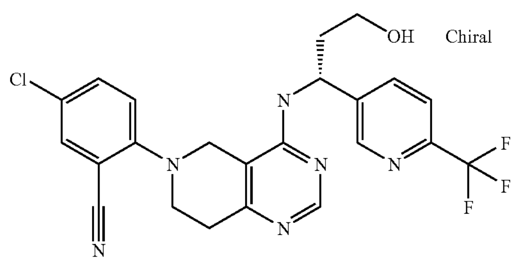 | 488.9 | 489.2 | 90 | 903 |
| 21 | 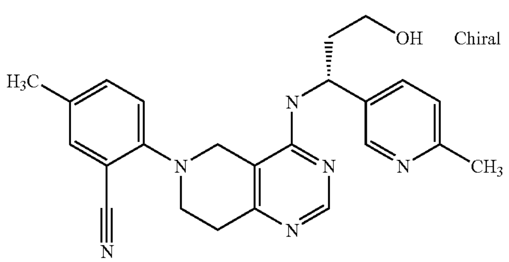 | 414.51 | 415.5 | 12 | 31 |
| 22 | 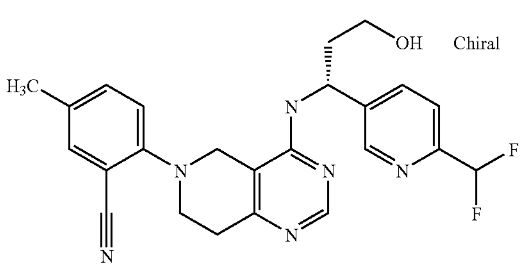 | 450.49 | 451.2 | 13 | 43 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 23 | Chiral | 416.48 | 417.5 | 6 | 28 |
| 24 | Chiral | 430.51 | 431.3 | 14 | 20 |
| 25 | 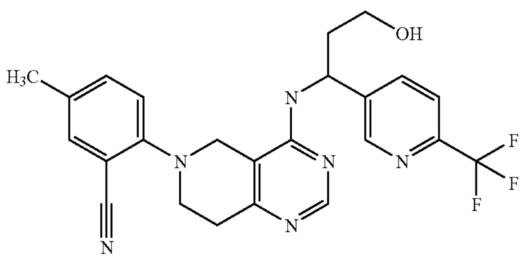 | 468.48 | 469.4 | 55 | 136 |
| 26 | Chiral | 430.51 | 431.2 | 43 | 397 |
| 27 | 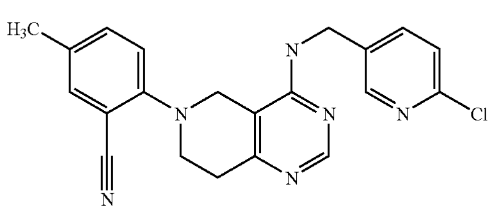 | 390.88 | 391.4 | 11 | 25 |
| 28 | 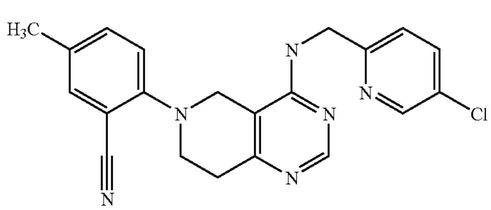 | 390.88 | 391.4 | 29 | 152 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 29 | 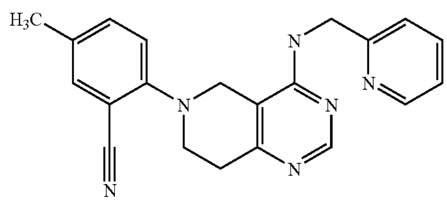 | 356.43 | 357.3 | 196 | 1674 |
| 30 | 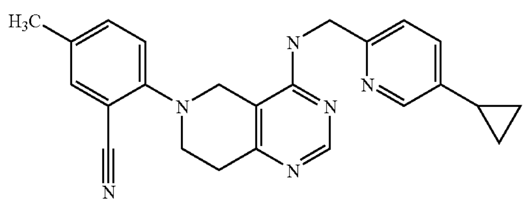 | 396.5 | 397.3 | 236 | 377 |
| 31 | 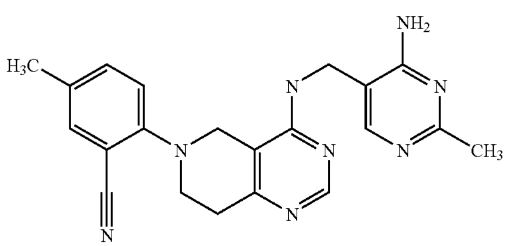 | 386.46 | 387.5 | 16 | 92 |
| 32 | 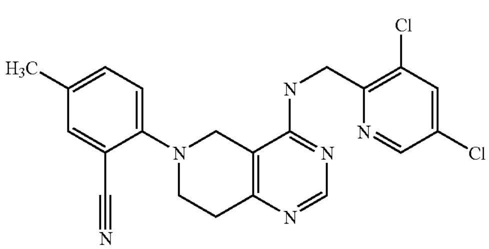 | 425.32 | 425.3 | 41 | 50 |
| 33 | 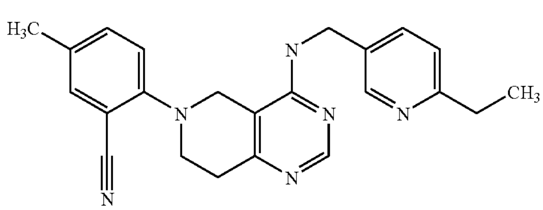 | 384.48 | 385.3 | 38 | 127 |
| 34 | 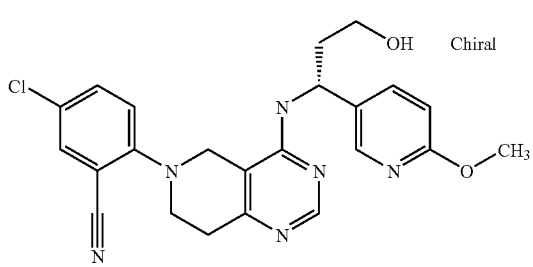 | 450.93 | 451.3 | 33 | 105 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 35 | Chiral | 436.9 | 437.4 | 23 | 200 |
| 36 | 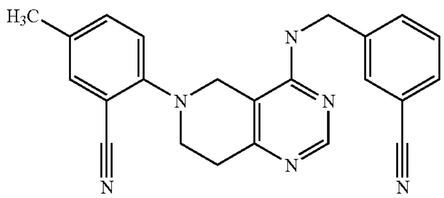 | 380.45 | 381.3 | 183 | 1093 |
| 37 | 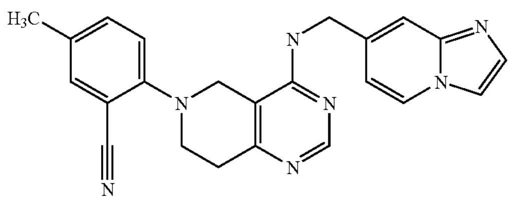 | 395.47 | 396.4 | 18 | 33 |
| 38 | 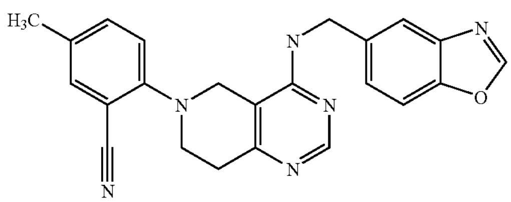 | 396.45 | 397.4 | 15 | 45 |
| 39 | 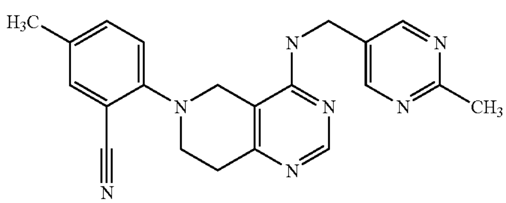 | 371.45 | 372.2 | 12 | 82 |
| 40 | 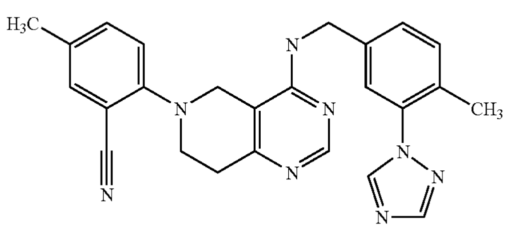 | 436.52 | 437.4 | 21 | 92 |

TABLE 1-continued
Exemplary 2-Cyanophenyl Fused Heterocyclic Compounds
| ID | STRUCTURE | MW | MS (obsd) | P2X3 IC$_{50}$ (nM) | P2X2/3 IC$_{50}$ (nM) |
|---|---|---|---|---|---|
| 41 | 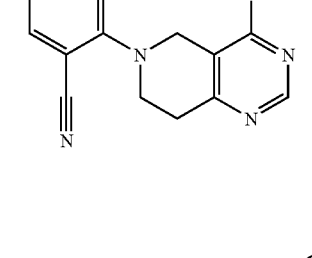 | 444.49 | | 207 | 1676 |
| 42 | 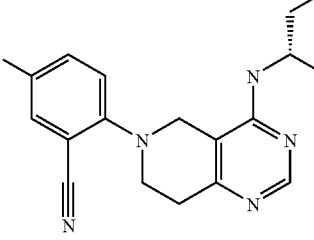 | 443.51 | 444.4 | 26 | 174 |
| 43 | 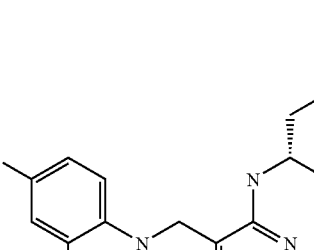 | 471.56 | 472.5 | 302 | 2211 |
| 44 | 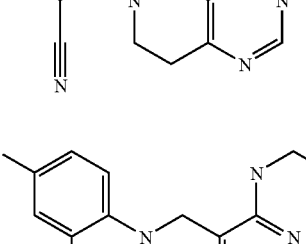 | 415.89 | 416.4 | 122 | 753 |
| 45 | 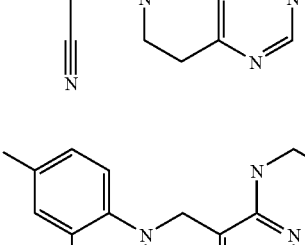 | 391.86 | 392.4 | 28 | 246 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 46 | Chiral | 454.45 | 455.2 | 21 | 71 |
| 47 | Chiral | 474.87 | 475.4 | 54 | 671 |
| 48 | 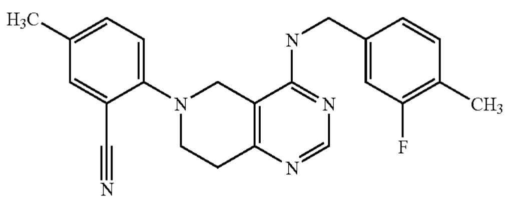 | 387.46 | 388.1 | 89 | 124 |
| 49 | 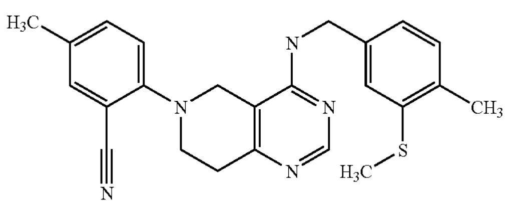 | 415.56 | 416.3 | 474 | 925 |
| 50 | 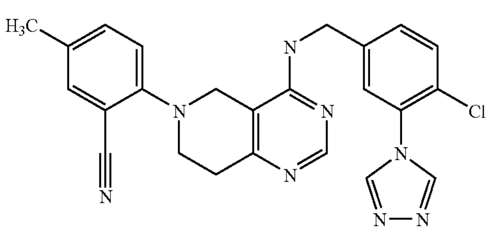 | 456.94 | 457.1 | 31 | 63 |
| 51 | 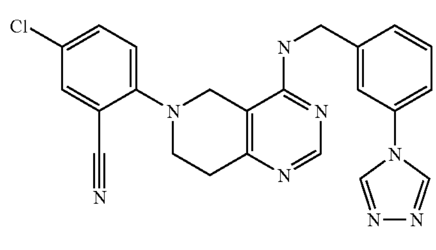 | 442.91 | 443.5 | 284 | 1015 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 52 | 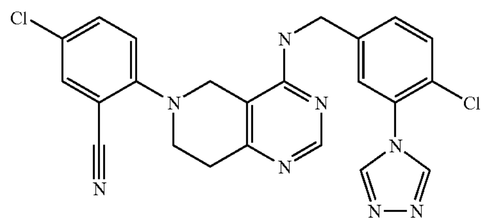 | 477.36 | 476.8 | 41 | 286 |
| 53 | 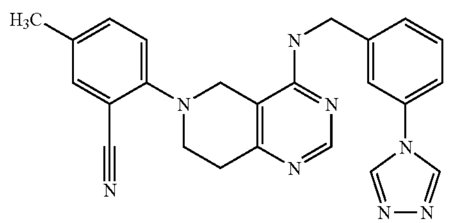 | 422.49 | 423.4 | 65 | 324 |
| 54 | 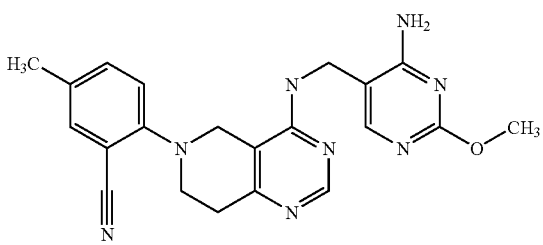 | 402.46 | 403 | 32 | 62 |
| 55 | 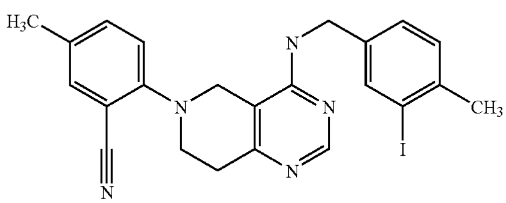 | 495.36 | 496.4 | 512 | 1296 |
| 56 | 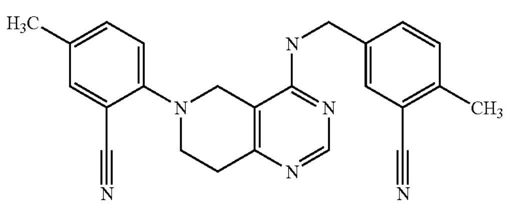 | 394.48 | 395 | 63 | 82 |
| 57 | 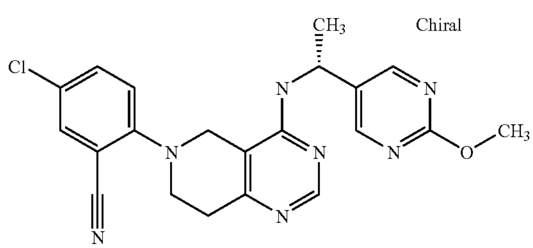 | 421.89 | 422.4 | 34 | 1724 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 58 | Chiral | 401.47 | 402 | 10 | 164 |
| 59 | 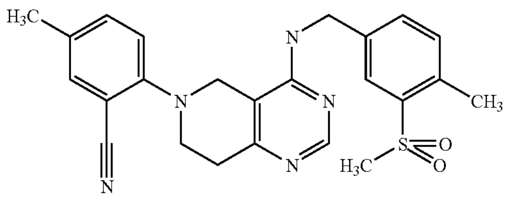 | 447.56 | 448.6 | 16 | 55 |
| 60 | Chiral | 417.47 | 418.4 | 14 | 130 |
| 61 | 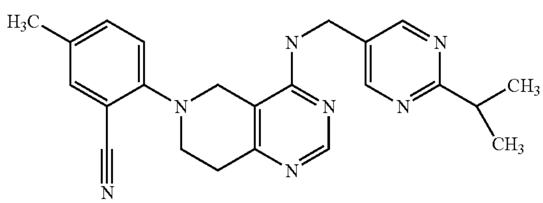 | 399.5 | 400.4 | 101 | 1346 |
| 62 | Chiral | 470.91 | 471.3 | 32 | 273 |
| 63 | 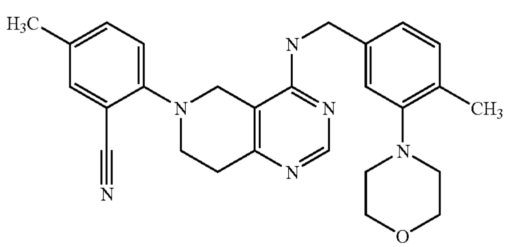 | 454.58 | 455.4 | 96 | 1121 |

TABLE 1-continued
Exemplary 2-Cyanophenyl Fused Heterocyclic Compounds
| ID | STRUCTURE | MW | MS (obsd) | P2X3 IC$_{50}$ (nM) | P2X2/3 IC$_{50}$ (nM) |
|---|---|---|---|---|---|
| 64 | 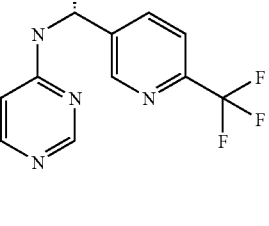 | 468.48 | 469.4 | 23 | 59 |
| 65 | 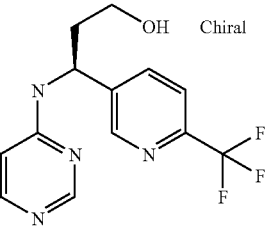 | 468.48 | 469.3 | 806 | 5419 |
| 66 | 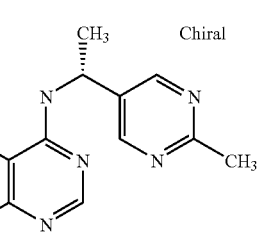 | 385.47 | 386.1 | 14 | 30 |
| 67 | 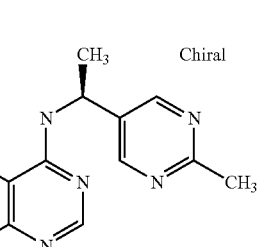 | 385.47 | 385.9 | 486 | 3797 |
| 68 | 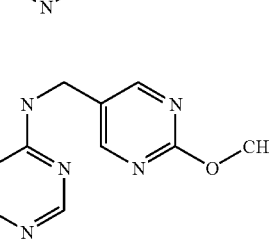 | 387.44 | 388.3 | 13 | 42 |
| 69 | 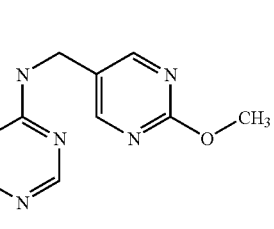 | 407.86 | 407.8 | 42 | 224 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 70 | Chiral | 436.46 | 437.3 | 7 | 33 |
| 71 | 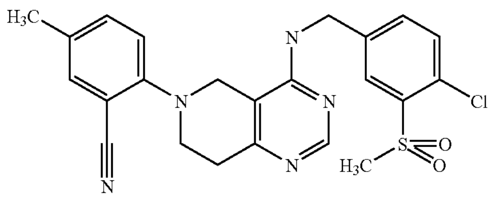 | 467.98 | 468.4 | 37 | 120 |
| 72 | Chiral | 456.88 | 457.2 | 16 | 404 |
| 73 | Chiral | 421.89 | 422.5 | 15 | 225 |
| 74 | Chiral | 401.47 | 402.3 | 7 | 61 |
| 75 | Chiral | 405.89 | 406.3 | 15 | 180 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 76 | 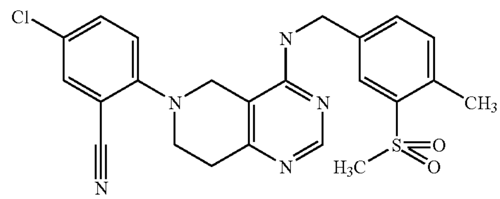 | 467.98 | 468.4 | 40 | 241 |
| 77 | Chiral | 510.52 | 511.2 | 130 | 536 |
| 78 | Chiral | 437.89 | 438.2 | 42 | 854 |
| 79 | 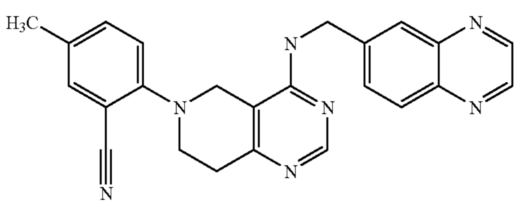 | 407.48 | 408.2 | 34 | 67 |
| 80 | 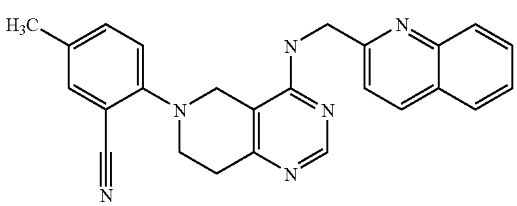 | 406.49 | 407.3 | 156 | 263 |
| 81 | 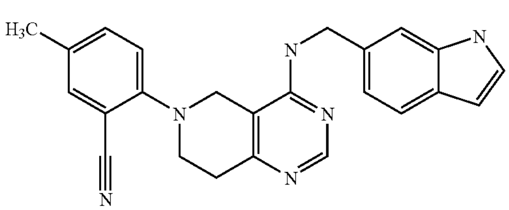 | 394.48 | 395.3 | 423 | 2163 |

TABLE 1-continued
Exemplary 2-Cyanophenyl Fused Heterocyclic Compounds
| ID | STRUCTURE | MW | MS (obsd) | P2X3 IC$_{50}$ (nM) | P2X2/3 IC$_{50}$ (nM) |
|---|---|---|---|---|---|
| 82 | 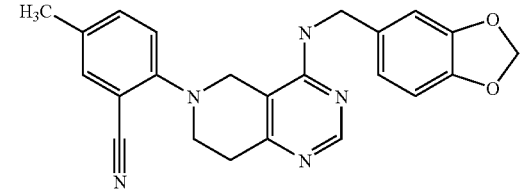 | 399.45 | 400.3 | 56 | 310 |
| 83 | 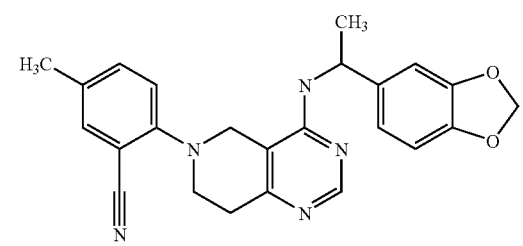 | 413.48 | 413.9 | 54 | 125 |
| 84 | 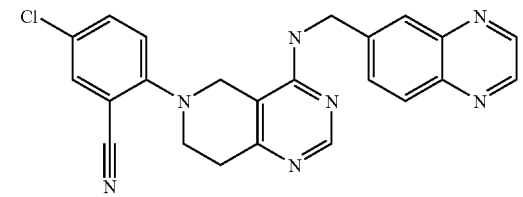 | 427.9 | 428.2 | 125 | 478 |
| 85 | 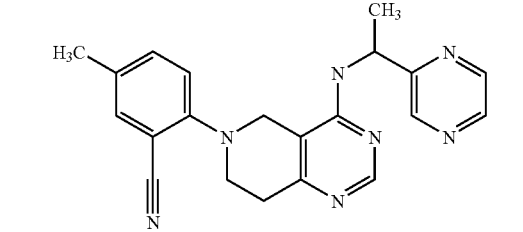 | 371.45 | 372.2 | 37 | 663 |
| 86 | 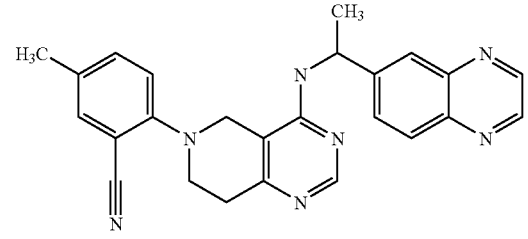 | 421.51 | 421.9 | 75 | 276 |
| 87 | 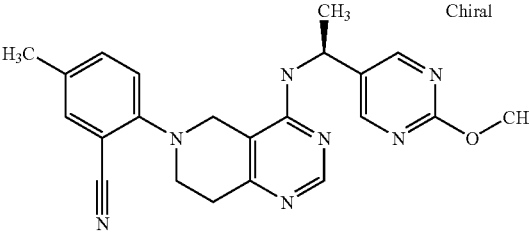 Chiral | 401.47 | 401.8 | 481 | 5363 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|----|-----------|-----|-----------|---------------------|-----------------------|
| 88 | 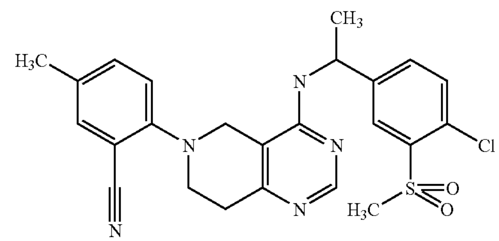 | 482.01 | 482.2 | 36 | 19 |
| 89 | Chiral | 413.48 | 414.4 | 15 | 19 |
| 90 | Chiral | 413.48 | 414.4 | 2206 | 7074 |
| 91 | 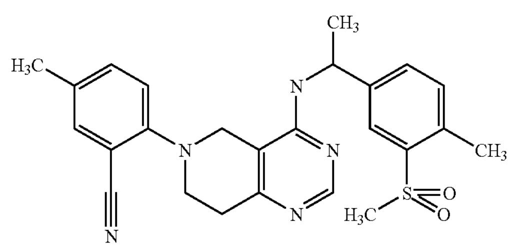 | 461.59 | 462.3 | 23 | 45 |
| 92 | 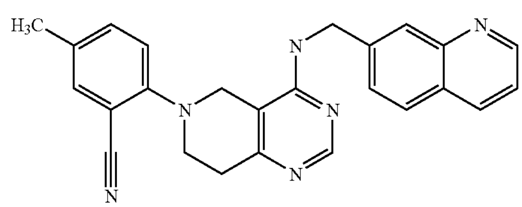 | 406.49 | 407.3 | 20 | 24 |
| 93 | Chiral | 482.01 | 482.3 | 17 | 12 |

TABLE 1-continued

Exemplary 2-Cyanophenyl Fused Heterocyclic Compounds

| ID | STRUCTURE | MW | MS (obsd) | P2X3 IC$_{50}$ (nM) | P2X2/3 IC$_{50}$ (nM) |
|---|---|---|---|---|---|
| 94 | Chiral | 482.01 | 482.3 | 430 | 4546 |
| 95 | Chiral | 421.51 | 422.5 | 15 | 45 |
| 96 | Chiral | 421.51 | 422.5 | 570 | >10000 |

Pharmacokinetic Evaluation of Compounds Following Intravenous and Oral Administration in Rats.

Male Sprague-Dawley rats are acclimatized for at least 24 hours prior to experiment initiation. During the acclimation period, all animals receive food and water ad libitum. However, food but not water is removed from the animal's cages at least 12 hours before initiation of the experiment. During the first 3 hours of experimentation, the animals receive only water ad libitum. At least three animals each are tested for intravenous and oral dosage. For intravenous formulation, compounds are dissolved (0.25 to 1 mg/mL) in a mixture of 3% dimethyl sulfoxide, 40% PEG 400 and the rest percentage of 40% Captisol in water (w/v). The animals are weighed before dosing. The determined body weight is used to calculate the dose volume for each animal.

Dose volume(mL/kg)=1 mg/kg/formulation concentration(mg/mL)

In instances where the formulation concentrations are less than 0.5 mg/mL, the dosing volume is about 2 mL/kg.

For oral formulation, compounds of this invention are suspended (0.5 to 0.75 mg/mL) in a mixture of 5% of 10% Tween 80 in water (v/v) and 95% of 0.5% methyl cellulose in water (w/v). PO rats are typically dosed through oral gavage following the same dose volume formula as IV to achieve a dose level of 1 to 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing, blood samples are collected (using a pre-heparinized syringe) via the jugular vein catheter before dosing and at 5, 15, 30, 60, 120, 180, 300, 480, and 1440 minutes post dosing. About 250 µL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 4° C. and the upper plasma layer transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite (AUC$_{inf}$). The AUC$_{inf}$ is averaged and the oral bioavailability (% F) for individual animal is calculated as:

AUC$_{inf}$(PO)/AUC$_{inf}$(IV), normalized to their respective dose levels.

The % F can be reported as the mean % F of all animals dosed orally with the compound of the invention at the specified level.

Plasma Protein Binding

The plasma protein binding of compounds of invention is measured in human and rat plasma, respectively. A stock solution of the tested compound is prepared in 1 mg/mL in DMSO solution. The stock solution is spiked into the blank plasma to get a final compound concentration at 1 µg/mL for testing. Equilibrium dialysis (The equilibrium dialyzer-96™ MWCO 5K Daltons, Harvard Apparatus) method is used for the testing purpose.

The compound spiked plasma (at 1 μg/mL) and phosphate buffer (0.1 M, pH 7.4), 200 μl each, are added into the opposite sides of the membrane in a 96-well equilibrium dialyzer, respectively. The dialyzer plate is covered and incubated overnight (16 hr) at 37° C. in the 8-plate rotor incubator (Big Shot III 8-plate rotor, Harvard Apparatus). Aliquots (100 μL) are taken from the plasma and the buffer compartments, respectively. The matrix effects are eliminated by adding the same volume of blank plasma into the samples from buffer compartments and adding the same volume of phosphate buffer into the samples from plasma compartments. The samples are extracted by using the regular (3:1) protein precipitation extraction procedure (acetonitrile with internal standard). The supernatants are taken for LC/MS/MS analysis. The percentage of plasma-protein binding can be calculated by using the following method:

% Free=[Free Drug/Total Drug]*100=[(Peak Area)$_{buffer}$/(Peak Area)$_{plasma}$]*100% Bound=100−% Free.

From the foregoing description, various modifications and changes in the compositions and methods provided herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A compound according to formula 1:

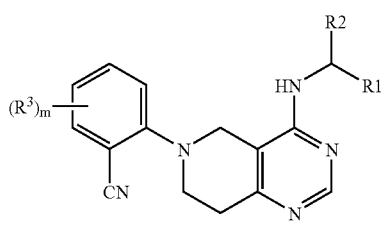

wherein
R$^1$ is aryl or heteroaryl unsubstituted or substituted with one or more R$^4$ groups;

R$^2$ is H, substituted or unsubstituted C$_1$-C$_6$ alkyl or cycloalkyl;

each R$^3$ and R$^4$ is independently selected from the group consisting of H, alkyl, acyl, acylamino, alkylamino, alkylthio, alkoxy, alkoxycarbonyl, alkylarylamino, arylalkyloxy, arylalkyloxy, amino, aryl, arylalkyl, —SO$_3$H, —SO$_3$R$^{61b}$, wherein R$^{61b}$ is a substituted or unsubstituted alkyl or a substituted or unsubstituted aryl, —S(O$_2$)R$^{61}$, wherein R$^{61}$ is a substituted or unsubstituted alkyl or a substituted or unsubstituted aryl, —SOR$^{61a}$, wherein R$^{61a}$ is a substituted or unsubstituted alkyl, a substituted or unsubstituted aryl or a substituted or unsubstituted heteroaryl, —SR, wherein R is a substituted or unsubstituted alkyl, a substituted or unsubstituted aryl or a substituted or unsubstituted heteroaryl, azido, carbamoyl, carboxyl, cyano, cycloalkyl, cycloheteroalkyl, dialkylamino, halo, heteroaryloxy, heteroaryl, heteroalkyl, hydroxy, nitro, and SH; and m is 1, 2, 3, or 4;

or a pharmaceutically acceptable salt, tautomer or isotopic variant thereof.

2. A compound according to formula 2:

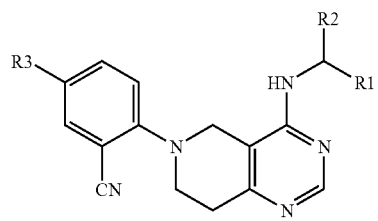

wherein R$^1$, R$^2$ and R$^4$ are as in claim 1; and R$^3$ is halo, substituted or unsubstituted C$_1$-C$_6$ alkyl or cycloalkyl; or a pharmaceutically acceptable salt, tautomer or isotopic variant thereof.

3. An enantiomerically pure compound according to formula 3a or 3b:

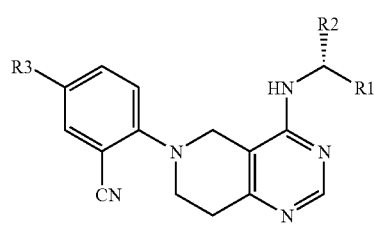

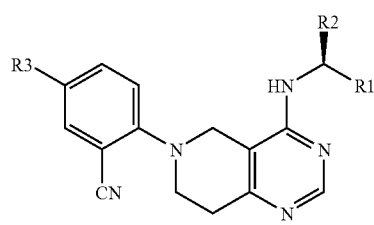

wherein R$^1$, R$^2$ and R$^4$ are as in claim 1; and R$^3$ is halo, substituted or unsubstituted C$_1$-C$_6$ alkyl or cycloalkyl; or a pharmaceutically acceptable salt, tautomer or isotopic variant thereof.

4. A compound according to any one of claims 1-3, wherein $R^1$ is selected from unsubstituted phenyl, pyridyl, pyrimidinyl, quinolinyl, isoquinolinyl, quinoxaline, methylenedioxyphenyl, imidazopyridyl, benzoxazolyl, and indolyl.

5. A compound according to any one of claims 1-3, wherein $R^1$ is selected from quinolinyl, isoquinolinyl, quinoxaline, methylenedioxyphenyl, imidazopyridyl, benzoxazolyl, and indolyl, substituted with one or more groups selected from Me, Et, Pr, iso-Pr, Ph, Cl, F, Br, CN, OH, OMe, OEt, OPh, COPh, CO$_2$Me, CH$_2$—N-morpholino, CH$_2$—N-(4-Me-piperidino), NH$_2$, CONH$_2$, CF$_3$, CHF$_2$, OCF$_3$, OCHF$_2$, t-Bu, SMe, CH=CH—CO$_2$H, SOMe, SO$_2$Me, SO$_2$CF$_3$, SO$_2$NH$_2$, SO$_3$H, SO$_3$Me, and cyclopropyl.

6. A compound according to any one of claims 1-3, wherein $R^1$ is

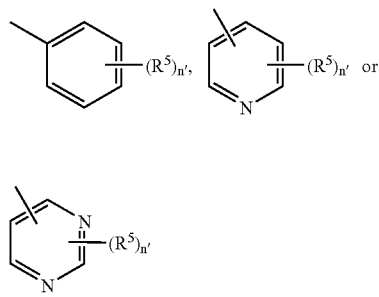

and wherein subscript n' is selected from 1-5 and each $R^5$ is independently selected from hydrogen, substituted or unsubstituted alkyl, substituted or unsubstituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, —SO$_3$H, —SO$_3$R$^{61b}$, wherein R$^{61b}$ is a substituted or unsubstituted alkyl or a substituted or unsubstituted aryl, —S(O$_2$)R$^{61}$, wherein R$^{61}$ is a substituted or unsubstituted alkyl or a substituted or unsubstituted aryl, —SOR$^{61a}$, wherein R$^{61a}$ is a substituted or unsubstituted alkyl, a substituted or unsubstituted aryl or a substituted or unsubstituted heteroaryl, —SR, wherein R is a substituted or unsubstituted alkyl, a substituted or unsubstituted aryl or a substituted or unsubstituted heteroaryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and SH.

7. A compound according to claim 6, wherein the subscript n' is 1 or 2; and each $R^5$ is independently selected from H, Me, Et, Pr, iso-Pr, Ph, Cl, F, Br, CN, OH, OMe, OEt, OPh, COPh, CO$_2$Me, CH$_2$—N-morpholino, CH$_2$—N-(4-Me-piperidino), NH$_2$, CONH$_2$, CF$_3$, CHF$_2$, OCF$_3$, OCHF$_2$, t-Bu, SMe, CH=CH—CO$_2$H, SOMe, SO$_2$Me, SO$_2$CF$_3$, SO$_2$NH$_2$, SO$_3$H, SO$_3$Me, cyclopropyl, triazolyl, morpholinyl, and pyridyl.

8. A compound according to claim 1, wherein the compound is according to formula 4a, 4b, or 4c:

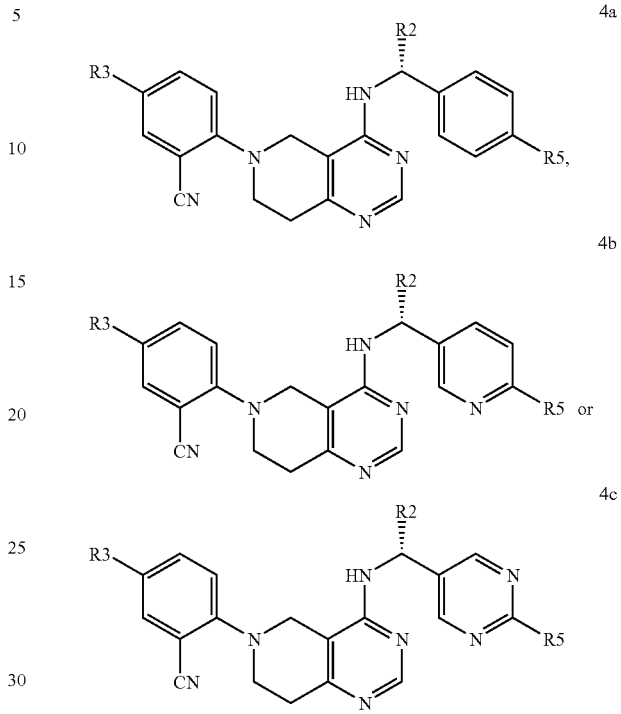

and wherein $R^2$ is as in claim 1; $R^3$ is halo, substituted or unsubstituted $C_1$-$C_6$ alkyl or cycloalkyl; and each $R^5$ is independently selected from hydrogen, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, —SO$_3$H, —SO$_3$R$^{61b}$, wherein R$^{61b}$ is a substituted or unsubstituted alkyl or a substituted or unsubstituted aryl, —S(O$_2$)R$^{61}$, wherein R$^{61}$ is a substituted or unsubstituted alkyl or a substituted or unsubstituted aryl, —SOR$^{61a}$, wherein R$^{61a}$ is a substituted or unsubstituted alkyl, a substituted or unsubstituted aryl or a substituted or unsubstituted heteroaryl, —SR, wherein R is a substituted or unsubstituted alkyl, a substituted or unsubstituted aryl or a substituted or unsubstituted heteroaryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and SH.

9. A compound according to claim 6, wherein each $R^5$ is independently selected from H, Me, Et, Pr, iso-Pr, Ph, Cl, F, CN, OH, OMe, OEt, OPh, CF$_3$, CHF$_2$, OCF$_3$, OCHF$_2$, t-Bu, SO$_2$Me, SO$_2$CF$_3$, and SO$_3$Me.

10. A compound according to claim 6, wherein $R^5$ is H, Cl, F, Me, CF$_3$, or OMe.

11. A compound according to any one of claims 1-3 and 8, wherein $R^2$ is selected from H, Me, Et, n-Pr, t-Bu, CF$_3$, CH$_2$OH, CH$_2$CH$_2$OH, CH$_2$CH$_2$OAc, CH$_2$(CH$_2$)$_2$OH, CH$_2$CH$_2$NHMe, CH$_2$NMe$_2$, CH$_2$CH$_2$NMe$_2$, CH$_2$CONH$_2$, CH$_2$CONMe$_2$, CH$_2$COOH, CH$_2$CH$_2$COOH, CH$_2$(CH$_2$)$_2$COOH, CH$_2$OMe, and CH$_2$CH$_2$OMe.

12. A compound according to any one of claims 1-3 and 8, wherein $R^2$ is selected from $CH_2NR^{2'}R^{2''}$, $CH_2CH_2NR^{2'}R^{2''}$, and $CH_2CH_2CH_2NR^{2'}R^{2''}$; and wherein $R^{2'}$ and $R^{2''}$ can join together to form a heterocyclic ring.

13. A compound according to any one of claims 1-3 and 8, wherein $R^2$ is selected from cyclopropyl, cyclobutyl or cyclohexyl.

14. A compound according to any one of claims 1-3 and 8, wherein $R^2$ is Me.

15. A compound according to any one of claims 1-3 and 8, $R^2$ is $CH_2OH$ or $CH_2CH_2OH$.

16. A compound according to any one of claims 1-3 and 8, wherein $R^3$ is substituted or unsubstituted alkyl.

17. A compound according to any one of claims 1-3 and 8, wherein $R^3$ is Me or $CF_3$.

18. A compound according to any one of claims 1-3 and 8, $R^3$ is Cl.

19. A compound according to claim 1, wherein the compound is according to formula 5a, 5b, or 5c:

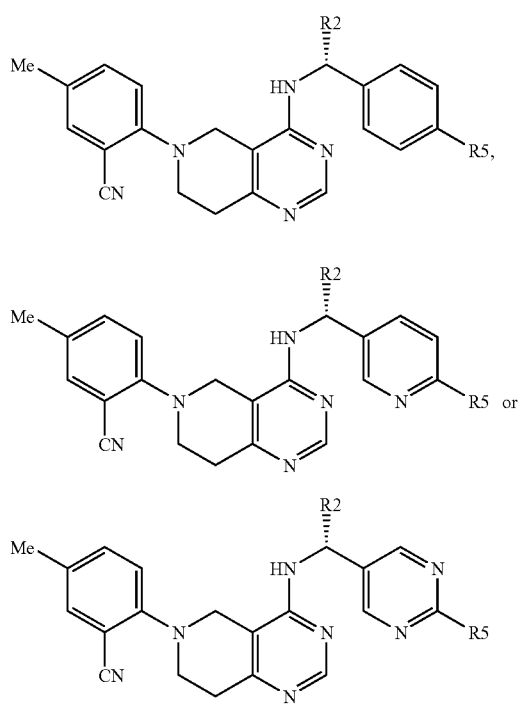

and wherein $R^2$ is as in claim 1; and each $R^5$ is independently selected from hydrogen, substituted or unsubstituted alkyl, substituted or unsubstituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, —$SO_3OH$, —$SO_3R^{61b}$, wherein $R^{61b}$ is a substituted or unsubstituted alkyl or a substituted or unsubstituted aryl, —$S(O_2)R^{61}$, wherein $R^{61}$ is a substituted or unsubstituted alkyl or a substituted or unsubstituted aryl, —$SOR^{61a}$, wherein $R^{61a}$ is a substituted or unsubstituted alkyl, a substituted or unsubstituted aryl or a substituted or unsubstituted heteroaryl, —SR, wherein R is a substituted or unsubstituted alkyl, a substituted or unsubstituted aryl or a substituted or unsubstituted heteroaryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and SH.

20. A compound according to claim 19, wherein $R^2$ is H, Me, Et, $CH_2OH$, or $CH_2CH_2OH$.

21. A compound according to claim 19, wherein $R^5$ is H, Cl, F, Me, $CF_3$, or OMe.

22. A compound according to claim 1, selected from the group consisting of:
 5-Methyl-2-{4-[(6-trifluoromethyl-pyridin-3-ylmethyl)-amino]-7,8-dihydro-5H-pyrido[4,3-d]pyrimidin-6-yl}-benzonitrile;
 5-Bromo-2-{4-[(6-trifluoromethyl-pyridin-3-ylmethyl)-amino]-7,8-dihydro-5H-pyrido[4,3-d]pyrimidin-6-yl}-benzonitrile;
 5-Cyclopropyl-2-{4-[(6-trifluoromethyl-pyridin-3-ylmethyl)-amino]-7,8-dihydro-5H-pyrido[4,3-d]pyrimidin-6-yl}-benzonitrile;
 5-Chloro-2-{4-[(6-trifluoromethyl-pyridin-3-ylmethyl)-amino]-7,8-dihydro-5H-pyrido[4,3-d]pyrimidin-6-yl}-benzonitrile;
 5-Trifluoromethyl-2-{4-[(6-trifluoromethyl-pyridin-3-ylmethyl)-amino]-7,8-dihydro-5H-pyrido[4,3-d]pyrimidin-6-yl}-benzonitrile;
 5-Bromo-2-{4-[(R)-1-(6-trifluoromethyl-pyridin-3-yl)-ethylamino]-7,8-dihydro-5H-pyrido[4,3-d]pyrimidin-6-yl}-benzonitrile;
 5-Methyl-2-{4-[(R)-1-(6-trifluoromethyl-pyridin-3-yl)-ethylamino]-7,8-dihydro-5H-pyrido[4,3-d]pyrimidin-6-yl}-benzonitrile;
 5-Chloro-2-{4-[(R)-1-(6-trifluoromethyl-pyridin-3-yl)-ethylamino]-7,8-dihydro-5H-pyrido[4,3-d]pyrimidin-6-yl}-benzonitrile;
 5-Fluoro-2-{4-[(6-trifluoromethyl-pyridin-3-ylmethyl)-amino]-7,8-dihydro-5H-pyrido[4,3-d]pyrimidin-6-yl}-benzonitrile;
 2-{4-[(6-Trifluoromethyl-pyridin-3-ylmethyl)-amino]-7,8-dihydro-5H-pyrido[4,3-d]pyrimidin-6-yl}-benzonitrile;
 5-Chloro-2-{4-[(2-methyl-6-trifluoromethyl-pyridin-3-ylmethyl)-amino]-7,8-dihydro-5H-pyrido[4,3-d]pyrimidin-6-yl}-benzonitrile;
 5-Chloro-2-{4-[(6-dimethylamino-pyridin-3-ylmethyl)-amino]-7,8-dihydro-5H-pyrido[4,3-d]pyrimidin-6-yl}-benzonitrile;
 5-Chloro-2-{4-[(6-methoxy-pyridin-3-ylmethyl)-amino]-7,8-dihydro-5H-pyrido[4,3-d]pyrimidin-6-yl}-benzonitrile;
 5-Bromo-2-{4-[(6-methoxy-pyridin-3-ylmethyl)-amino]-7,8-dihydro-5H-pyrido[4,3-d]pyrimidin-6-yl}-benzonitrile;
 2-{4-[(6-Methoxy-pyridin-3-ylmethyl)-amino]-7,8-dihydro-5H-pyrido[4,3-d]pyrimidin-6-yl}-5-methyl-benzonitrile;
 5-Chloro-2-{4-[(3-chloro-5-trifluoromethyl-pyridin-2-ylmethyl)-amino]-7,8-dihydro-5H-pyrido[4,3-d]pyrimidin-6-yl}-benzonitrile;
 5-Chloro-2-{4-[(5-trifluoromethyl-pyridin-2-ylmethyl)-amino]-7,8-dihydro-5H-pyrido[4,3-d]pyrimidin-6-yl}-benzonitrile;
 (R)-3-[6-(4-Chloro-2-cyano-phenyl)-5,6,7,8-tetrahydro-pyrido[4,3-d]pyrimidin-4-ylamino]-3-(6-methoxy-pyridin-3-yl)-propionic acid tert-butyl ester;

(R)-3-[6-(4-Chloro-2-cyano-phenyl)-5,6,7,8-tetrahydro-pyrido[4,3-d]pyrimidin-4-ylamino]-3-(6-methoxy-pyridin-3-yl)-propionic acid;

5-Chloro-2-{4-[(R)-3-hydroxy-1-(6-trifluoromethyl-pyridin-3-yl)-propylamino]-7,8-dihydro-5H-pyrido[4,3-d]pyrimidin-6-yl}-benzonitrile;

2-{4-[(R)-3-Hydroxy-1-(6-methyl-pyridin-3-yl)-propylamino]-7,8-dihydro-5H-pyrido[4,3-d]pyrimidin-6-yl}-5-methyl-benzonitrile;

2-{4-[(R)-1-(6-Difluoromethyl-pyridin-3-yl)-3-hydroxy-propylamino]-7,8-dihydro-5H-pyrido[4,3-d]pyrimidin-6-yl}-5-methyl-benzonitrile;

2-{4-[(S)-2-Hydroxy-1-(6-methoxy-pyridin-3-yl)-ethylamino]-7,8-dihydro-5H-pyrido[4,3-d]pyrimidin-6-yl}-5-methyl-benzonitrile;

2-{4-[(R)-3-Hydroxy-1-(6-methoxy-pyridin-3-yl)-propylamino]-7,8-dihydro-5H-pyrido[4,3-d]pyrimidin-6-yl}-5-methyl-benzonitrile;

2-{4-[3-Hydroxy-1-(6-trifluoromethyl-pyridin-3-yl)-propylamino]-7,8-dihydro-5H-pyrido[4,3-d]pyrimidin-6-yl}-5-methyl-benzonitrile;

2-{4-[(S)-2-Methoxy-1-(6-methoxy-pyridin-3-yl)-ethylamino]-7,8-dihydro-5H-pyrido[4,3-d]pyrimidin-6-yl}-5-methyl-benzonitrile;

2-{4-[(6-Chloro-pyridin-3-ylmethyl)-amino]-7,8-dihydro-5H-pyrido[4,3-d]pyrimidin-6-yl}-5-methyl-benzonitrile;

2-{4-[(5-Chloro-pyridin-2-ylmethyl)-amino]-7,8-dihydro-5H-pyrido[4,3-d]pyrimidin-6-yl}-5-methyl-benzonitrile;

5-Methyl-2-{4-[(pyridin-2-ylmethyl)-amino]-7,8-dihydro-5H-pyrido[4,3-d]pyrimidin-6-yl}-benzonitrile;

2-{4-[(5-Cyclopropyl-pyridin-2-ylmethyl)-amino]-7,8-dihydro-5H-pyrido[4,3-d]pyrimidin-6-yl}-5-methyl-benzonitrile;

2-{4-[(4-Amino-2-methyl-pyrimidin-5-ylmethyl)-amino]-7,8-dihydro-5H-pyrido[4,3-d]pyrimidin-6-yl}-5-methyl-benzonitrile;

2-{4-[(3,5-Dichloro-pyridin-2-ylmethyl)-amino]-7,8-dihydro-5H-pyrido[4,3-d]pyrimidin-6-yl}-5-methyl-benzonitrile;

2-{4-[(6-Ethyl-pyridin-3-ylmethyl)-amino]-7,8-dihydro-5H-pyrido[4,3-d]pyrimidin-6-yl}-5-methyl-benzonitrile;

5-Chloro-2-{4-[(R)-3-hydroxy-1-(6-methoxy-pyridin-3-yl)-propylamino]-7,8-dihydro-5H-pyrido[4,3-d]pyrimidin-6-yl}-benzonitrile;

5-Chloro-2-{4-[(S)-2-hydroxy-1-(6-methoxy-pyridin-3-yl)-ethylamino]-7,8-dihydro-5H-pyrido[4,3-d]pyrimidin-6-yl}-benzonitrile;

2-[4-(3-Cyano-benzylamino)-7,8-dihydro-5H-pyrido[4,3-d]pyrimidin-6-yl]-5-methyl-benzonitrile;

2-{4-[(Imidazo[1,2-a]pyridin-7-ylmethyl)-amino]-7,8-dihydro-5H-pyrido[4,3-d]pyrimidin-6-yl}-5-methyl-benzonitrile;

2-{4-[(Benzooxazol-5-ylmethyl)-amino]-7,8-dihydro-5H-pyrido[4,3-d]pyrimidin-6-yl}-5-methyl-benzonitrile;

5-Methyl-2-{4-[(2-methyl-pyrimidin-5-ylmethyl)-amino]-7,8-dihydro-5H-pyrido[4,3-d]pyrimidin-6-yl}-benzonitrile;

5-Methyl-2-[4-(4-methyl-3-[1,2,4]triazol-1-yl-benzylamino)-7,8-dihydro-5H-pyrido[4,3-d]pyrimidin-6-yl]-benzonitrile;

(R)-3-[6-(2-Cyano-4-methyl-phenyl)-5,6,7,8-tetrahydro-pyrido[4,3-d]pyrimidin-4-ylamino]-3-(6-methoxy-pyridin-3-yl)-propionic acid;

(R)-3-[6-(2-Cyano-4-methyl-phenyl)-5,6,7,8-tetrahydro-pyrido[4,3-d]pyrimidin-4-ylamino]-3-(6-methoxy-pyridin-3-yl)-propionamide;

(R)-3-[6-(2-Cyano-4-methyl-phenyl)-5,6,7,8-tetrahydro-pyrido[4,3-d]pyrimidin-4-ylamino]-3-(6-methoxy-pyridin-3-yl)-N,N-dimethyl-propionamide;

5-Chloro-2-{4-[(imidazo[1,2-a]pyridin-7-ylmethyl)-amino]-7,8-dihydro-5H-pyrido[4,3-d]pyrimidin-6-yl}-benzonitrile;

5-Chloro-2-{4-[(2-methyl-pyrimidin-5-ylmethyl)-amino]-7,8-dihydro-5H-pyrido[4,3-d]pyrimidin-6-yl}-benzonitrile;

2-{4-[(S)-2-Hydroxy-1-(6-trifluoromethyl-pyridin-3-yl)-ethylamino]-7,8-dihydro-5H-pyrido[4,3-d]pyrimidin-6-yl}-5-methyl-benzonitrile;

5-Chloro-2-{4-[(S)-2-hydroxy-1-(6-trifluoromethyl-pyridin-3-yl)-ethylamino]-7,8-dihydro-5H-pyrido[4,3-d]pyrimidin-6-yl}-benzonitrile;

2-[4-(3-Fluoro-4-methyl-benzylamino)-7,8-dihydro-5H-pyrido[4,3-d]pyrimidin-6-yl]-5-methyl-benzonitrile;

5-Methyl-2-[4-(4-methyl-3-methylsulfanyl-benzylamino)-7,8-dihydro-5H-pyrido[4,3-d]pyrimidin-6-yl]-benzonitrile;

2-[4-(4-Chloro-3-[1,2,4]triazol-4-yl-benzylamino)-7,8-dihydro-5H-pyrido[4,3-d]pyrimidin-6-yl]-5-methyl-benzonitrile;

5-Chloro-2-[4-(3-[1,2,4]triazol-4-yl-benzylamino)-7,8-dihydro-5H-pyrido[4,3-d]pyrimidin-6-yl]-benzonitrile;

5-Chloro-2-[4-(4-chloro-3-[1,2,4]triazol-4-yl-benzylamino)-7,8-dihydro-5H-pyrido[4,3-d]pyrimidin-6-yl]-benzonitrile;

5-Methyl-2-[4-(3-[1,2,4]triazol-4-yl-benzylamino)-7,8-dihydro-5H-pyrido[4,3-d]pyrimidin-6-yl]-benzonitrile;

2-{4-[(4-Amino-2-methoxy-pyrimidin-5-ylmethyl)-amino]-7,8-dihydro-5H-pyrido[4,3-d]pyrimidin-6-yl}-5-methyl-benzonitrile;

2-[4-(3-Iodo-4-methyl-benzylamino)-7,8-dihydro-5H-pyrido[4,3-d]pyrimidin-6-yl]-5-methyl-benzonitrile;

5-Chloro-2-{4-[(R)-1-(2-methoxy-pyrimidin-5-yl)-ethylamino]-7,8-dihydro-5H-pyrido[4,3-d]pyrimidin-6-yl}-benzonitrile;

2-{4-[(R)-1-(2-Methoxy-pyrimidin-5-yl)-ethylamino]-7,8-dihydro-5H-pyrido[4,3-d]pyrimidin-6-yl}-5-methyl-benzonitrile;

2-[4-(3-Methanesulfonyl-4-methyl-benzylamino)-7,8-dihydro-5H-pyrido[4,3-d]pyrimidin-6-yl]-5-methyl-benzonitrile;

2-{4-[(S)-2-Hydroxy-1-(2-methoxy-pyrimidin-5-yl)-ethylamino]-7,8-dihydro-5H-pyrido[4,3-d]pyrimidin-6-yl}-5-methyl-benzonitrile;

2-{4-[(2-Isopropyl-pyrimidin-5-ylmethyl)-amino]-7,8-dihydro-5H-pyrido[4,3-d]pyrimidin-6-yl}-5-methyl-benzonitrile;

5-Chloro-2-{4-[(R)-1-(6-difluoromethyl-pyridin-3-yl)-3-hydroxy-propylamino]-7,8-dihydro-5H-pyrido[4,3-d]pyrimidin-6-yl}-benzonitrile;

5-Methyl-2-[4-(4-methyl-3-morpholin-4-yl-benzylamino)-7,8-dihydro-5H-pyrido[4,3-d]pyrimidin-6-yl]-benzonitrile;

2-{4-[(R)-3-Hydroxy-1-(6-trifluoromethyl-pyridin-3-yl)-propylamino]-7,8-dihydro-5H-pyrido[4,3-d]pyrimidin-6-yl}-5-methyl-benzonitrile;

2-{4-[(S)-3-Hydroxy-1-(6-trifluoromethyl-pyridin-3-yl)-propylamino]-7,8-dihydro-5H-pyrido[4,3-d]pyrimidin-6-yl}-5-methyl-benzonitrile;

5-Methyl-2-{4-[(R)-1-(2-methyl-pyrimidin-5-yl)-ethylamino]-7,8-dihydro-5H-pyrido[4,3-d]pyrimidin-6-yl}-benzonitrile;
5-Methyl-2-{4-[(S)-1-(2-methyl-pyrimidin-5-yl)-ethylamino]-7,8-dihydro-5H-pyrido[4,3-d]pyrimidin-6-yl}-benzonitrile;
2-{4-[(2-Methoxy-pyrimidin-5-ylmethyl)-amino]-7,8-dihydro-5H-pyrido[4,3-d]pyrimidin-6-yl}-5-methyl-benzonitrile;
5-Chloro-2-{4-[(2-methoxy-pyrimidin-5-ylmethyl)-amino]-7,8-dihydro-5H-pyrido[4,3-d]pyrimidin-6-yl}-benzonitrile;
2-{4-[(S)-1-(6-Difluoromethyl-pyridin-3-yl)-2-hydroxy-ethylamino]-7,8-dihydro-5H-pyrido[4,3-d]pyrimidin-6-yl}-5-methyl-benzonitrile;
2-[4-(4-Chloro-3-methanesulfonyl-benzylamino)-7,8-dihydro-5H-pyrido[4,3-d]pyrimidin-6-yl]-5-methyl-benzonitrile;
5-Chloro-2-{4-[(S)-1-(6-difluoromethyl-pyridin-3-yl)-2-hydroxy-ethylamino]-7,8-dihydro-5H-pyrido[4,3-d]pyrimidin-6-yl}-benzonitrile;
5-Chloro-2-{4-[(S)-2-hydroxy-1-(2-methyl-pyrimidin-5-yl)-ethylamino]-7,8-dihydro-5H-pyrido[4,3-d]pyrimidin-6-yl}-benzonitrile;
2-{4-[(S)-2-Hydroxy-1-(2-methyl-pyrimidin-5-yl)-ethylamino]-7,8-dihydro-5H-pyrido[4,3-d]pyrimidin-6-yl}-5-methyl-benzonitrile;
5-Chloro-2-{4-[(R)-1-(2-methyl-pyrimidin-5-yl)-ethylamino]-7,8-dihydro-5H-pyrido[4,3-d]pyrimidin-6-yl}-benzonitrile;
5-Chloro-2-[4-(3-methanesulfonyl-4-methyl-benzylamino)-7,8-dihydro-5H-pyrido[4,3-d]pyrimidin-6-yl]-benzonitrile;
Acetic acid (R)-3-[6-(2-cyano-4-methyl-phenyl)-5,6,7,8-tetrahydro-pyrido[4,3-d]pyrimidin-4-ylamino]-3-(6-trifluoromethyl-pyridin-3-yl)-propyl ester;
5-Chloro-2-{4-[(S)-2-hydroxy-1-(2-methoxy-pyrimidin-5-yl)-ethylamino]-7,8-dihydro-5H-pyrido[4,3-d]pyrimidin-6-yl}-benzonitrile;
5-Methyl-2-{4-[(quinoxalin-6-ylmethyl)-amino]-7,8-dihydro-5H-pyrido[4,3-d]pyrimidin-6-yl}-benzonitrile;
5-Methyl-2-{4-[(quinolin-2-ylmethyl)-amino]-7,8-dihydro-5H-pyrido[4,3-d]pyrimidin-6-yl}-benzonitrile;
2-{4-[(1H-Indol-6-ylmethyl)-amino]-7,8-dihydro-5H-pyrido[4,3-d]pyrimidin-6-yl}-5-methyl-benzonitrile;
2-{4-[(Benzo[1,3]dioxol-5-ylmethyl)-amino]-7,8-dihydro-5H-pyrido[4,3-d]pyrimidin-6-yl}-5-methyl-benzonitrile;
2-[4-(1-Benzo[1,3]dioxol-5-yl-ethylamino)-7,8-dihydro-5H-pyrido[4,3-d]pyrimidin-6-yl]-5-methyl-benzonitrile;
5-Chloro-2-{4-[(quinoxalin-6-ylmethyl)-amino]-7,8-dihydro-5H-pyrido[4,3-d]pyrimidin-6-yl}-benzonitrile;
5-Methyl-2-[4-(1-pyrazin-2-yl-ethylamino)-7,8-dihydro-5H-pyrido[4,3-d]pyrimidin-6-yl]-benzonitrile;
5-Methyl-2-[4-(1-quinoxalin-6-yl-ethylamino)-7,8-dihydro-5H-pyrido[4,3-d]pyrimidin-6-yl]-benzonitrile;
2-{4-[(S)-1-(2-Methoxy-pyrimidin-5-yl)-ethylamino]-7,8-dihydro-5H-pyrido[4,3-d]pyrimidin-6-yl}-5-methyl-benzonitrile;
2-{4-[1-(4-Chloro-3-methanesulfonyl-phenyl)-ethylamino]-7,8-dihydro-5H-pyrido[4,3-d]pyrimidin-6-yl}-5-methyl-benzonitrile;
2-[4-((R)-1-Benzo[1,3]dioxol-5-yl-ethylamino)-7,8-dihydro-5H-pyrido[4,3-d]pyrimidin-6-yl]-5-methyl-benzonitrile;
2-[4-((S)-1-Benzo[1,3]dioxol-5-yl-ethylamino)-7,8-dihydro-5H-pyrido[4,3-d]pyrimidin-6-yl]-5-methyl-benzonitrile;
2-{4-[1-(3-Methanesulfonyl-4-methyl-phenyl)-ethylamino]-7,8-dihydro-5H-pyrido[4,3-d]pyrimidin-6-yl}-5-methyl-benzonitrile;
5-Methyl-2-{4-[(quinolin-7-ylmethyl)-amino]-7,8-dihydro-5H-pyrido[4,3-d]pyrimidin-6-yl}-benzonitrile;
2-{4-[(R)-1-(4-Chloro-3-methanesulfonyl-phenyl)-ethylamino]-7,8-dihydro-5H-pyrido[4,3-d]pyrimidin-6-yl}-5-methyl-benzonitrile;
2-{4-[(S)-1-(4-Chloro-3-methanesulfonyl-phenyl)-ethylamino]-7,8-dihydro-5H-pyrido[4,3-d]pyrimidin-6-yl}-5-methyl-benzonitrile;
5-Methyl-2-[4-((R)-1-quinoxalin-6-yl-ethylamino)-7,8-dihydro-5H-pyrido[4,3-d]pyrimidin-6-yl]-benzonitrile; and
5-Methyl-2-[4-((S)-1-quinoxalin-6-yl-ethylamino)-7,8-dihydro-5H-pyrido[4,3-d]pyrimidin-6-yl]-benzonitrile;
2-[4-(3-cyano-4-methylbenzylamino)-7,8-dihydro-5H-pyrido[4,3-d]pyrimidin-6-yl]-5-methyl-benzonitrile;
or a pharmaceutically acceptable salt, stereoisomer, tautomer or isotopic variant thereof.

23. A pharmaceutical composition comprising a pharmaceutically acceptable carrier and a pharmaceutically effective amount of a compound of claim 1.

24. The pharmaceutical composition of claim 23, wherein the carrier is suitable for parenteral, oral or topical administration.

* * * * *